US010836821B2

(12) United States Patent
Miao et al.

(10) Patent No.: US 10,836,821 B2
(45) Date of Patent: Nov. 17, 2020

(54) DRUG-CONJUGATES WITH A TARGETING MOLECULE AND TWO DIFFERENT DRUGS

(71) Applicant: Sorrento Therapeutics, Inc., San Diego, CA (US)

(72) Inventors: Zhenwei Miao, San Diego, CA (US); Gang Chen, San Diego, CA (US); Tong Zhu, San Diego, CA (US); Alisher B. Khasanov, San Diego, CA (US); Yufeng Hong, San Diego, CA (US); Hong D. Zhang, San Diego, CA (US); Alexander Chucholowski, Poway, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 590 days.

(21) Appl. No.: 14/515,352

(22) Filed: Oct. 15, 2014

(65) Prior Publication Data

US 2015/0105540 A1  Apr. 16, 2015

Related U.S. Application Data

(60) Provisional application No. 61/891,310, filed on Oct. 15, 2013.

(51) Int. Cl.
*A61K 47/65* (2017.01)
*A61K 47/68* (2017.01)
*A61K 47/55* (2017.01)
*C07K 16/28* (2006.01)
*C07K 16/18* (2006.01)

(52) U.S. Cl.
CPC .............. *C07K 16/28* (2013.01); *A61K 47/55* (2017.08); *A61K 47/65* (2017.08); *A61K 47/6801* (2017.08); *C07K 16/18* (2013.01)

(58) Field of Classification Search
None
See application file for complete search history.

(56) References Cited

U.S. PATENT DOCUMENTS

| | | |
|---|---|---|
| 5,780,588 A | 7/1998 | Pettit et al. |
| 6,124,431 A | 9/2000 | Sakakibara et al. |
| 6,569,834 B1 | 5/2003 | Pettit et al. |
| 7,531,162 B2 | 5/2009 | Collins et al. |
| 7,767,205 B2 | 8/2010 | Mao et al. |
| 7,829,531 B2 | 11/2010 | Senter et al. |
| 7,994,135 B2 | 8/2011 | Doronina et al. |
| 8,088,387 B2 | 1/2012 | Steeves et al. |
| 8,470,984 B2 | 6/2013 | Caruso et al. |
| 2004/0121965 A1* | 6/2004 | Greenberger ........ A61K 31/191 514/617 |
| 2005/0238649 A1 | 10/2005 | Doronina et al. |
| 2006/0128754 A1 | 6/2006 | Hoeft et al. |
| 2007/0134243 A1 | 6/2007 | Gazzard et al. |
| 2009/0318668 A1* | 12/2009 | Beusker ............ C07D 209/60 530/331 |
| 2011/0206658 A1 | 8/2011 | Crowley et al. |
| 2011/0217321 A1 | 9/2011 | Torgov et al. |
| 2011/0245295 A1 | 10/2011 | Chai et al. |
| 2011/0263650 A1 | 10/2011 | Ellman et al. |
| 2011/0268751 A1 | 11/2011 | Sievers et al. |
| 2011/0301334 A1 | 12/2011 | Bhakta et al. |
| 2012/0148610 A1 | 6/2012 | Doronina et al. |
| 2013/0029900 A1 | 1/2013 | Widdison |
| 2013/0101546 A1 | 4/2013 | Yurkovetskiy et al. |
| 2013/0224228 A1 | 8/2013 | Jackson et al. |
| 2014/0030282 A1 | 1/2014 | Polakis et al. |
| 2015/0105539 A1 | 4/2015 | Miao et al. |
| 2015/0141646 A1 | 5/2015 | Miao et al. |
| 2016/0067350 A1 | 3/2016 | Miao et al. |

FOREIGN PATENT DOCUMENTS

| | | | |
|---|---|---|---|
| CA | 2813056 A1 | 4/2012 | |
| EP | 0624377 A2 | 11/1994 | |
| WO | 2005/081711 A2 | 9/2005 | |
| WO | 2007/109567 A1 | 9/2007 | |
| WO | 2010/009124 A2 | 1/2010 | |
| WO | 2012/010287 A1 | 1/2012 | |
| WO | 2012/166559 A1 | 12/2012 | |
| WO | 2012/166560 A1 | 12/2012 | |
| WO | WO 2013085925 A1 * | 6/2013 | ....... A61K 39/39558 |
| WO | 2013/173391 A1 | 11/2013 | |
| WO | 2013/173392 A1 | 11/2013 | |
| WO | 2013/173393 A1 | 11/2013 | |
| WO | 2013/185117 A1 | 12/2013 | |
| WO | 2013/192360 A1 | 12/2013 | |

(Continued)

OTHER PUBLICATIONS

Tannock, I.F. (Experimental Chemotherapy, Ch. 19—p. 338 and 352-359, in The Basic Science of Oncology Tannock and Hill, eds., New York 1992).*

Cella, R., et al., "Steroselective Synthesis of the Dolastatin Units by Organtriflouroborates Additions to Alpha-Amino Aldehydes", Tetrahedron Letters, 49 (2008) 16-19.

Ducry, L. et al., "Antibody-Drug Conjugates: Linking Cytotoxic Payloads to Monoclonal Antibodies" Bioconjugate Chemistry, 2010, vol. 21, No. 1, pp. 5-13.

Kingston, David "Tubulin Interactive Natural Products as Anticancer Agents" J Nat Prod. Mar. 2009; 72(3): 507-515.

Pettit, et al., "Specific Activities of Dolastatin 10 and Peptide Derivatives Against Crypococcus neoformans" Antimicrobial Agents and Chemotherapy, Nov. 1998, p. 2961-2965.

(Continued)

*Primary Examiner* — Misook Yu
*Assistant Examiner* — Kauser M Akhoon
(74) *Attorney, Agent, or Firm* — McNeill Baur PLLC

(57) ABSTRACT

There is disclosed an improved ADC (antibody drug conjugate) type composition having at least two different drug payloads conjugated to a single targeting protein. More specifically, the present disclosure attaches a first drug conjugate to a dual Cysteine residue on a targeting protein and a second drug conjugate with a different drug to a Lys residue on the targeting protein.

14 Claims, 3 Drawing Sheets

(56) References Cited

FOREIGN PATENT DOCUMENTS

| WO | 2015/057876 A1 | 4/2015 |
| WO | 2016/123412 A1 | 8/2016 |
| WO | 2016/127081 A1 | 8/2016 |

OTHER PUBLICATIONS

PubChemCompound datasheet (online compound summary) CID 56841603; Create Date: Mar. 21, 2012; http://pubchem.ncbi.nlm.nih.gov/summary/summary.cgi?cid=56841603.

Younes, A. et al., "Brentuximab Vedotin (SGN-35) for Relapsed CD30-Positive Lymphomas" The New England Journa of Medicine, 363; 19, 2010, 1812-1821.

Extended European Search Report for European Application No. 14854041.2, dated Jun. 6, 2017, 6 pages.

\* cited by examiner

DRUG-CONJUGATES WITH A TARGETING MOLECULE AND TWO DIFFERENT DRUGS

CROSS REFERENCE TO RELATED APPLICATION

This patent application claims priority from U.S. provisional patent application 61/891,310 filed 15 Oct. 2013.

TECHNICAL FIELD

The present disclosure provides an improved ADC (antibody drug conjugate) type composition having at least two different drug payloads conjugated to a single targeting protein. More specifically, the present disclosure attaches a first drug conjugate to a dual Cysteine residue on a targeting protein and a second drug conjugate with a different drug to a Lys residue on the targeting protein.

BACKGROUND

An antibody (or antibody fragment) can be linked to a payload drug to form an immunoconjugate that has been termed antibody-drug conjugate, or ADC. The antibody causes the ADC to bind to the target cells. Often the ADC is then internalized by the cell and the drug is released to treat the cell. Because of the targeting, the side effects may be lower than the side effects of systemically administering the drug.

SUMMARY

The present disclosure provides active agent-conjugates that include at least two different types of drugs. A first drug is conjugated to sulfhydryl groups of a targeting protein on Cys residues within four amino acids of each other, such as on an antibody hinge region, and a second drug conjugated to an amino groups of Lys side chains of the targeting protein.

Specifically, the present disclosure provides a dual active agent-conjugate having the structure of Formula I:

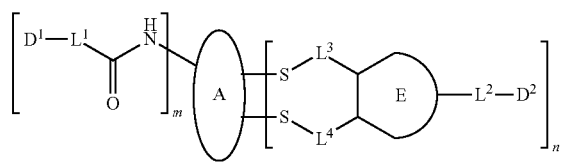

(I)

or a pharmaceutically acceptable salt thereof, wherein:
A is a targeting moiety;
each $D^1$ is independently selected, where each $D^1$ is an active agent;
each $L^1$ is independently a linker including at least one N (nitrogen) atom;
each $D^2$ is independently selected, where each $D^2$ includes an active agent;
each $L^2$ is independently a linker;
the E-component is an optionally substituted heteroaryl or an optionally substituted heterocyclyl;
each $L^3$ is an optionally substituted $C_1$-$C_6$ alkyl, or $L^3$ may be null, when $L^3$ is null the sulfur is directly connected to the E-component; and each $L^4$ is an optionally substituted $C_1$-$C_6$ alkyl, or $L^4$ is null, when $L^4$ is null the sulfur is directly connected to the E-component;
m is 1, 2, 3, 4, 5, 6, 7, 8, 9, or 10; and
n is 1, 2, 3, 4, 5, 6, 7, 8, 9, or 10.

Preferably, the E-component includes a fragment selected from the group consisting of:

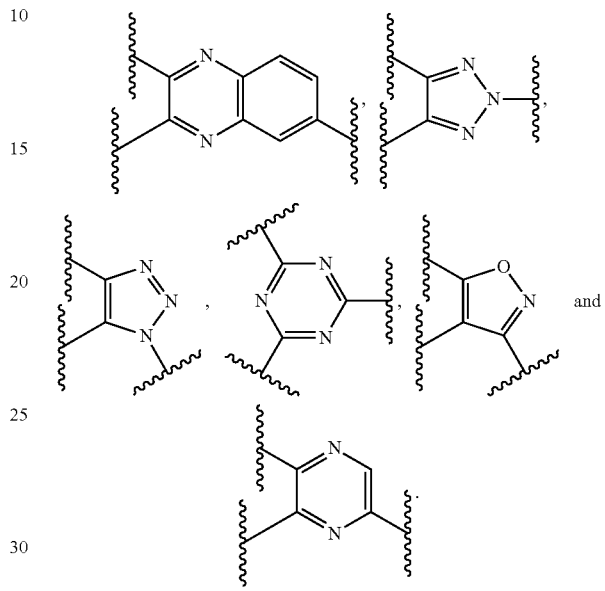

$L^3$ is —(CH$_2$)—; and $L^4$ is —(CH$_2$)—. $L^3$ is null; and $L^4$ is null.

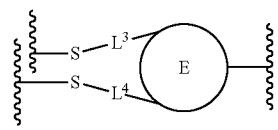

is:

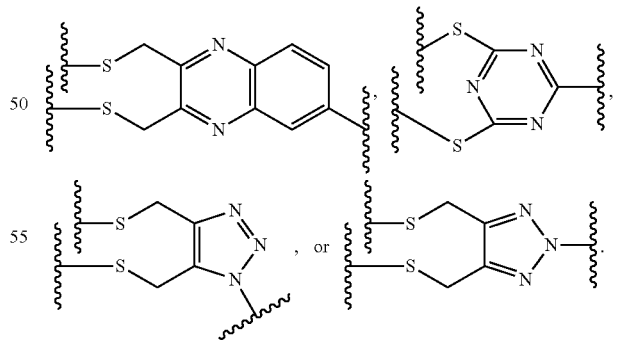

$L^1$ includes —(CH$_2$)$_n$— where n may be 1, 2, 3, 4, 5, 6, 7, 8, 9, or 10. In some embodiments, $L^1$ includes —(CH$_2$CH$_2$O)$_n$— where n may be 1, 2, 3, 4, 5, 6, 7, 8, 9, or 10. In some embodiments, $L^1$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, $L^1$ includes peptide, oligosaccharide, —(CH$_2$)$_n$—, —(CH$_2$CH$_2$O)$_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, or combinations thereof. Preferably, L$^1$ is selected from the group consisting of —(CH$_2$)$_n$—, —(CH$_2$CH$_2$O)$_n$— wherein n is an integer from 1-10, a peptide,

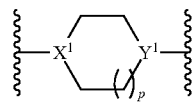

wherein X$^1$ is N (nitrogen) or CH; Y$^1$ is N (nitrogen), or CH; and p is 0, 1, or 2,

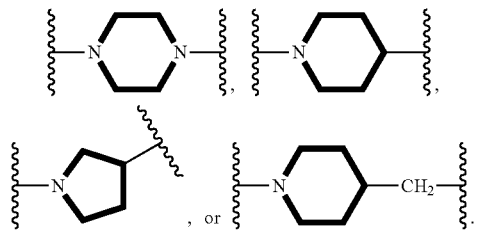

L$^2$ includes —(CH$_2$)$_n$— where n may be 1, 2, 3, 4, 5, 6, 7, 8, 9, or 10. In some embodiments, L$^2$ includes —(CH$_2$CH$_2$O)$_n$— where n is 1, 2, 3, 4, 5, 6, 7, 8, 9, or 10. In some embodiments, L$^2$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, L$^2$ includes peptide, oligosaccharide, —(CH$_2$)$_n$—, —(CH$_2$CH$_2$O)$_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, or combinations thereof. In some embodiments, L$^2$ includes a noncleavable unit. In some embodiments, the noncleavable unit includes —(CH$_2$)$_n$— where n may be 1, 2, 3, 4, 5, 6, 7, 8, 9, or 10. In some embodiments, the noncleavable unit includes —(CH$_2$CH$_2$O)$_n$— where n may be 1, 2, 3, 4, 5, 6, 7, 8, 9, or 10. In some embodiments, L$^2$ includes a cleavable unit. Preferably, the cleavable unit comprises a peptide.

The A component is an antibody (mAB) or fragment thereof. Alternatively, the A component comprises a Cys engineered antibody. In some embodiments, the A component comprises an antibody of which at least one pair of the interheavy chain disulfide bond was eliminated. In some embodiments, the A component comprises at least one modified L-Alanine residue. In some embodiments, the A component comprises at least two modified L-Alanine residues. In some embodiments, at least one L$^2$ includes —(CH$_2$)$_n$— where n may be 1, 2, 3, 4, 5, 6, 7, 8, 9, or 10. In some embodiments, at least one L$^2$ includes —(CH$_2$CH$_2$O)$_n$— where n may be 1, 2, 3, 4, 5, 6, 7, 8, 9, or 10. In some embodiments, at least one L$^2$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB or combinations thereof.

Alternatively, the A component comprises at least two modified L-Alanine residues. In some embodiments, at least one L$^2$ includes —(CH$_2$)$_n$— where n may be 1, 2, 3, 4, 5, 6, 7, 8, 9, or 10. In some embodiments, at least one L$^2$ includes —(CH$_2$CH$_2$O)$_n$— where n may be 1, 2, 3, 4, 5, 6, 7, 8, 9, or 10. In some embodiments, at least one L$^2$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, at least one L$^2$ includes a peptide, an oligosaccharide, —(CH$_2$)$_n$—, —(CH$_2$CH$_2$O)$_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB or combinations thereof.

A comprises at least one modified n-butyl L-a-amino acid. In some embodiments, A comprises at least one modified L-Lysine residue is from an L-Lysine residue of a peptide before conjugation. In some embodiments, A-NH together comprise at least one modified L-Lysine residue. In some embodiments, the terminal nitrogen of the side chain of an L-Lysine residue of a peptide before conjugation provides the NH of A-NH. In some embodiments, A comprises the —(CH$_2$)$_4$— of the side chain of an L-Lysine residue of a peptide before conjugation that provides the at least one A-NH. In some embodiments, A comprises a modified n-butyl a-amino acid residue.

DETAILED DESCRIPTION

Figure 1:
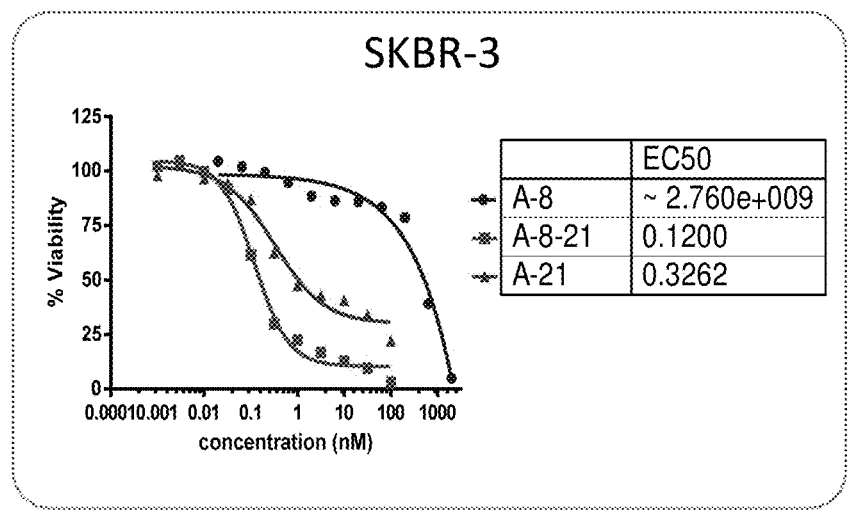
FIG. 1 shows anti-Her-2 (A) dual conjugates (K-lock+C-lock) induces enhanced antiproliferative effect in breast cancer cell lines, compared to either single K-lock or C-lock conjugates. A, SKBR-3 (HER2 3+), B, HCC1954 (HER2 3+), C, MCF-7 (HER2+/−), were all treated with either single conjugates or dual conjugates for 3 d. 1050 was determined for the concentration that showed 50% inhibition of cell growth.
Figure 1:
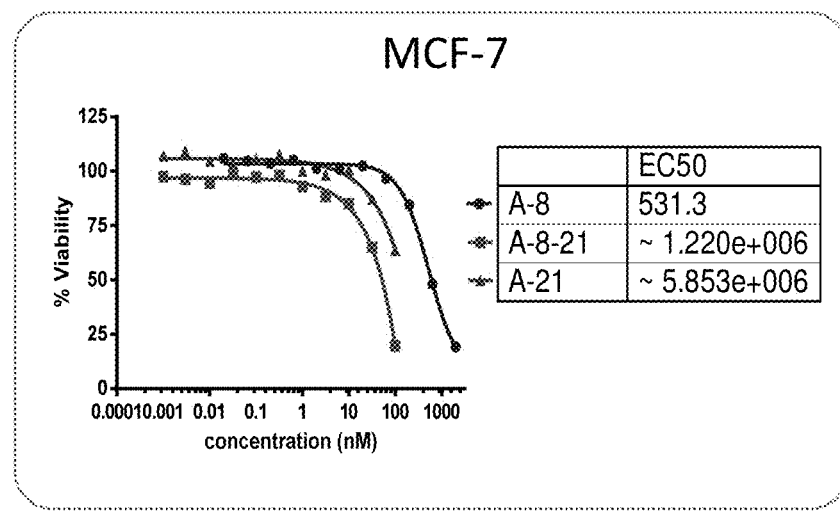
Figure 1:
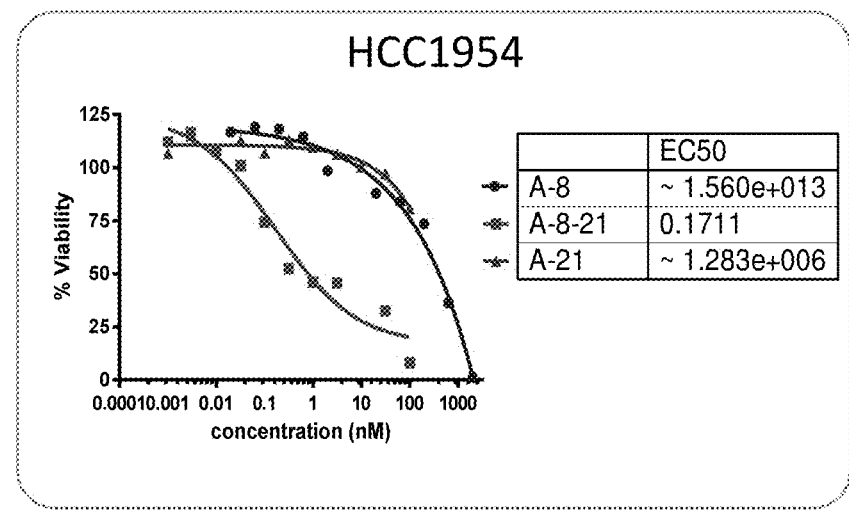

The present disclosure provides a genus of dual-drug improved ADC's (antibody drug conjugates) that comprise two different drugs (D1 and D2), wherein the D1 conjugate is linked to a Lys residue of the targeting protein (preferably an antibody or fragment thereof) that is also called "K-Lock", and the D2 or second drug conjugate is linked to two nearby Cys residues on the targeting protein that is also called "C-Lock." The present disclosure fulfills a long-felt need in the art to be able to use a single targeting protein to deliver into a target cell (such as a cancer cell) two different drug payloads (D1 and D2).

Table 1 below shows structures of the K-lock conjugation and Table 2 below shows structures for C-Lock conjugation. The present disclosure is based on the ability to do both C-Lock and K-Lock with a single targeting protein.

TABLE 1

Structures of K lock (Lys conjugation) compounds

| Compound no | structure |
|---|---|
| 3 | 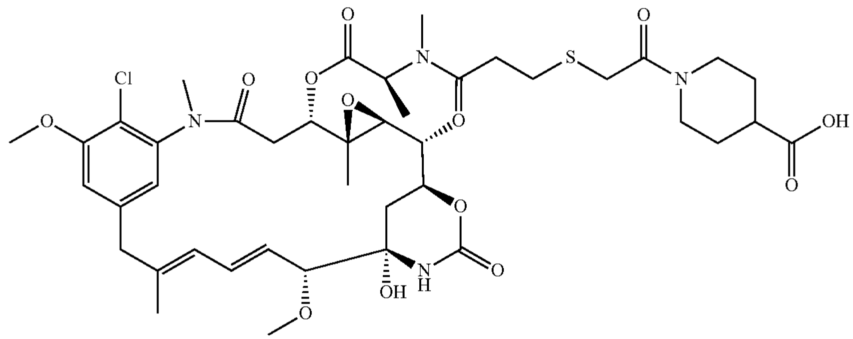 |
| 8 | 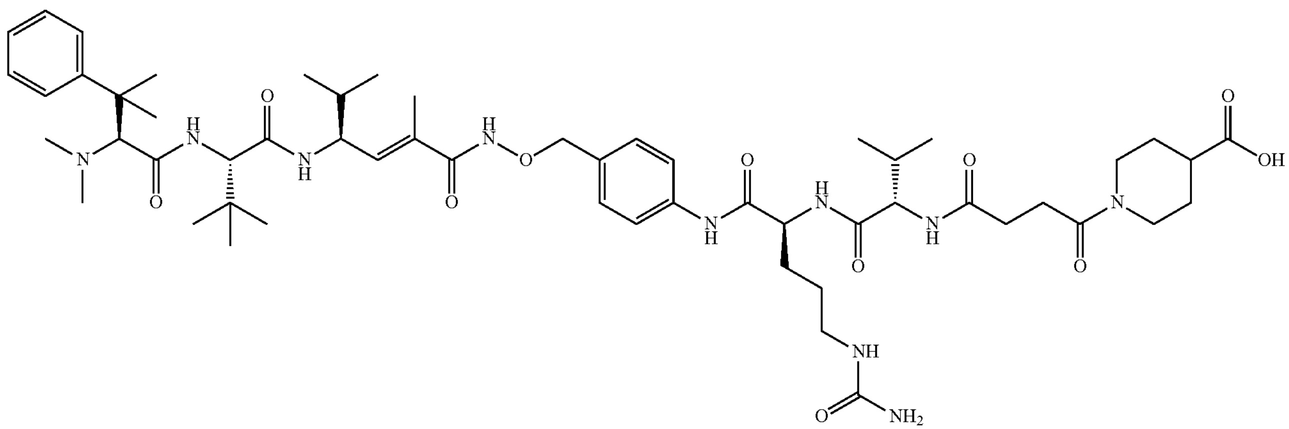 [SMILES: C/C(=C\[C@@H](NC(=O)[C@@H](NC(=O)[C@@H](N(C)C)C(C)(C)c1ccccc1)C(C)(C)C)C(C)C)C(=O)NOCc1ccc(NC(=O)[C@H](CCCNC(N)=O)NC(=O)[C@@H](NC(=O)CCC(=O)N2CCC(C(=O)O)CC2)C(C)C)cc1] |

TABLE 1-continued
Structures of K lock (Lys conjugation) compounds
| Compound no | structure |
|---|---|
| 9 | 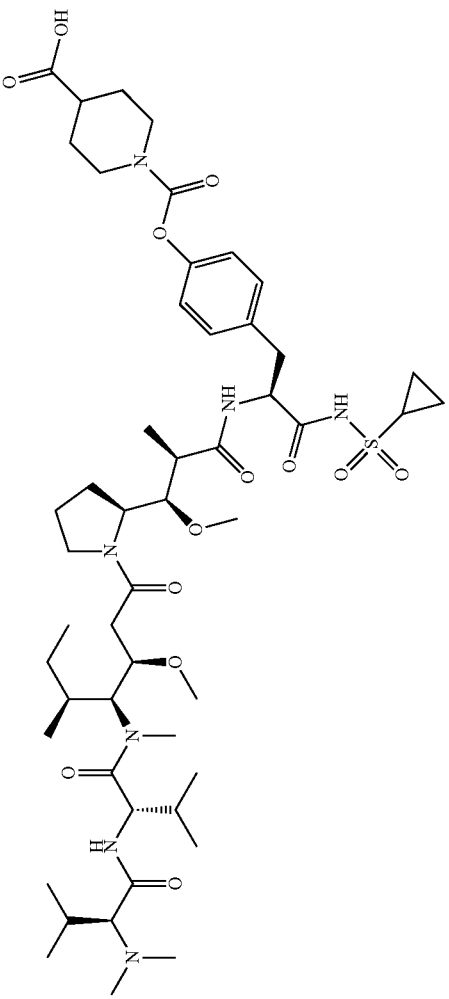 |
| 10 | 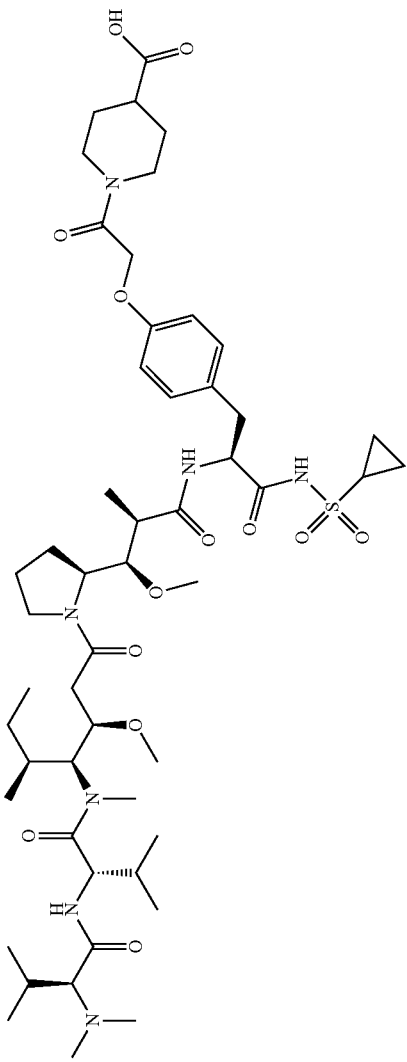 |

TABLE 1-continued

Structures of K lock (Lys conjugation) compounds

| Compound no | structure |
|---|---|
| 11 | 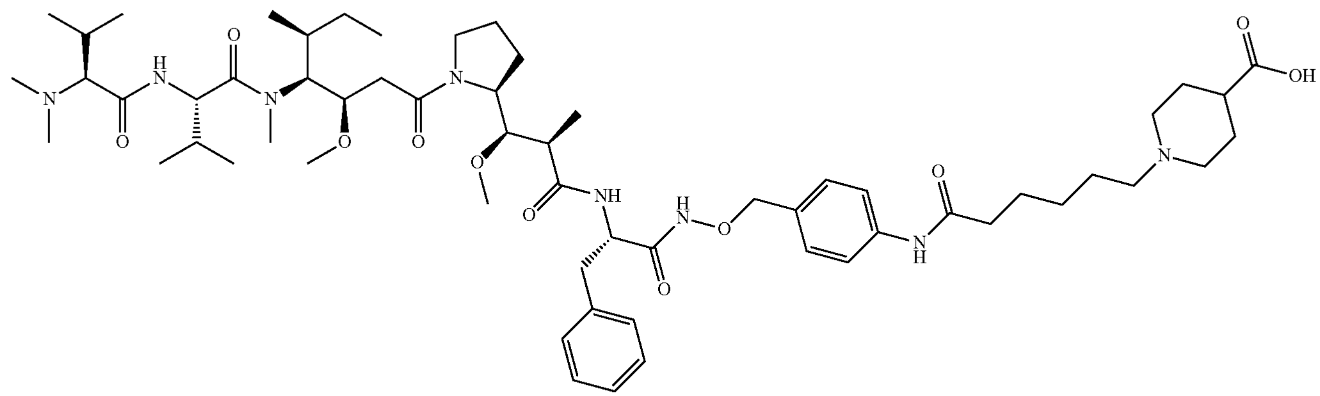 [SMILES: CC[C@H](C)[C@@H]([C@@H](CC(=O)N1CCC[C@H]1[C@H](OC)[C@@H](C)C(=O)N[C@@H](Cc1ccccc1)C(=O)NOCc1ccc(NC(=O)CCCCCN2CCC(C(=O)O)CC2)cc1)OC)N(C)C(=O)[C@@H](NC(=O)[C@H](C(C)C)N(C)C)C(C)C] |
| 12 | 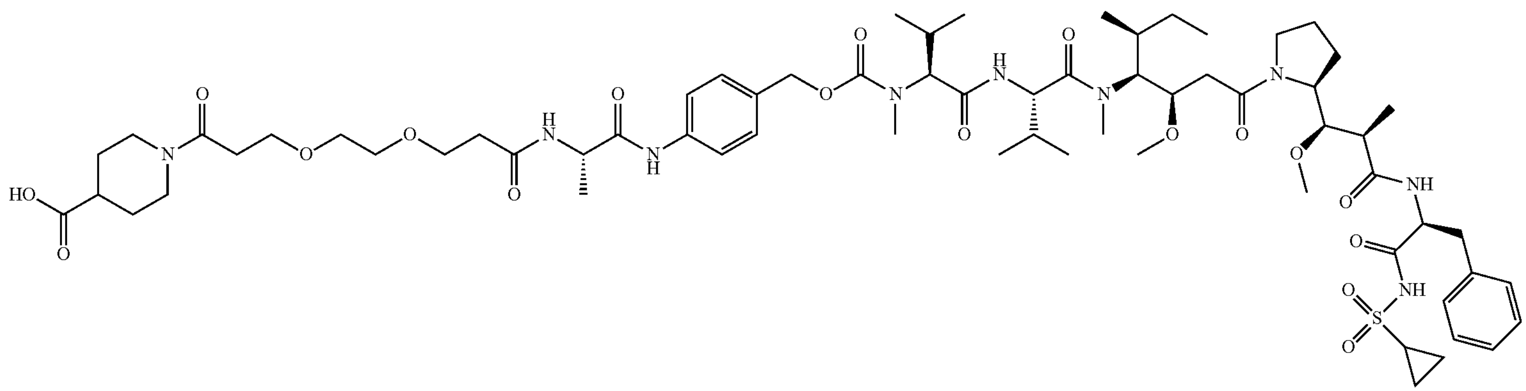 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)C1CC1)OC)N(C)C(=O)[C@@H](NC(=O)[C@H](C(C)C)N(C)C(=O)OCc1ccc(NC(=O)[C@H](C)NC(=O)CCOCCOCCC(=O)N2CCC(C(=O)O)CC2)cc1)C(C)C] |

TABLE 1-continued
Structures of K lock (Lys conjugation) compounds
| Compound no | structure |
|---|---|
| 13 | 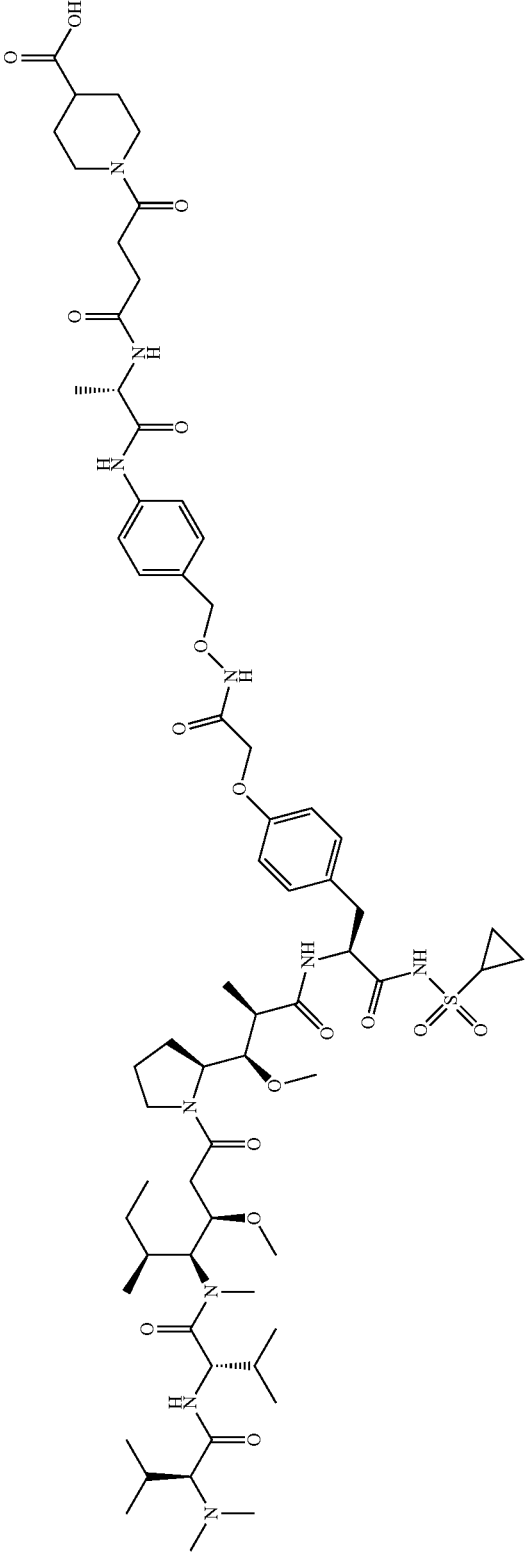 |
| 14 | 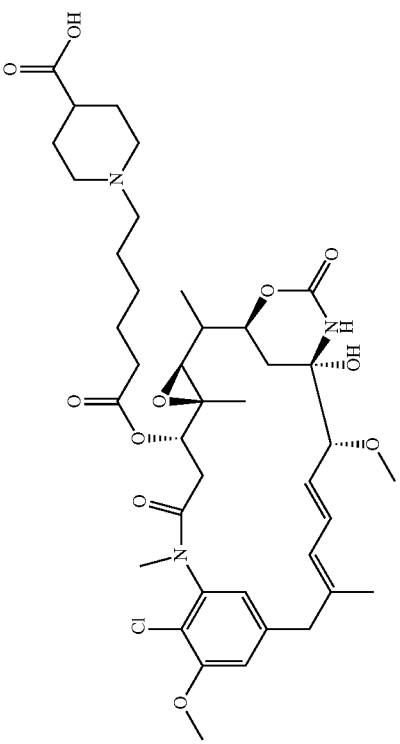 |

TABLE 2

Structures of C-lock (Cys conjugation) compounds

| Compound ID | Structure |
|---|---|
| 17 | 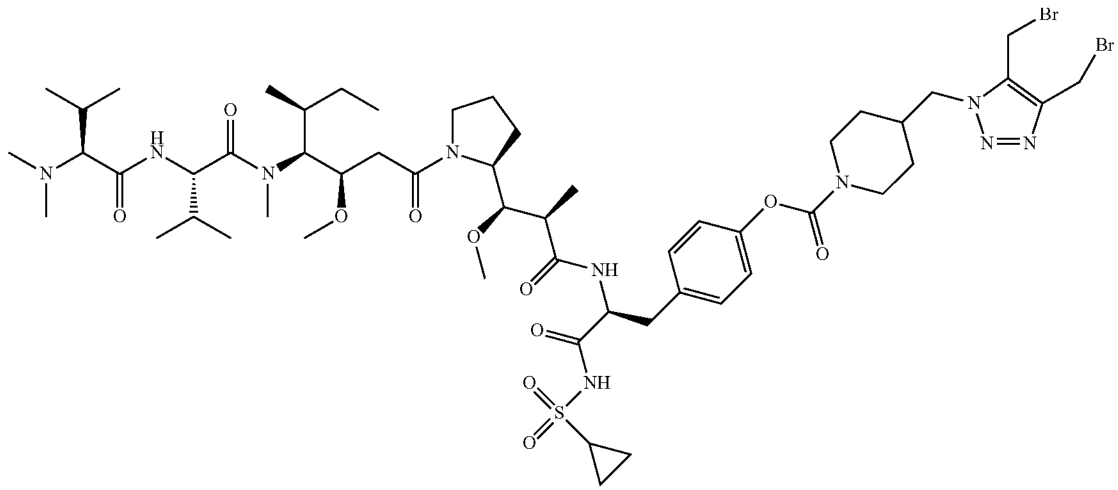 [SMILES: CC[C@H](C)[C@@H]([C@@H](CC(=O)N1CCC[C@H]1[C@H](OC)[C@@H](C)C(=O)N[C@@H](Cc1ccc(OC(=O)N2CCC(Cn3nnc(CBr)c3CBr)CC2)cc1)C(=O)NS(=O)(=O)C1CC1)OC)N(C)C(=O)[C@@H](NC(=O)[C@H](C(C)C)N(C)C)C(C)C] |
| 18 | 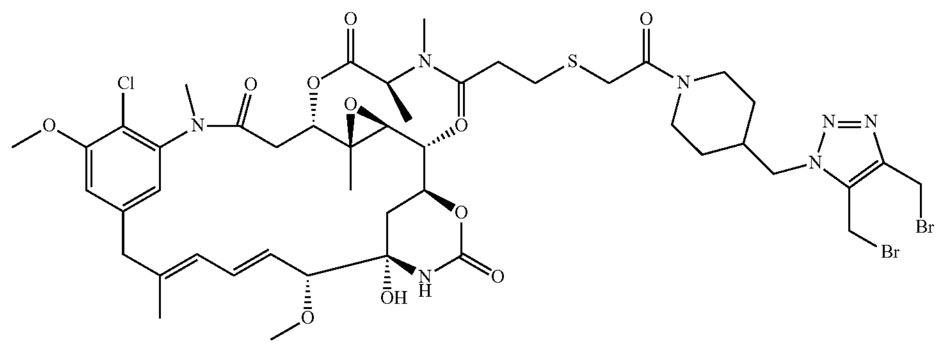 |

TABLE 2-continued

Structures of C-lock (Cys conjugation) compounds

| Compound ID | Structure |
|---|---|
| 21 | 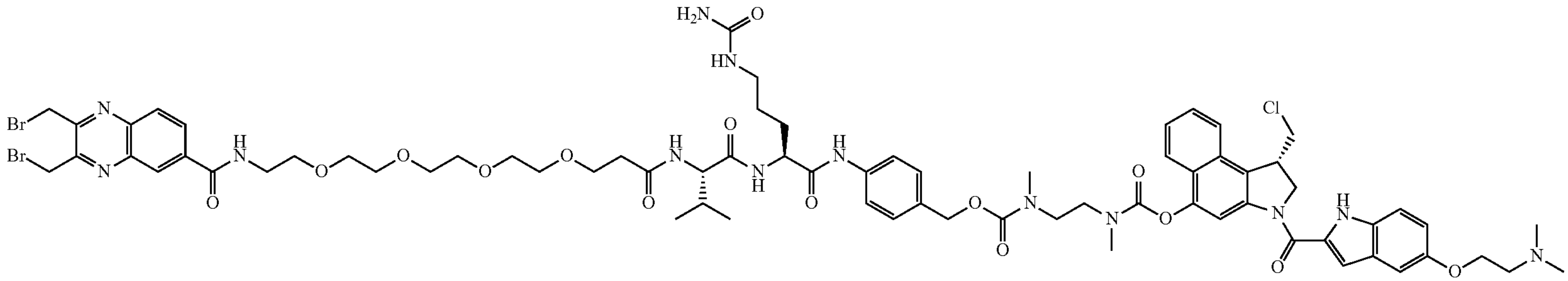 [SMILES: CC(C)[C@H](NC(=O)CCOCCOCCOCCOCCNC(=O)c1ccc2nc(CBr)c(CBr)nc2c1)C(=O)N[C@@H](CCCNC(N)=O)C(=O)Nc1ccc(COC(=O)N(C)CCN(C)C(=O)Oc2cc3c(c4ccccc24)[C@H](CCl)CN3C(=O)c2cc3cc(OCCN(C)C)ccc3[nH]2)cc1] |
| 26 | 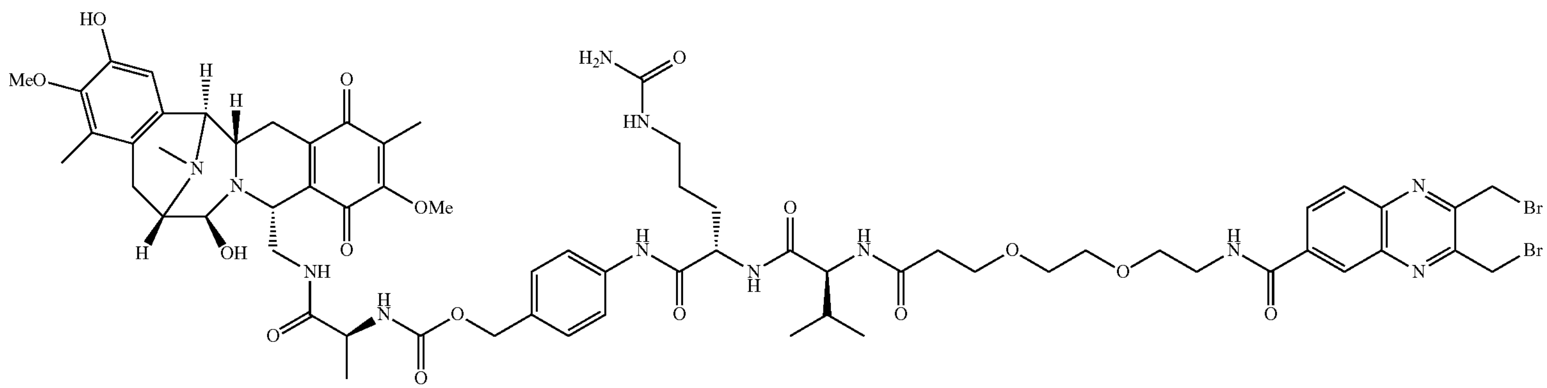 [SMILES: COC1=C(C)C(=O)C2=C(C1=O)[C@H](CNC(=O)[C@H](C)NC(=O)OCc1ccc(NC(=O)[C@H](CCCNC(N)=O)NC(=O)[C@@H](NC(=O)CCOCCOCCNC(=O)c3ccc4nc(CBr)c(CBr)nc4c3)C(C)C)cc1)N1[C@@H](O)[C@@H]3Cc4c(cc(O)c(OC)c4C)[C@@H]([C@@H]1C2)N3C] |

TABLE 2-continued
Structures of C-lock (Cys conjugation) compounds
| Compound ID | Structure |
|---|---|
| 27 | 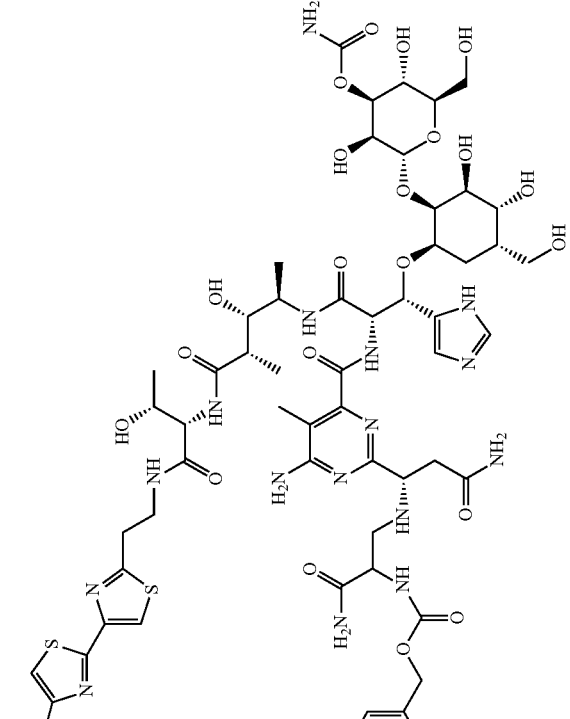 |

TABLE 2-continued

Structures of C-lock (Cys conjugation) compounds

| Compound ID | Structure |
|---|---|
| 32 | 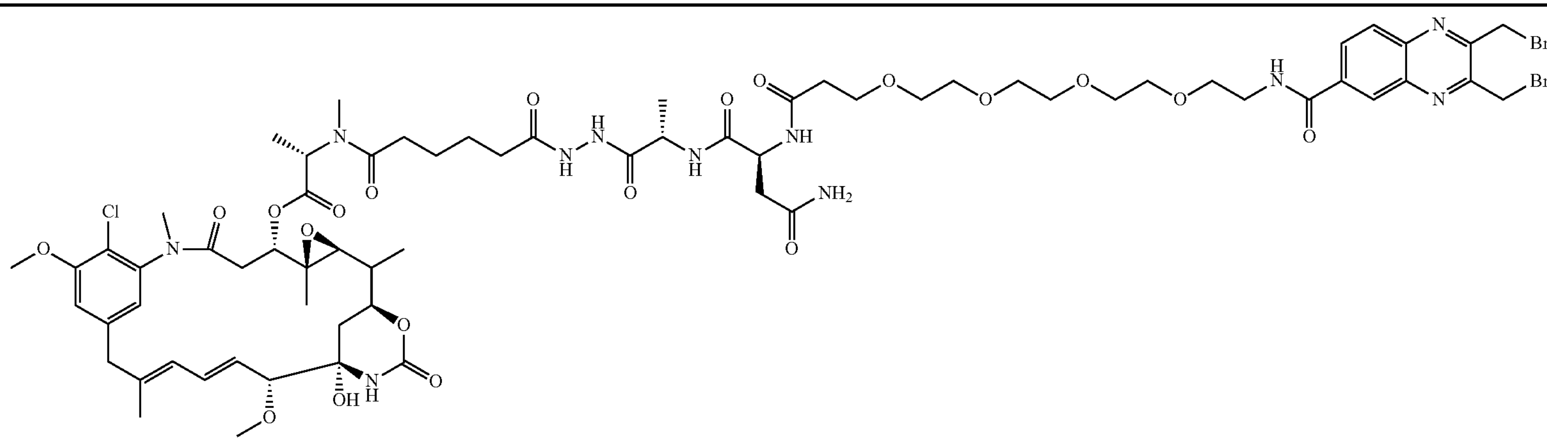 |
| 37 | 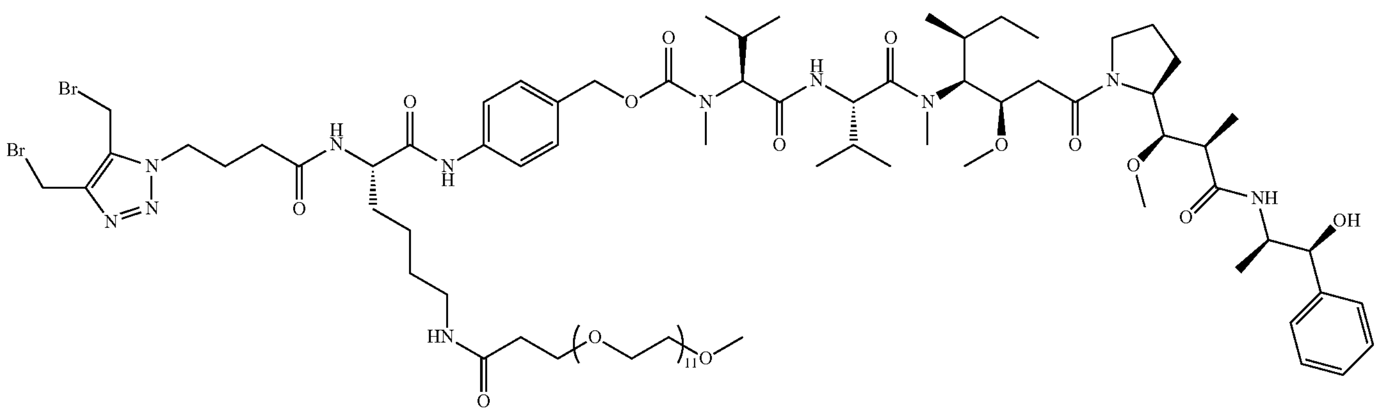 |

TABLE 2-continued

Structures of C-lock (Cys conjugation) compounds

| Compound ID | Structure |
|---|---|
| 38 | 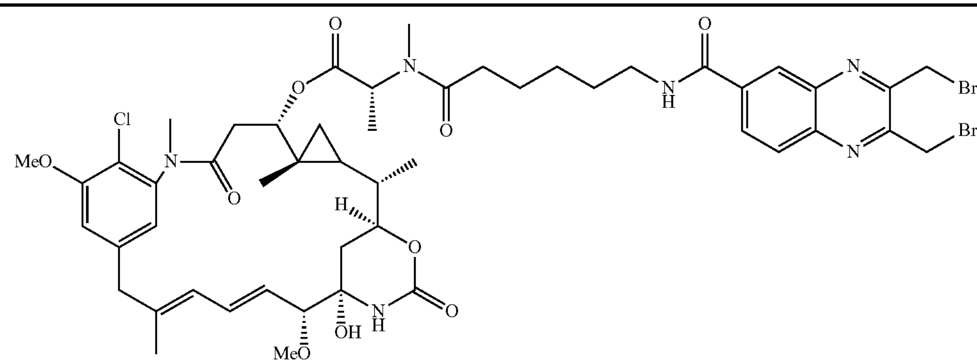 |
| 39 | 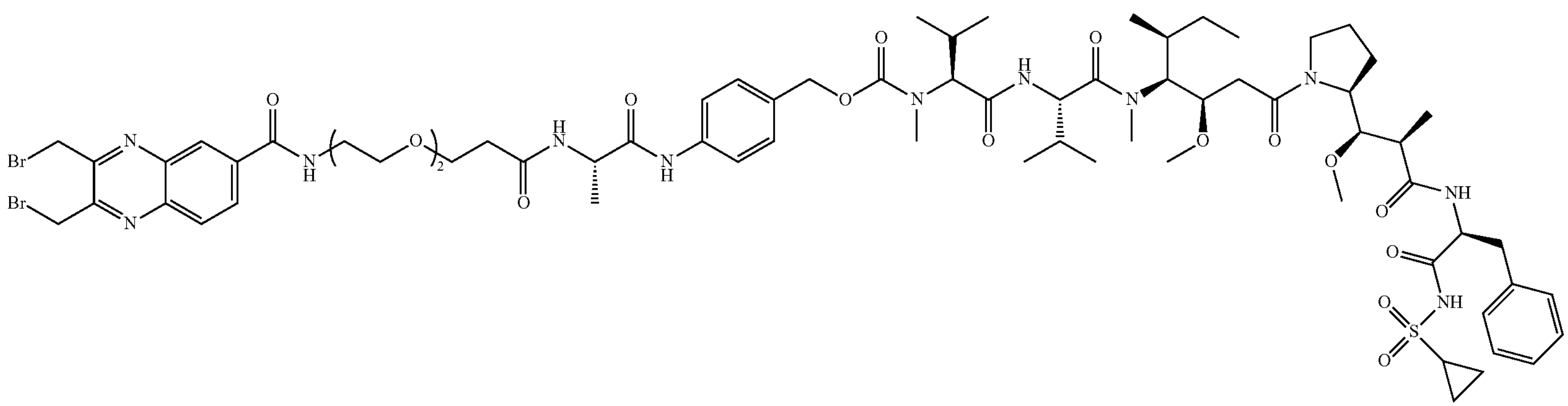 |

TABLE 2-continued
Structures of C-lock (Cys conjugation) compounds
| Compound ID | Structure |
|---|---|
| 40 | 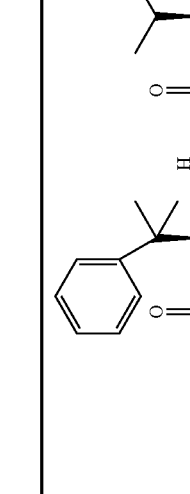 |

Table 3 below provides a list of those dual drug conjugates that are exemplified in this disclosure and shows both the D1 drug on the K-Lock side and the D2 drug on the C-Lock side.

TABLE 3

List of Dual conjugated (K lock and C lock) ADCs

| K lock (Lys) ID | C lock (Cys) ID | Dual conjugated ADC (Names used herein) |
|---|---|---|
| 9 | 32 | A*-9-32 |
| 9 | 18 | A-9-18 |
| 9 | 38 | A-9-38 |
| 9 | 40 | A-9-40 |
| 3 | 17 | A-3-17 |
| 3 | 40 | A-3-40 |
| 3 | 37 | A-3-37 |
| 11 | 21 | A-11-21 |
| 11 | 26 | A-12-26 |
| 12 | 38 | A-12-38 |
| 10 | 38 | A-10-38 |
| 13 | 38 | A-13-38 |
| 13 | 21 | A-13-21 |
| 8 | 21 | A-8-21 |
| 10 | 21 | A-10-21 |
| 14 | 21 | A-14-21 |
| 8 | 26 | A-8-26 |
| 14 | 21 | A-14-21 |
| 14 | 27 | A-14-27 |
| 10 | 26 | A-10-26 |
| 12 | 39 | A-12-39 |

*A is an anti-HER2 antibody

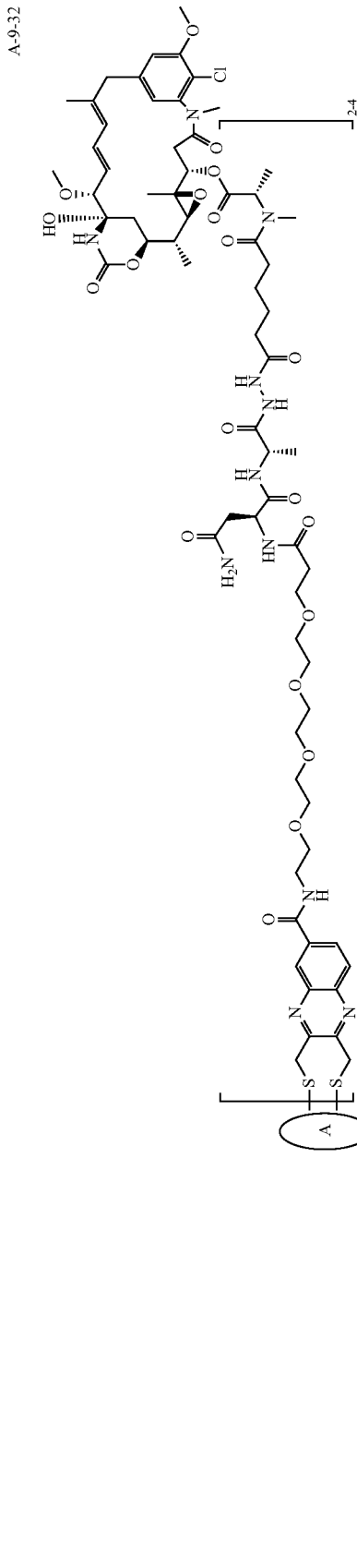
Structure of the Dual conjugated ADC

-continued
A-9-18
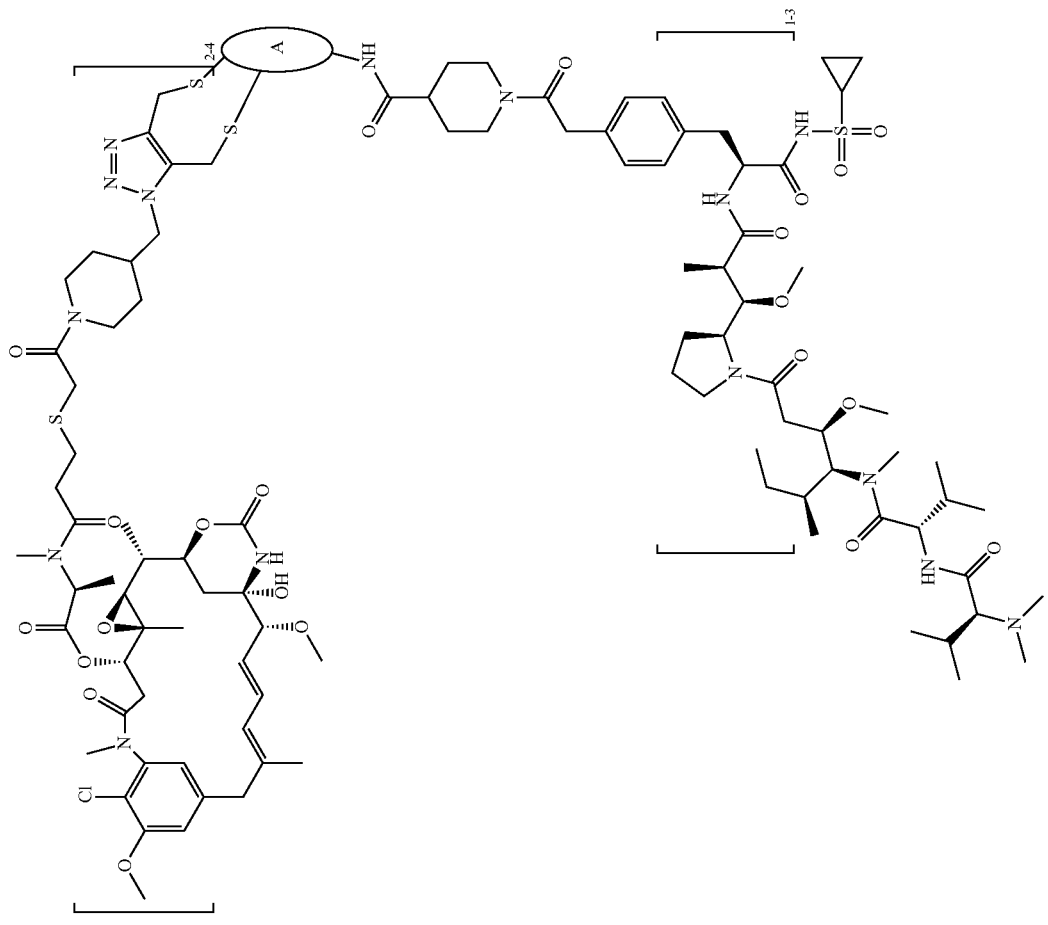
Structure of the Dual conjugated ADC

-continued
A-9-38
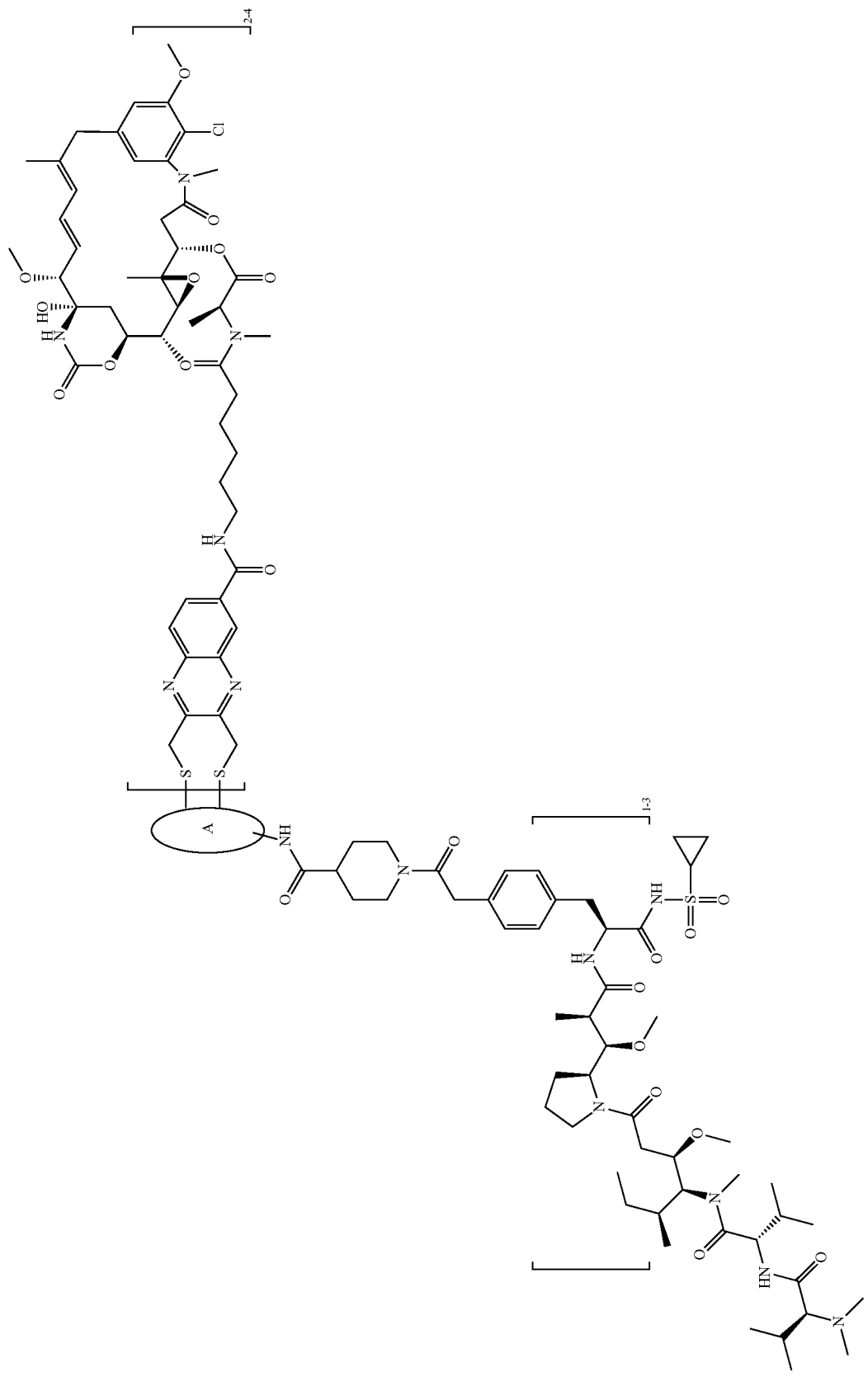
Structure of the Dual conjugated ADC

A-9-40
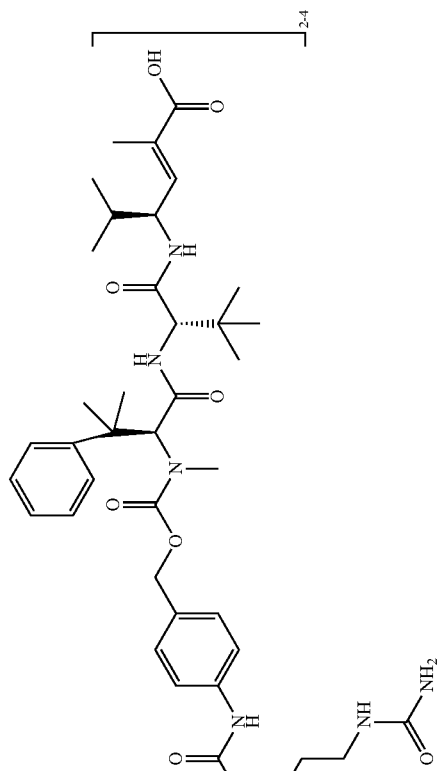
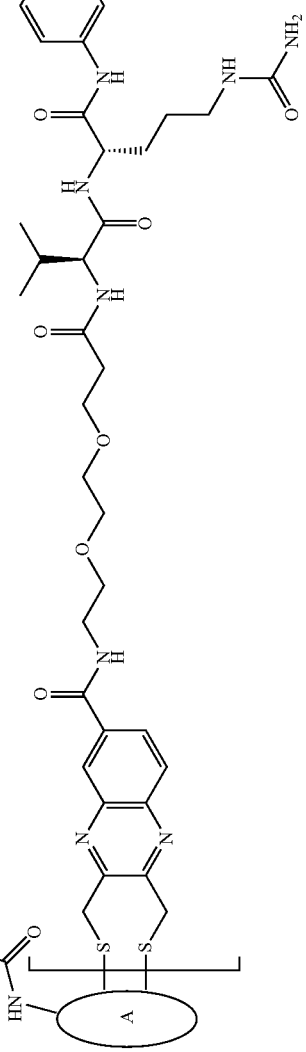
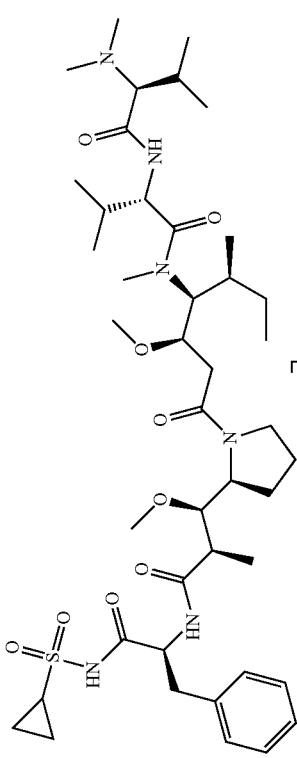
Structure of the Dual conjugated ADC

A-3-17
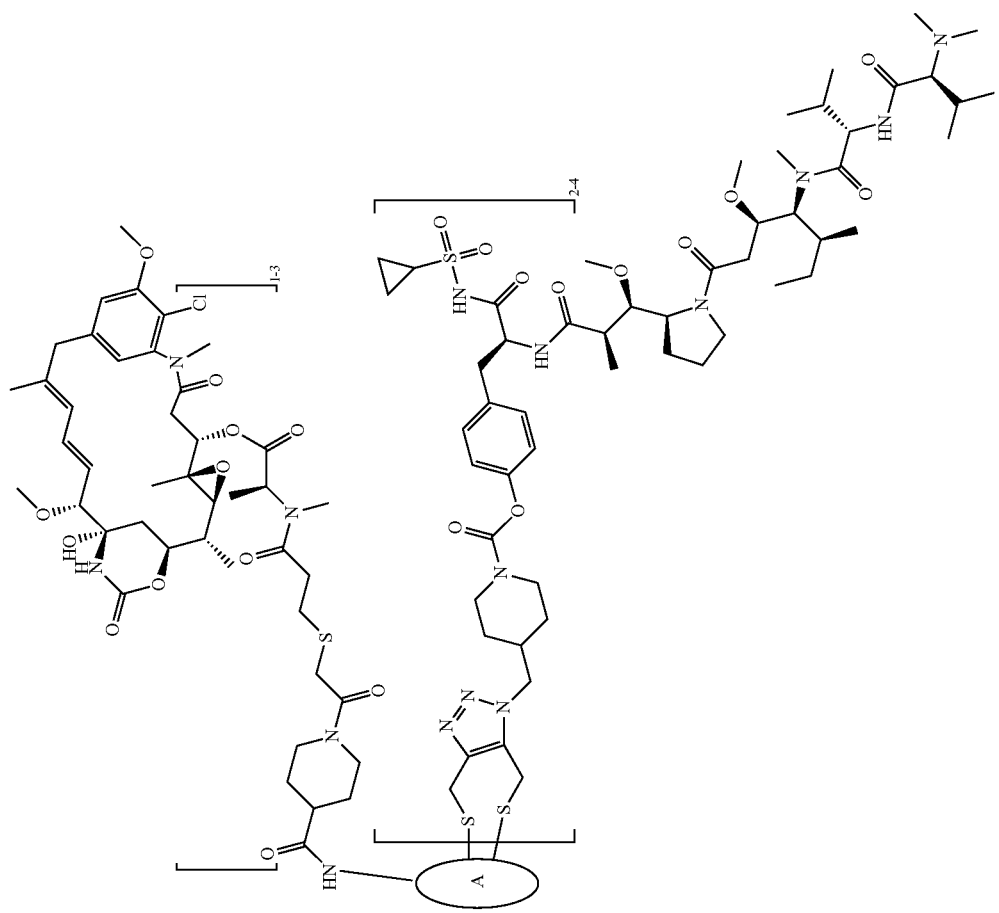
Structure of the Dual conjugated ADC

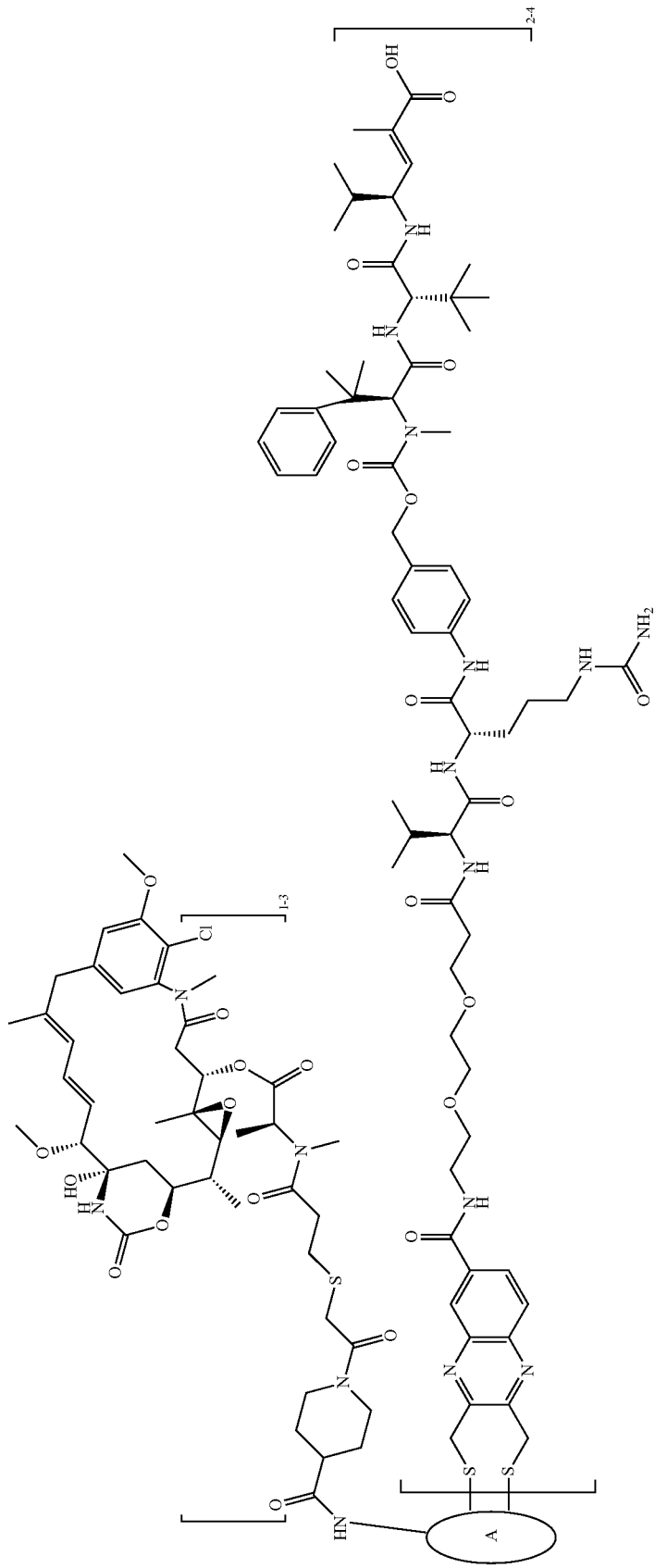
Structure of the Dual conjugated ADC

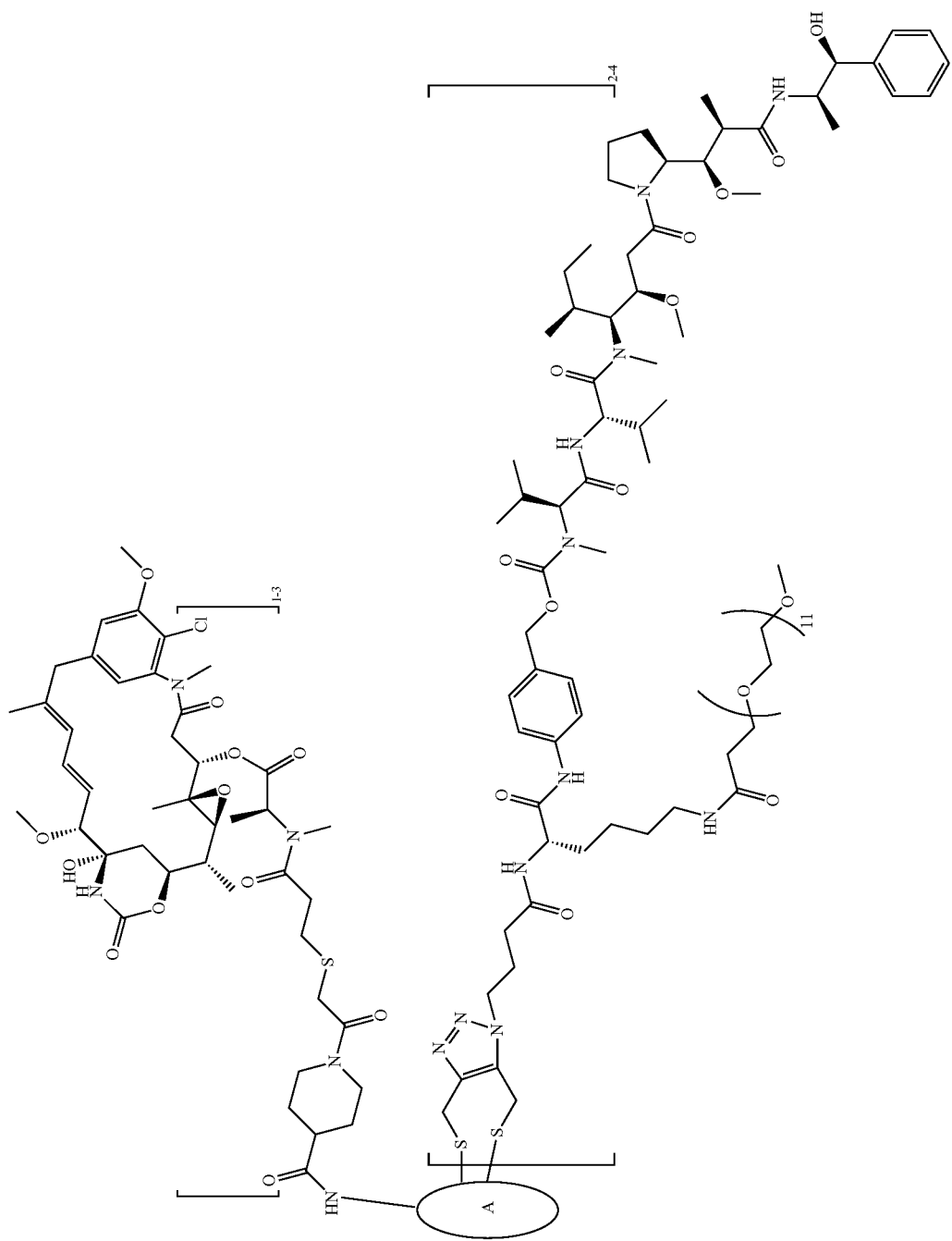

A-11-21
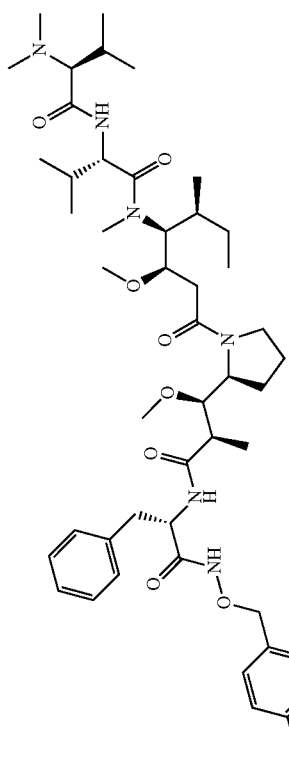
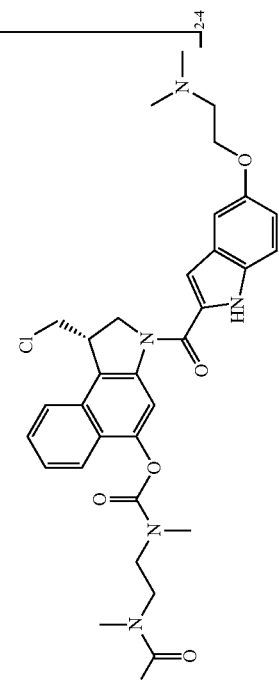
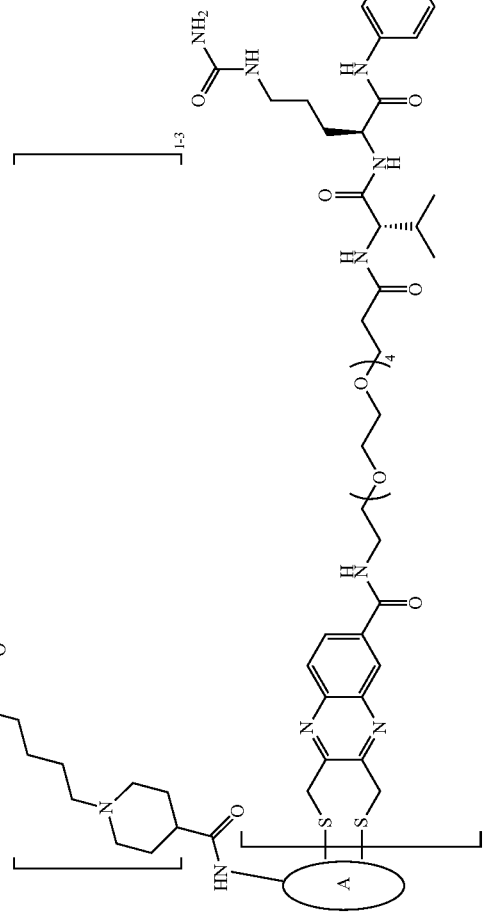
Structure of the Dual conjugated ADC

A-11-26
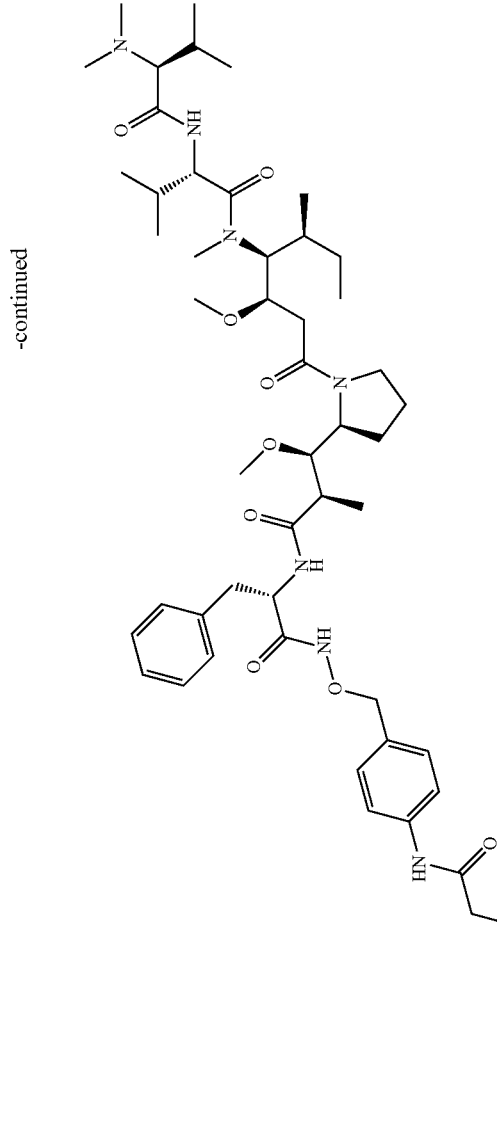
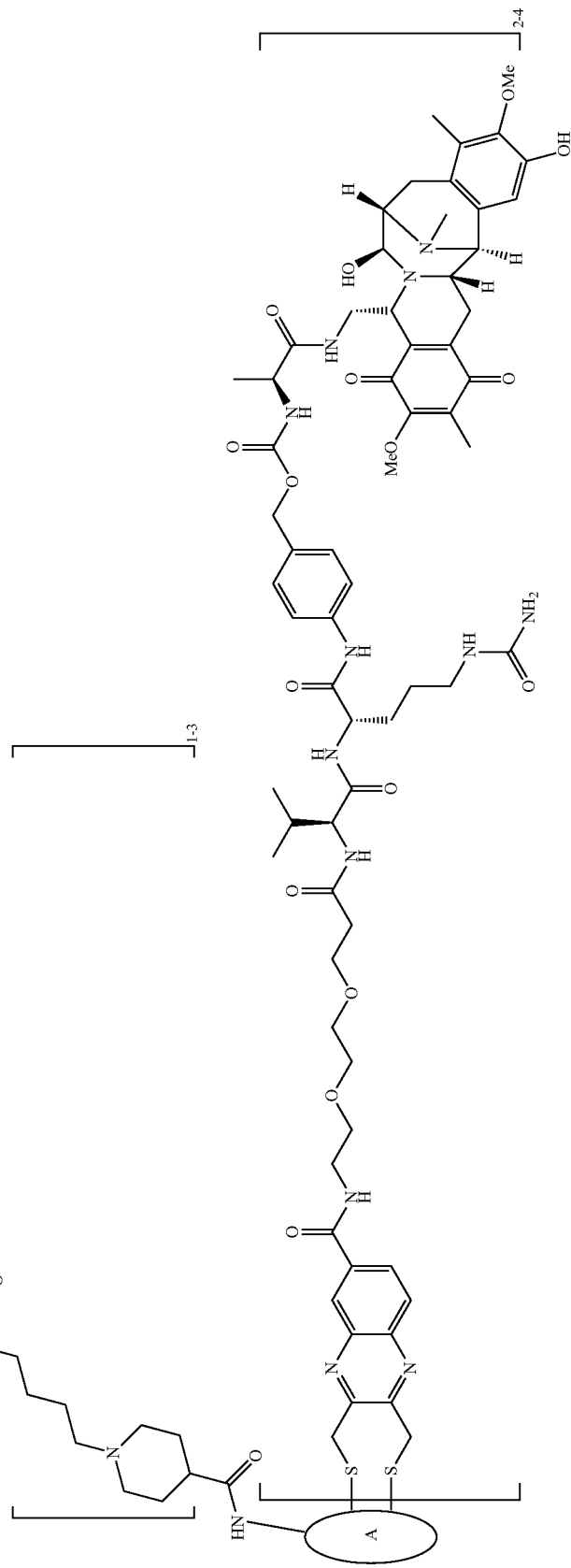
Structure of the Dual conjugated ADC

A-12-38
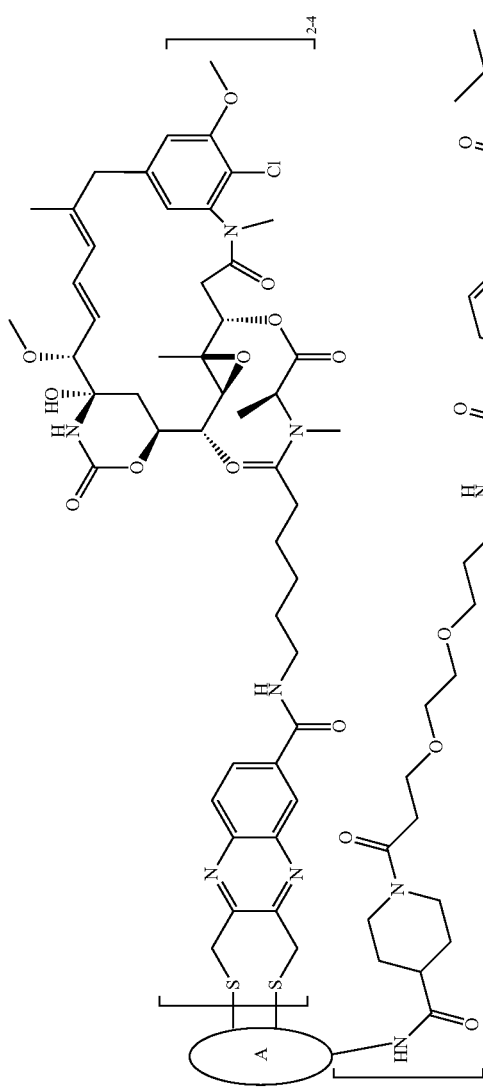
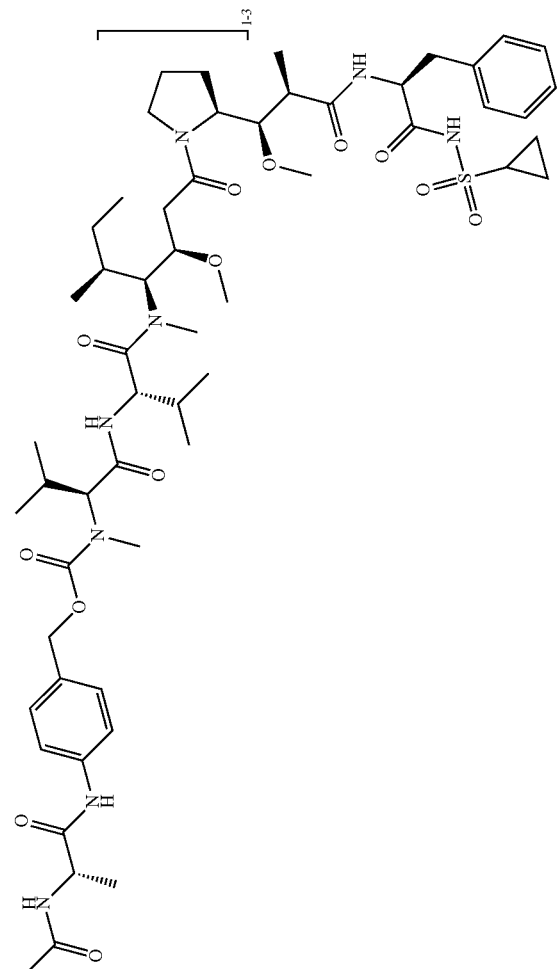
Structure of the Dual conjugated ADC

-continued
A-10-38
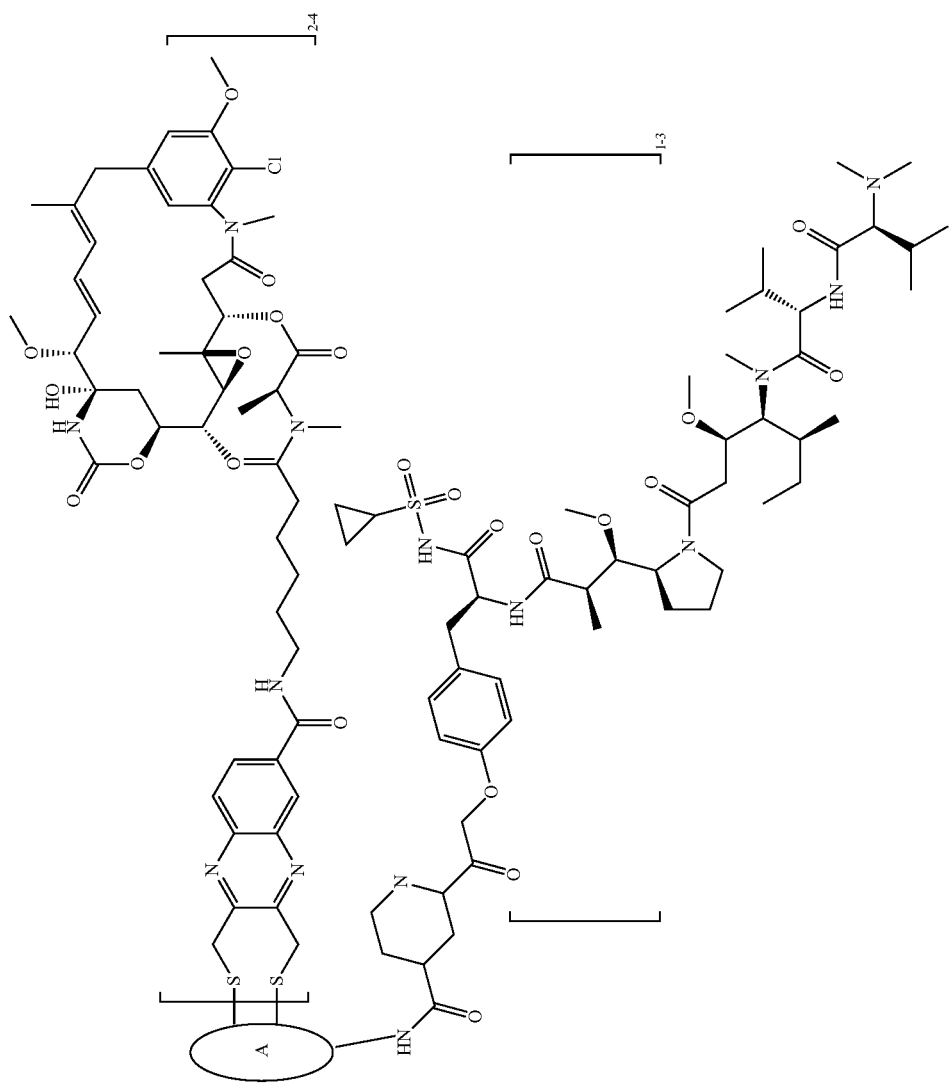
Structure of the Dual conjugated ADC

A-13-38
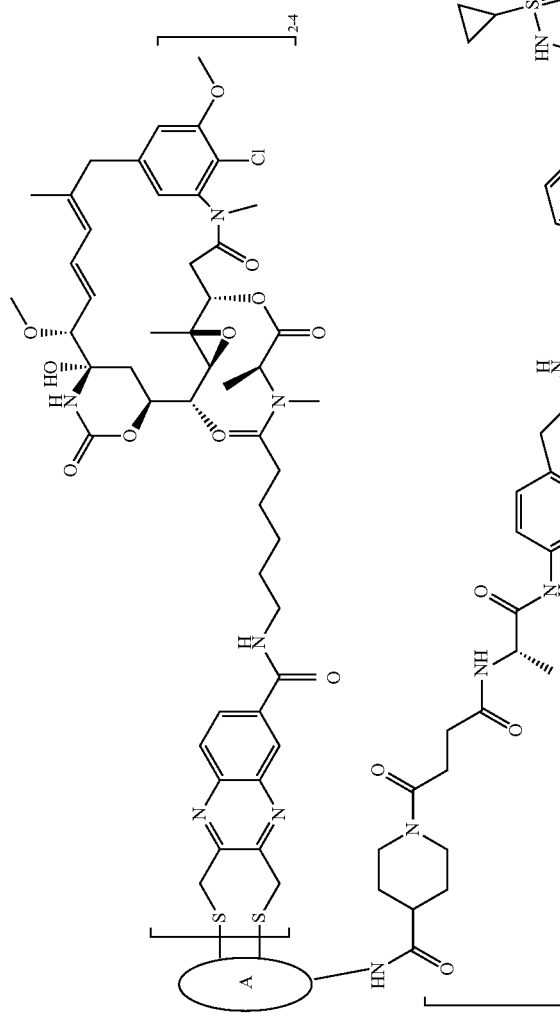
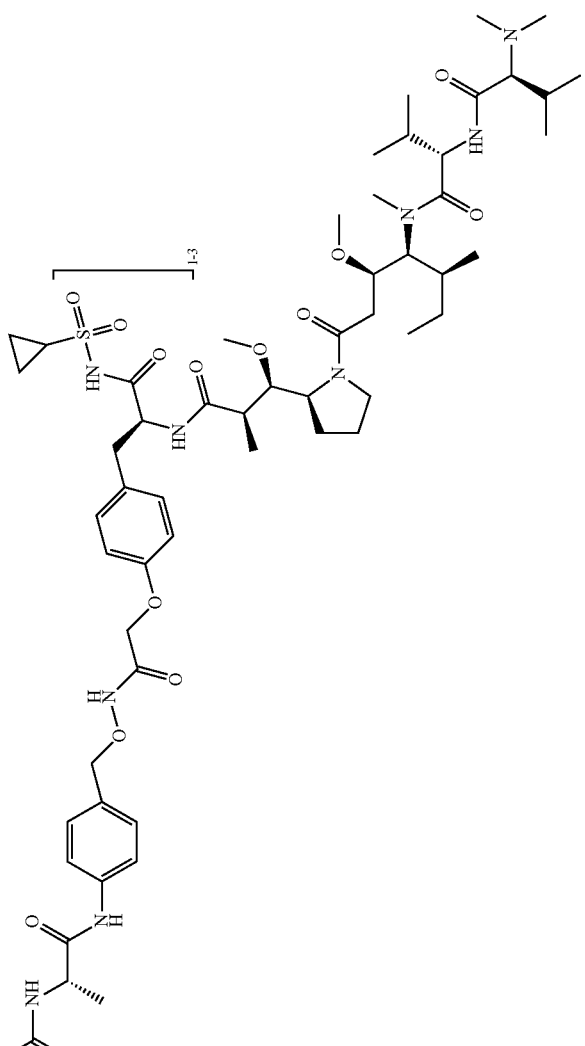
Structure of the Dual conjugated ADC

A-13-21
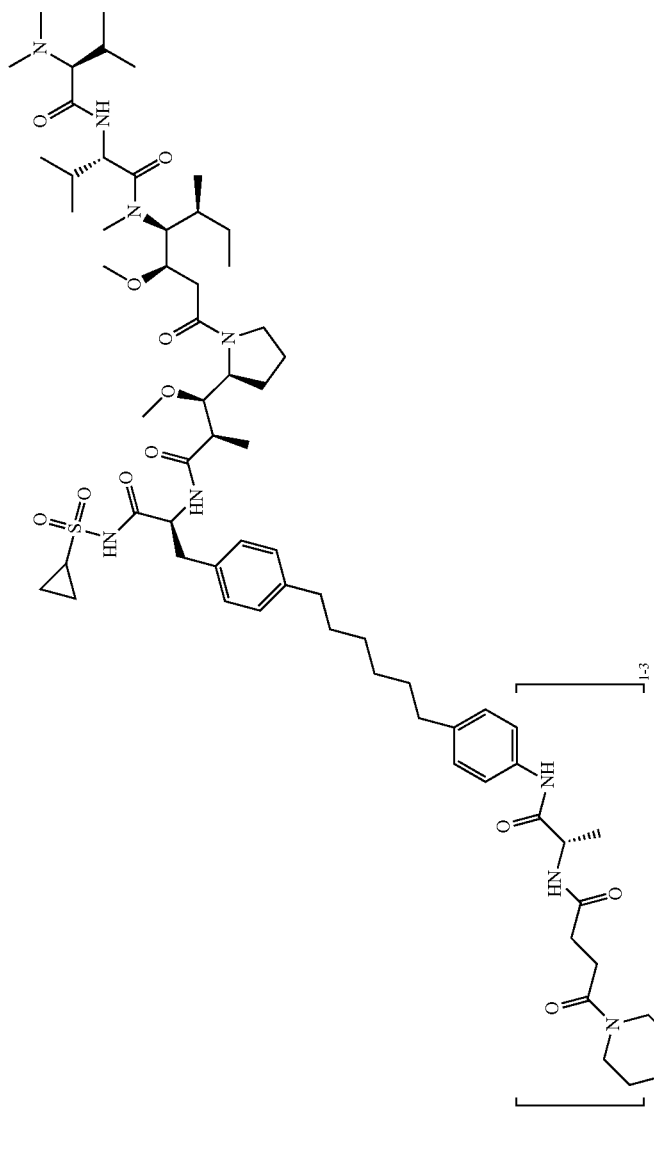
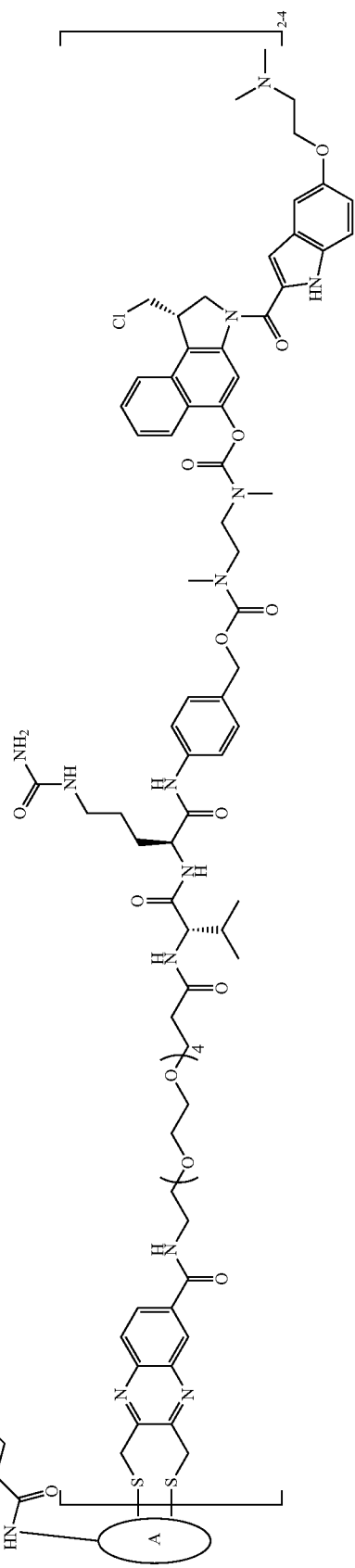
Structure of the Dual conjugated ADC

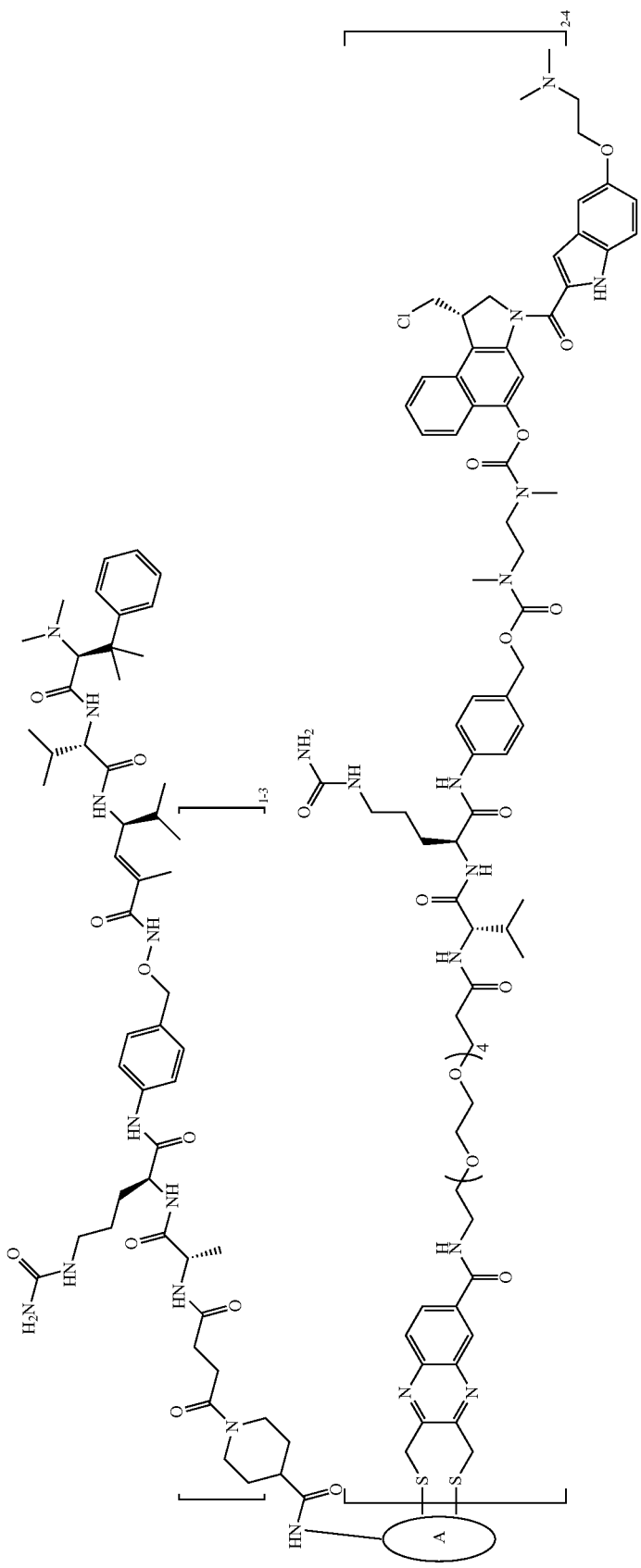
Structure of the Dual conjugated ADC

-continued
A-10-21
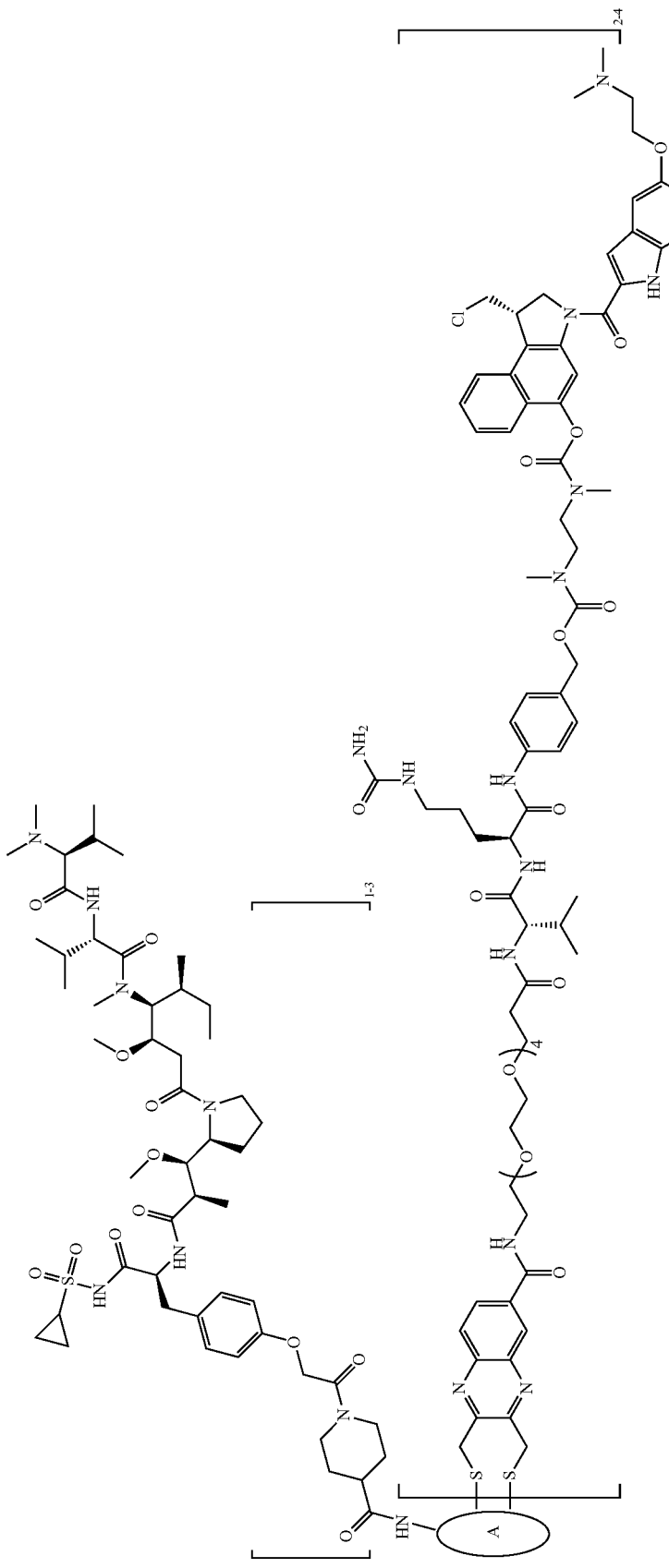
Structure of the Dual conjugated ADC

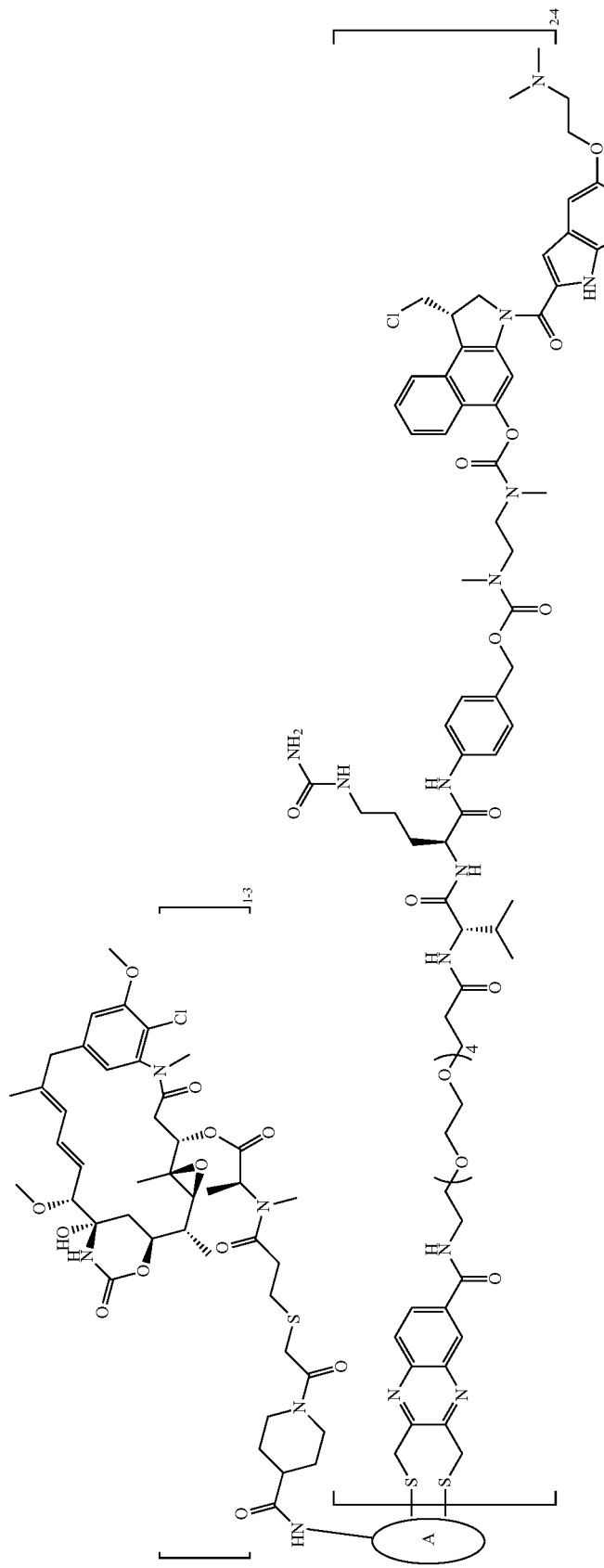
A-14-21
Structure of the Dual conjugated ADC

A-8-26
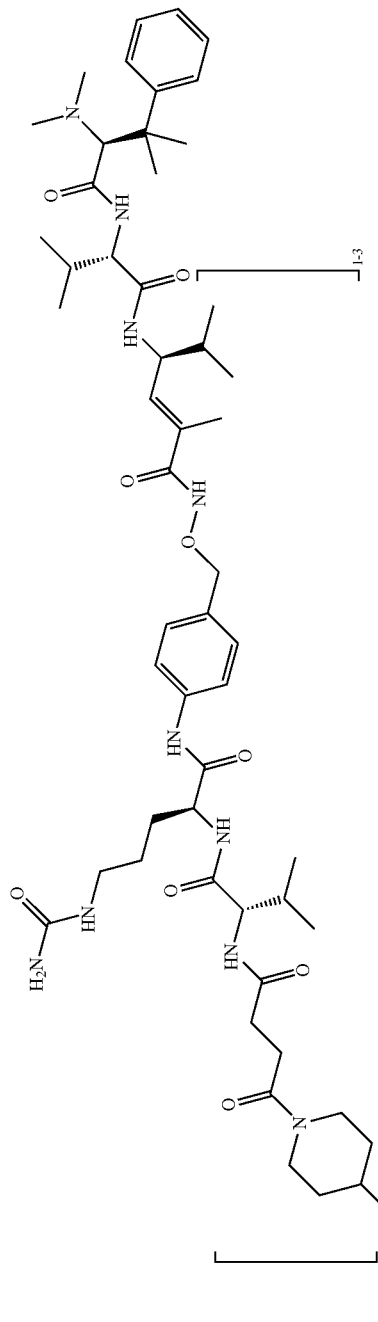
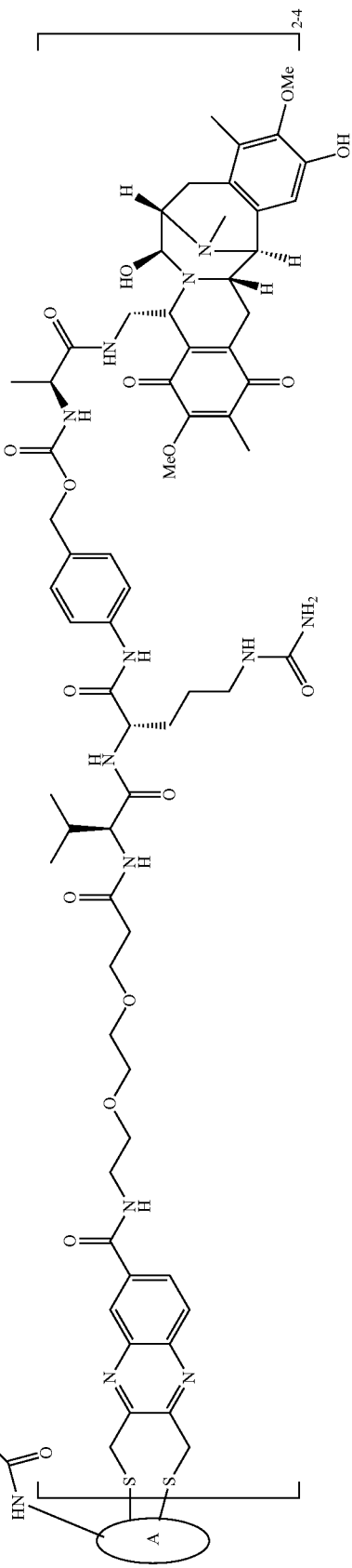
Structure of the Dual conjugated ADC

-continued
A-14-26
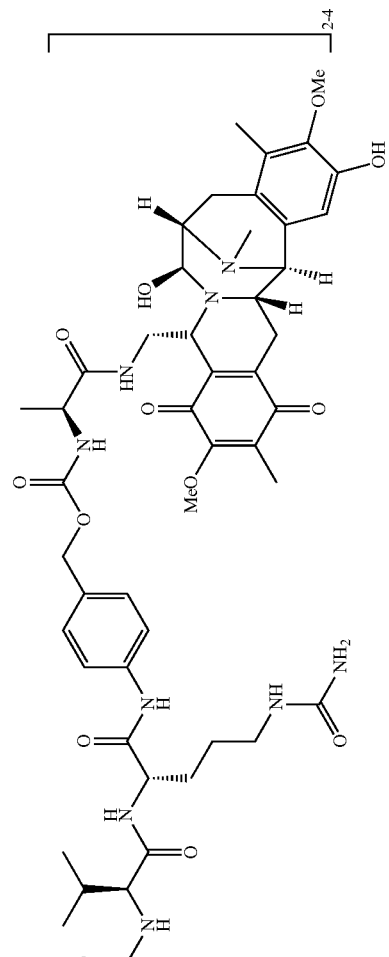
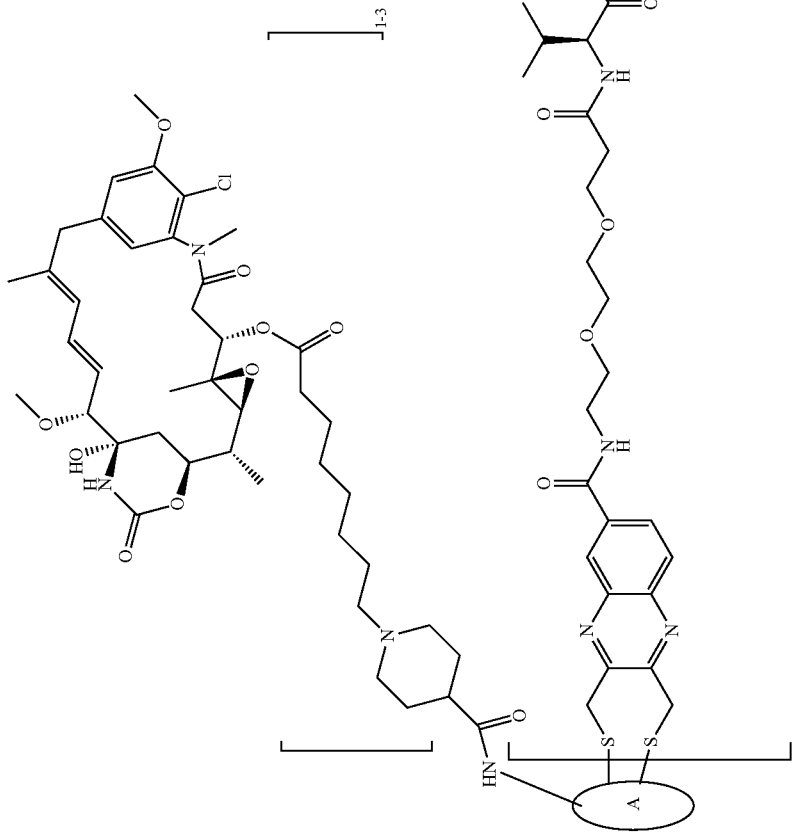
Structure of the Dual conjugated ADC

-continued
A-14-27
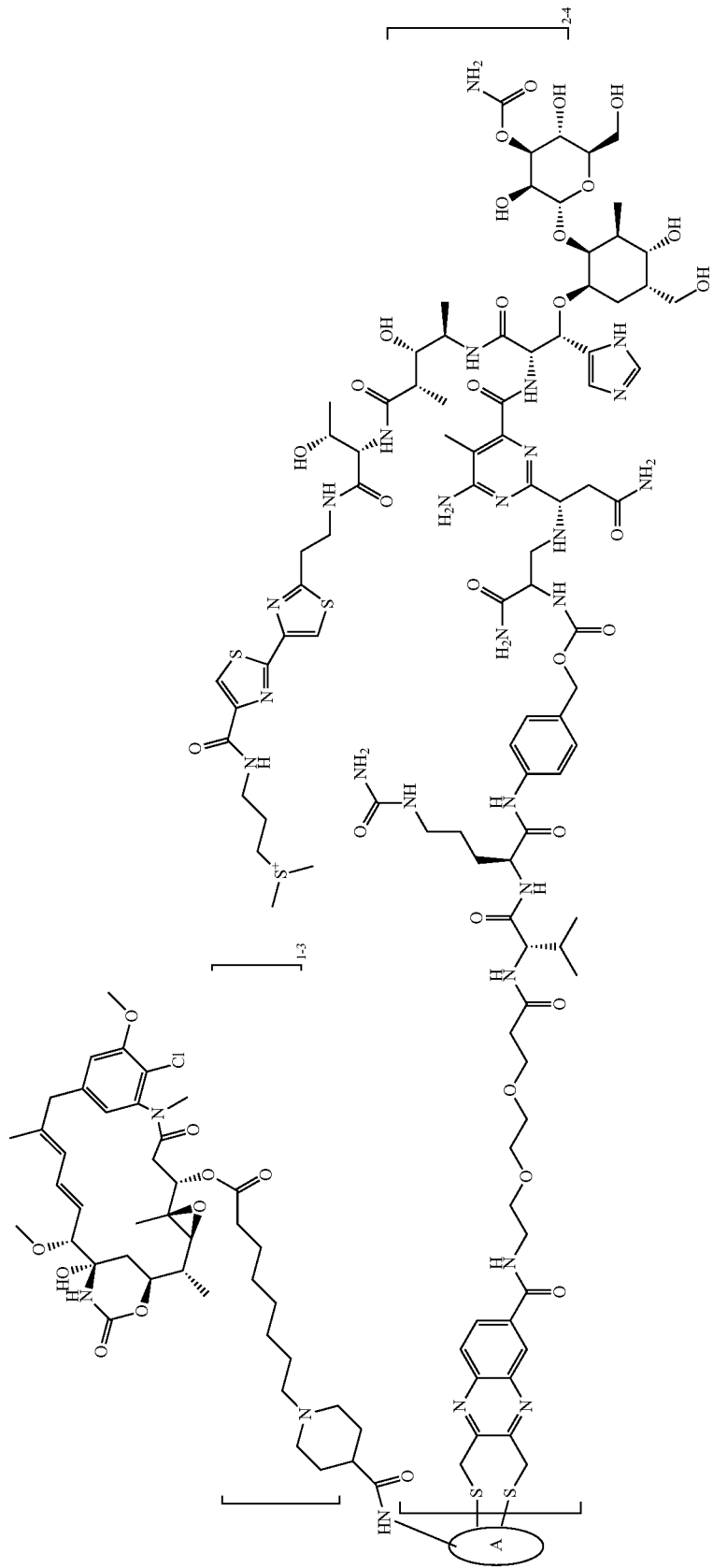
Structure of the Dual conjugated ADC

A-10-26
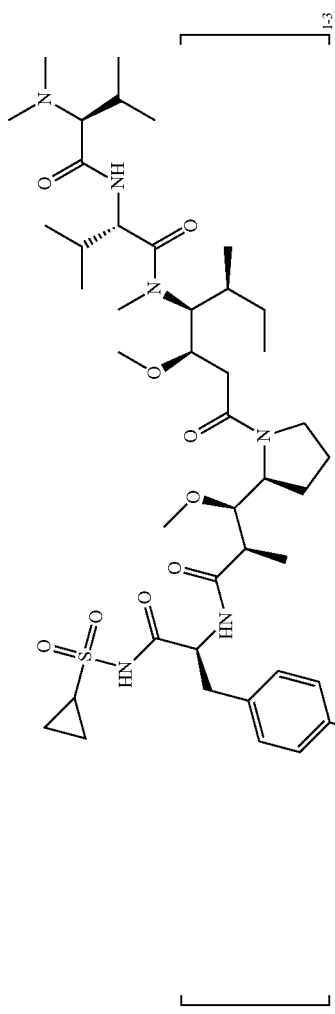
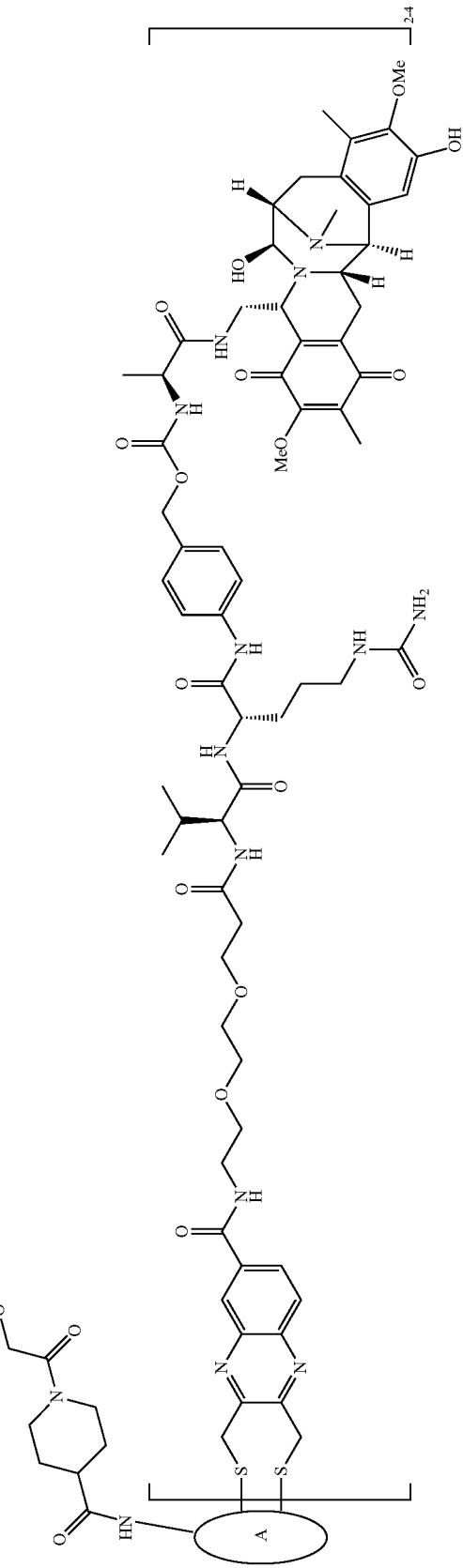
Structure of the Dual conjugated ADC

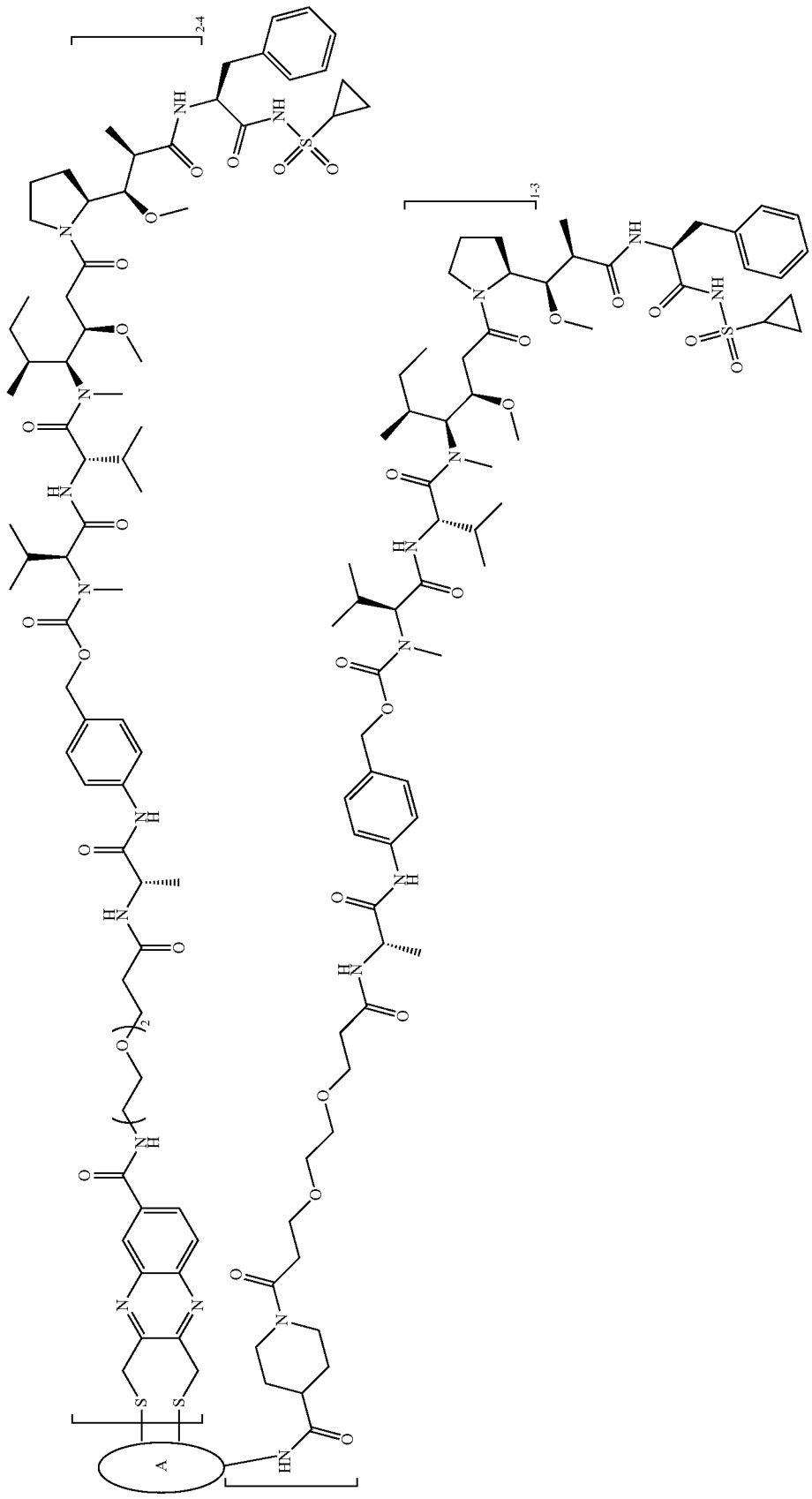

A targeting protein is conjugated to include at least two different types of drugs by using two different conjugation methods, a first conjugation method and a second conjugation method. The first conjugation method to derivatize a polypeptide with a payload can be accomplished using a maleimido or vinyl moiety which can react with individual sulfhydryl group on an antibody via Michael addition reaction. A free sulfhydryl group can be formed by reducing a disulfide bond in an antibody. However, the structural integrity of the targeting protein, such as an antibody, is compromised after opening disulfide bonds and attaching payloads to the exposed free thiols. The compositions and methods provided herein provide conjugation through a cysteine residue without decreased structural stability. The second conjugation method to derivatize a polypeptide with a payload is accomplished by forming an amide bond with a lysine side chain. Due to the presence of large number of lysine side chain amines with similar reactivity, this conjugation strategy can produce complex heterogeneous mixtures. The compositions and methods provided herein provide conjugation through lysine, where enhanced selectivity of the lysine can result in a less heterogenous mixture. The conjugation methods are designated "first" and "second" for convenience of discussion and do not indicate the order of conjugation.

The term "pharmaceutically acceptable salt" are salts that retain the biological effectiveness and properties of a compound and, which are not biologically or otherwise undesirable for use in a pharmaceutical. The disclosed compounds are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, (incorporated by reference herein in its entirety).

"$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo" means fluorine, chlorine, bromine, or iodine.

An "alkyl" refers to a straight or branched hydrocarbon chain that is fully saturated. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example, "$C_{1-4}$ alkyl" indicates that there are one to four carbon atoms in the alkyl chain, that is, the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl.

An "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy.

An "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto.

An "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{24}$ alkenyl" indicates that there are two to four carbon atoms in the alkenyl chain, that is, the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl.

An "alkynyl" is a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example, "$C_{2-4}$ alkynyl" indicates that there are two to four carbon atoms in the alkynyl chain, that is, the alkynyl chain is selected from the group consisting of ethynyl, propyn-1-yl, propyn-2-yl, butyn-1-yl, butyn-3-yl, butyn-4-yl, and 2-butynyl. Alkynyl groups include, for example, ethynyl, propynyl, butynyl, pentynyl, and hexynyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic groups provided that the entire ring system is aromatic.

An "aryloxy" and "arylthio" refers to RO— and RS—, in which R is an aryl as is defined above, such as "$C_{6-10}$ aryloxy" or "$C_{6-10}$ arylthio" such as phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

A "heteroaryl" refers to an aromatic ring or ring system that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

A "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" including, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl. In some cases, the alkylene group is a lower alkylene group.

"Cycloalkyl" means a fully saturated carbocyclyl ring or ring system. Examples include cyclopropyl, cyclobutyl, cyclopentyl, and cyclohexyl.

"Cycloalkenyl" means a carbocyclyl ring or ring system having at least one double bond, wherein no ring in the ring system is aromatic. An example is cyclohexenyl.

"Heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O (oxygen), N (nitrogen) or S (sulfur), and in preferred five membered monocyclic heterocyclyls, the heteroatom(s) are selected from one or two heteroatoms selected from O (oxygen), N (nitrogen), or S (sulfur). Examples of heterocyclyl rings include, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include imidazolinylmethyl and indolinylethyl.

An "acyl" is —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl. Examples include formyl, acetyl, propanoyl, benzoyl, and acryl.

An "O-carboxy" group is a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

A "C-carboxy" group is a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O) OH).

A "cyano" group is a "—CN" group.
A "cyanato" group is an "—OCN" group.
An "isocyanato" group is a "—NCO" group.
A "thiocyanato" group is a "—SCN" group.
An "isothiocyanato" group is an "—NCS" group.

A "sulfinyl" group is an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

A "sulfonyl" group is an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

An "S-sulfonamide" group is a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

An "N-sulfonamide" group is a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

An "O-carbamyl" group is a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

An "N-carbamyl" group is an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

An "O-thiocarbamyl" group is a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

A "urea" group is a "—N(R$_A$)C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

An "N-thiocarbamyl" group is an "—N(R$_A$)C(=S)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

A "C-amido" group is a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

An "N-amido" group is a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl.

An "amino" group is a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl. An example is free amino (—NH$_2$).

An "aminoalkyl" group is an amino group connected via an alkylene group.

An "alkoxyalkyl" group is an alkoxy group connected via an alkylene group, such as a "$C_{2-8}$ alkoxyalkyl".

A substituted group is derived from the unsubstituted parent group in which there has been an exchange of one or more hydrogen atoms for another atom or group. Unless otherwise indicated, when a group is deemed to be "substituted," it is meant that the group is substituted with one or more substituent's independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

Wherever a substituent is depicted as a di-radical (i.e., has two points of attachment to the rest of the molecule), it is to be understood that the substituent can be attached in any directional configuration unless otherwise indicated. For example, a substituent depicted as -AE- or includes the substituent being oriented such that the A is attached at the leftmost attachment point of the molecule as well as the case in which A is attached at the rightmost attachment point of the molecule.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

Definitions

As used herein, common organic abbreviations are defined as follows:
Ac Acetyl
aq. Aqueous
BOC or Boc tert-Butoxycarbonyl
BrOP bromo tris(dimethylamino) phosphonium hexafluorophosphate
Bu n-Butyl
° C. Temperature in degrees Centigrade
DCM methylene chloride
DEPC Diethylcyanophosphonate
DIC diisopropylcarbodiimide
DIEA Diisopropylethylamine DMA N,N-Dimethylformamide
DMF N,N-Dimethylformamide
EDC 1-Ethyl-3-(3-dimethylaminopropyl)carbodiimide
Et Ethyl
EtOAc Ethyl acetate
Eq Equivalents
Fmoc 9-Fluorenylmethoxycarbonyl
g Gram(s)
h Hour (hours)
HATU 2-(1H-7-azabenzotriazol-1-yl)-1,1,3,3-tetramethyl uronium hexafluorophosphate
HOBT N-Hydroxybenzotriazole
HOSu N-Hydroxysuccinimide
HPLC High-performance liquid chromatography
LC/MS Liquid chromatography-mass spectrometry
Me Methyl
MeOH Methanol
MeCN Acetonitrile
mL Milliliter(s)
MS mass spectrometry
PAB p-aminobenzyl
RP-HPLC reverse phase HPLC
rt room temperature
t-Bu tert-Butyl
TEA Triethylamine
Tert, t tertiary
TFA Trifluoracetic acid
THF Tetrahydrofuran
TLC Thin-layer chromatography
μL Microliter(s)

A general synthesis procedure forms an activated ester (e.g. NHS) from an acid. For example, an acid was dissolved in DCM, and DMF was added to aid dissolution if necessary. N-hydroxysuccinimide (1.5 eq) was added, followed by EDC.HCl (1.5 eq). The reaction mixture was stirred at room temperature for 1 h until most of the acid was consumed. The progress of the reaction was monitored by RP-HPLC. The mixture was then diluted with DCM and washed successively with citric acid (aq. 10%) and brine. The organic layer was dried and concentrated to dryness. The crude product was optionally purified by RP-HPLC or silica gel column chromatography.

Conjugation Methods, Spacers and Linkers Involved

Some embodiments provide a method of conjugating of a targeting molecule through a spacer or a multifunctional linker. In some embodiments, the spacer or multifunctional linker may include a 2- to 5-atom bridge. In some embodiments, the method includes a single-step or sequential conjugation approach. In some embodiments, the drug-conjugates include a spacer or a multifunctional linker. In some embodiments, the spacer or multifunctional linker may include a noncleavable or cleavable unit such as peptides.

Utilities and Applications

Some embodiments provide a method of treating a patient in need thereof comprising administering an active agent-conjugate as disclosed and described herein to said patient. In some embodiments, the patient may have cancer, immune diseases or diabetes.

Some embodiments provide a method of diagnosis or imaging comprising administering an active agent-conjugate as disclosed and described herein to an individual.

Disclosed Compositions

The disclosed pharmaceutical compositions have a structure in Formula I $$\left[ D^1-L^2 \underset{O}{\overset{H}{\underset{\|}{C}}} N \right]_m A \left[ \underset{S}{\overset{S}{\diagdown}} \underset{L^4}{\overset{L^3}{\diagup}} E-L^2-D^2 \right]_n$$ (I)

or a pharmaceutically acceptable salt thereof,
wherein:
A is a targeting protein;
each $D^1$ is a first active agent;
each $L^1$ is independently a linker including at least one N (nitrogen) atom;
each $D^2$ is a second active agent;
each $L^2$ is independently a linker;
the E-component is an optionally substituted heteroaryl or an optionally substituted heterocyclyl;
each $L^3$ is an optionally substituted $C_1$-$C_6$ alkyl, or $L^3$ may be null, when $L^3$ is null the sulfur is directly connected to the E-component; and
each $L^4$ is an optionally substituted $C_1$-$C_6$ alkyl, or $L^4$ may be null, when $L^4$ is null the sulfur is directly connected to the E-component;
m and n are independently integers from 1-10.

Preferably, A is selected from the group consisting of a monoclonal antibody (mAB), and an antibody fragment.

$D^1$ and $D^2$ are different drug compounds, preferably an anti-cancer drug or an immune modulator. Examples of D1 and D2 are tubulin binders, DNA alkylating agents, HSP90 inhibitors, DNA topoisomerase inhibitors, anti-epigenetic agents, HDAC inhibitors, anti-metabolism agents, proteasome inhibitors, an siRNA, an antisense DNA, epothilone A, epothilone B, or paclitaxel.

$L^1$ may include a spacer or a multifunctional linker. $L^1$ may include a spacer and a multifunctional linker. In some embodiments, $L^1$ may include a multifunctional linker. In some embodiments, each $L^1$ may be a linker, wherein the linker may be cleavable or non-cleavable under biological conditions. In some embodiments, the linker may be cleavable by an enzyme. In some embodiments, $L^1$ may include Linker.

In some embodiments, $L^2$ may include a spacer or a multifunctional linker. In some embodiments, $L^2$ may include a spacer and a multifunctional linker. In some embodiments, $L^2$ may include a multifunctional linker. In some embodiments, each $L^2$ may be a linker, wherein the linker may be cleavable or non-cleavable under biological conditions. In some embodiments, the linker may be cleavable by an enzyme. In some embodiments, $L^2$ may include Linker.

$L^2$ includes a cyclic group including at least one N (nitrogen) atom. In some embodiments, $L^2$ includes a cyclic group including at least two N (nitrogen) atoms. In some embodiments, $L^2$ includes a cyclic group including at least one N (nitrogen) atom and a spacer.

A comprises at least one modified L-Alanine residue. In some embodiments, A comprises at least two modified L-Alanine residues. In some embodiments, A comprises at least one modified L-Alanine residue that is connected to at least one sulfur. In some embodiments, at least one modified L-Alanine residue is from an L-Cysteine residue of a peptide before conjugation.

A comprises at least one modified n-butyl L-a-amino acid. In some embodiments, A comprises at least one modified L-Lysine residue is from an L-Lysine residue of a peptide before conjugation. In some embodiments, A-NH together comprise at least one modified L-Lysine residue. In some embodiments, the terminal nitrogen of the side chain of an L-Lysine residue of a peptide before conjugation provides the NH of A-NH of Formula I. In some embodiments, A comprises the —(CH$_2$)$_4$— of the side chain of an L-Lysine residue of a peptide before conjugation that provides the at least one A-NH of Formula I. In some embodiments, A comprises a modified n-butyl a-amino acid residue.

Linker may be a peptide.

Linker may include an oligosaccharide. For example, Linker may include chitosan. In some embodiments, L$^2$ may include Linker and —(CH$_2$)$_n$— where n is 1, 2, 3, 4, 5, 6, 7, 8, 9, or 10. In some embodiments, L$^2$ may include Linker and —(CH$_2$CH$_2$O)$_n$— where n is 1, 2, 3, 4, 5, 6, 7, 8, 9, or 10.

Linker may include —(CH$_2$)$_n$— where n is 1, 2, 3, 4, 5, 6, 7, 8, 9, or 10.

Linker may include —(CH$_2$CH$_2$O)$_n$— where n is 1, 2, 3, 4, 5, 6, 7, 8, 9, or 10.

Linker may include Val-Cit-PAB, Val-Ala-PAB, Val-Lys (Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, or the like.

Linker may include any combination of peptide, oligosaccharide, —(CH$_2$)$_n$—, —(CH$_2$CH$_2$O)$_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB, and the like.

A spacer is any combination of peptide, oligosaccharide, —(CH$_2$)$_n$—, —(CH$_2$CH$_2$O)$_n$—, Val-Cit-PAB, Val-Ala-PAB, Val-Lys (Ac)-PAB, Phe-Lys-PAB, Phe-Lys(Ac)-PAB, D-Val-Leu-Lys, Gly-Gly-Arg, Ala-Ala-Asn-PAB, Ala-PAB, PAB.

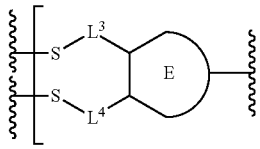

includes a 4-carbon bridge.

L$^3$, L$^4$ and a portion of the E-component include a 4-carbon bridge.

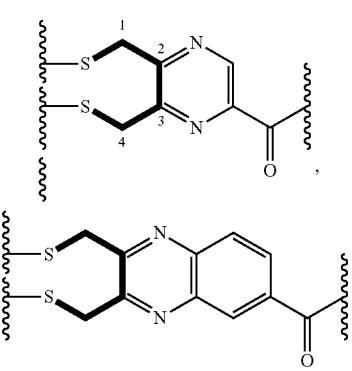

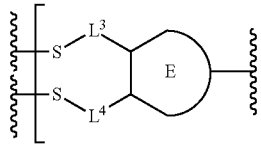

includes,

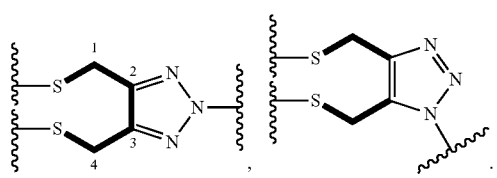

The S-linked portion of

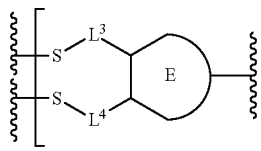

comprises a modified L-Alanine residue, wherein

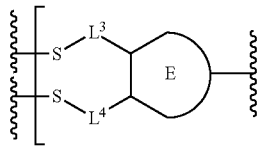

connects to a sulfur of a reduced disulfide bond through a bridge containing 2 to 5 atoms. For example, the structure indicated by

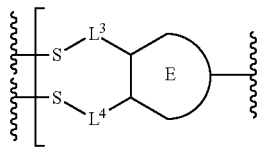

includes a fragment selected from the group consisting of:

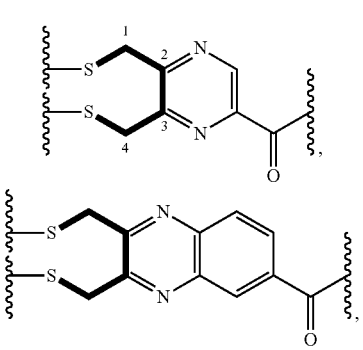

-continued

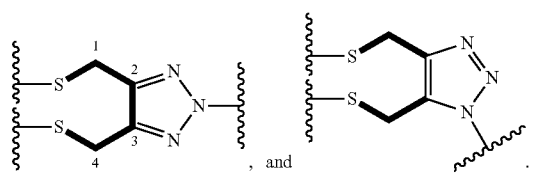, and

The S-linked (sulfur-linked) portion of

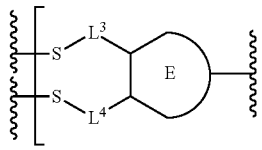

comprises a modified L-Alanine residue. In some embodiments, the S-linked (sulfur-linked) portion of

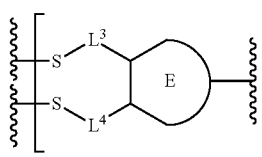

comprises a modified L-Alanine residue wherein the modified L-Alanine component of

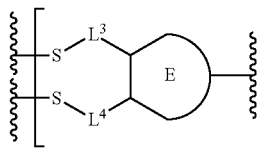

is from an L-Cysteine residue of a peptide before conjugation. Each sulfur of

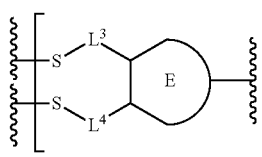

is from an L-Cysteine of a peptide before conjugation.

The structural component is:

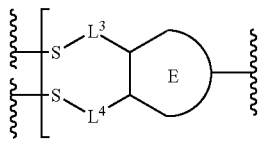

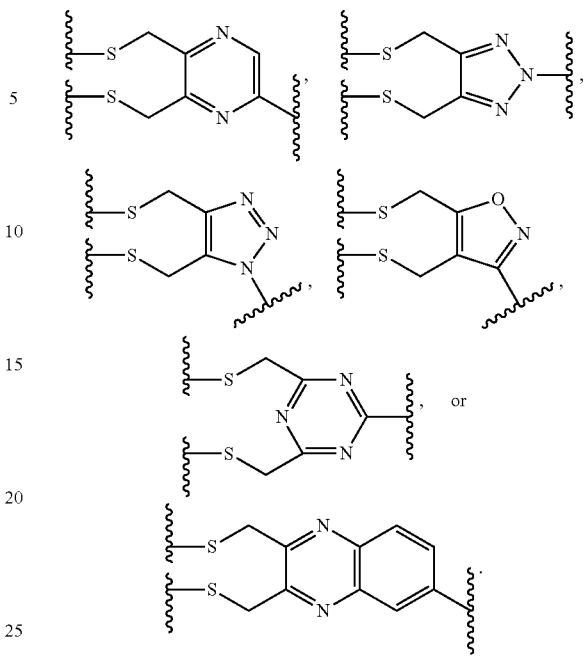

The E-component includes a fragment selected from the group consisting of:

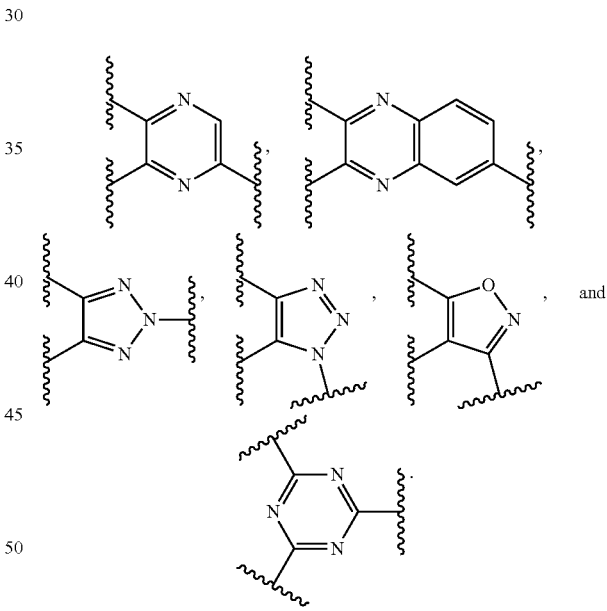

$L^1$ may include,

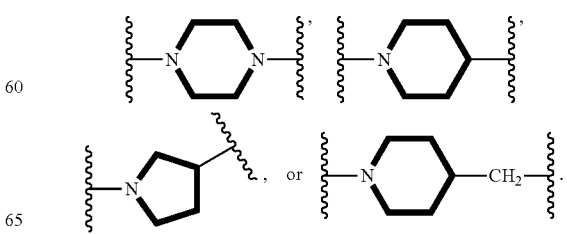

The active agent may be selected from the group consisting of tubulin binders, DNA alkylators, DNA intercalator, enzyme inhibitors, immune modulators, peptides, and nucleotides.

At least one $L^1$ or $L^2$ includes —$(CH_2)_n$— where n is 1, 2, 3, 4, 5, 6, 7, 8, 9, or 10. In some embodiments, at least one $L^1$ or $L^2$ includes —$(CH_2CH_2O)_n$— where n is 1, 2, 3, 4, 5, 6, 7, 8, 9, or 10. In some embodiments, at least one $L^1$ or $L^2$ includes Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB. In some embodiments, at least one $L^1$ or $L^2$ includes a peptide, an oligosaccharide, —$(CH_2)_n$—, —$(CH_2CH_2O)_n$—, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB, or PAB.

The targeting moiety may be an antibody. In some embodiments, the targeting moiety may be a monoclonal antibody (mAb). The A component comprises a humanized antibody. In some embodiments, the A component comprises a chimeric antibody. In some embodiments, the A component comprises a bispecific antibody. In some embodiments, the targeting moiety may be an antibody fragment, surrogate, or variant.

The targeting moiety may be HuM195-Ac-225, HuM195-Bi-213, Anyara (naptumomab estafenatox; ABR-217620), AS 1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544. In some embodiments, the targeting moiety may comprise, consist of, or consist essentially of the antibody portion of HuM195-Ac-225, HuM195-Bi-213, Anyara (naptumomab estafenatox; ABR-217620), AS1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{13}$4, L19-TNF, PSMA-ADC, DI-Leu16-IL2, SAR3419, SGN-35, or CMC544.

The targeting moiety may be Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

The targeting moiety may comprise, consist of, or consist essentially of the antibody portion of Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

The targeting moiety may comprise, consist of, or consist essentially of Brentuximab, Inotuzumab, Gemtuzumab, Milatuzumab, Trastuzumab, Glembatumomab, Lorvotuzumab, or Labestuzumab.

Conjugation Method I

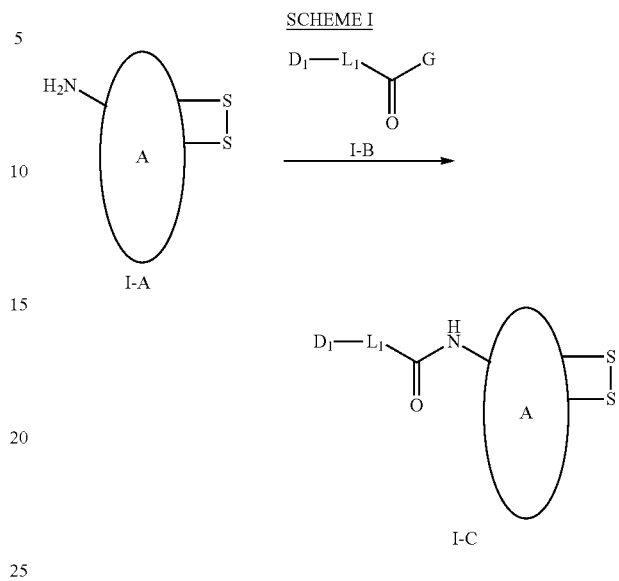

Scheme I. G is selected from the group consisting of —F, —Cl, —Br, —I, —$N_3$, —OR, SR, —ONRR, RC(=O)O—, and $RSO_2$—O—; and R is optionally substituted alkyl, or optionally substituted aryl.

General Conjugation Procedure I-A:

To a solution of 0.5-50 mgs/mL of I-A in buffer at pH 6.0-9.0 with 0-30% organic solvent, is added 0.1-10 eq of activated carboxylic component I-B in a manner of portion wise or continuous flow. The reaction is performed at 0-40° C. for 0.5-50 hours with gentle stirring or shaking, monitored by HIC-HPLC. The resultant crude ADC product undergoes necessary down-stream steps of desalt, buffet changes/formulation, and optionally, purification, using the state-of-art procedures. The ADC product I-C is characterized by HIC-HPLC, SEC, RP-HPLC, and optionally LC-MS.

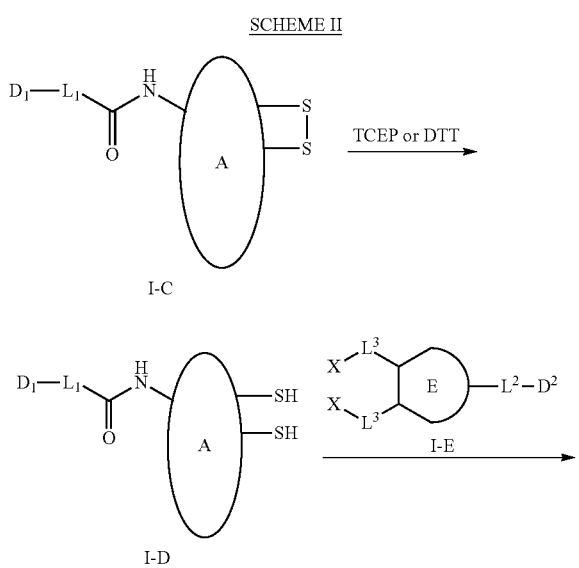

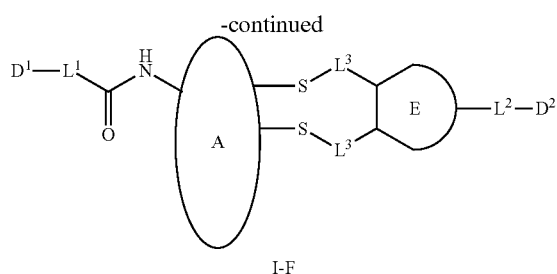

I-F

Scheme I. X is selected from the group consisting of —Cl, —Br, —I, and RSO$_2$—O—; and R is optionally substituted alkyl, or optionally substituted aryl General Conjugation Procedure I-B:

To the ADC product I-C, 0.5-50 mgs/mL, in a certain buffet at pH 5.0-9.0, such as PBS, is added 0.5-100 eq of reducing agent such as TCEP and DTT to afford intermediate I-D. The reduction is performed at 0-40° C. for 0.5-40 hours with gentle stirring or shaking, and then the reducing agent is removed by column or ultrafiltration. To intermediate I-D, 0.5-50 mgs/mL, in a certain buffet at pH 5.0-9.0, such as PBS, with 0-30% of organic co-solvent such as DMA, is added 0.5-10 eq of the activated drug-linker reactant I-E. The reaction is conducted at 0-40° C. for 0.5-40 hours with gentle stirring or shaking, monitored by HIC-HPLC. The resultant crude ADC product I-E undergoes necessary down-stream steps of desalt, buffet changes/formulation, and optionally, purification, using the state-of-art procedures. The final ADC product I-E is characterized by HIC-HPLC, SEC, RP-HPLC, and optionally LC-MS.

Conjugation Method II

SCHEME III

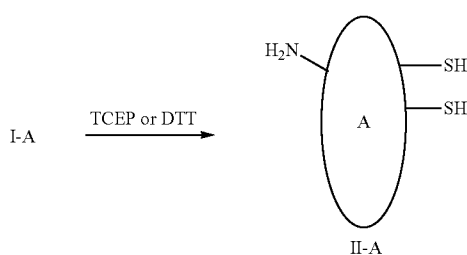

General Conjugation Procedure II-A:

To a mixture of I-A, 0.5-50 mgs/mL, in a certain buffet at pH 5.0-9.0, such as PBS, is added 0.5-100 eq of reducing agent such as TCEP and DTT to afford intermediate II-A. The reduction is performed at 0-40° C. for 0.5-40 hours with gentle stirring or shaking, and then the reducing agent is removed by column or ultrafiltration.

SCHEME IV

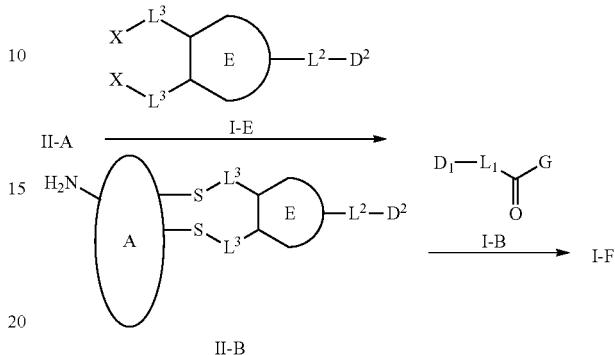

Scheme IV.

X is selected from the group consisting of —Cl, —Br, —I, and RSO$_2$—O—; and R is optionally substituted alkyl, or optionally substituted aryl General Conjugation Procedure II-B:

To intermediate II-A, 0.5-50 mgs/mL, in a certain buffet at pH 5.0-9.0, such as PBS, with 0-30% of organic co-solvent such as DMA, is added 0.5-10 eq of the activated drug-linker reactant I-E. The reaction is conducted at 0-40° C. for 0.5-40 hours with gentle stirring or shaking, monitored by HIC-HPLC. The resultant crude ADC product II-B undergoes necessary down-stream steps of desalt, buffet changes/formulation, and optionally, purification, using the state-of-art procedures.

To a solution of 0.5-50 mgs/mL of II-B in buffer at pH 6.0-9.0 with 0-30% organic solvent, is added 0.1-10 eq of activated carboxylic component I-B in a manner of portion wise or continuous flow. The reaction is performed at 0-40° C. for 0.5-50 hours with gentle stirring or shaking, monitored by HIC-HPLC. The resultant crude ADC product I-F undergoes necessary down-stream steps of desalt, buffet changes/formulation, and optionally, purification, using the state-of-art procedures. The ADC product I-F is characterized by HIC-HPLC, SEC, RP-HPLC, and optionally LC-MS.

Examples of activated carboxylic component I-B include:

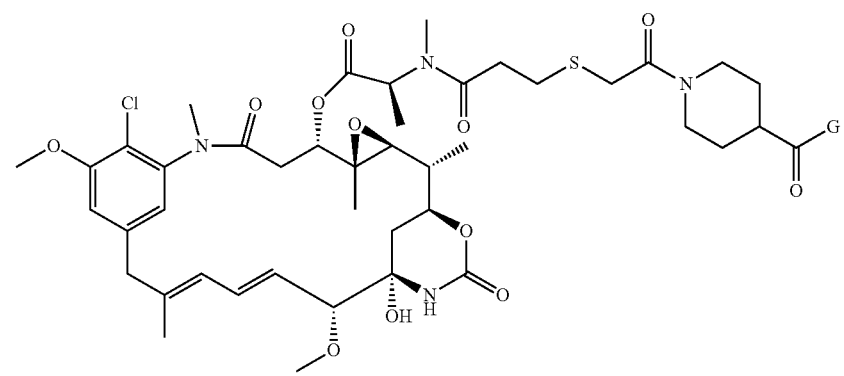

-continued
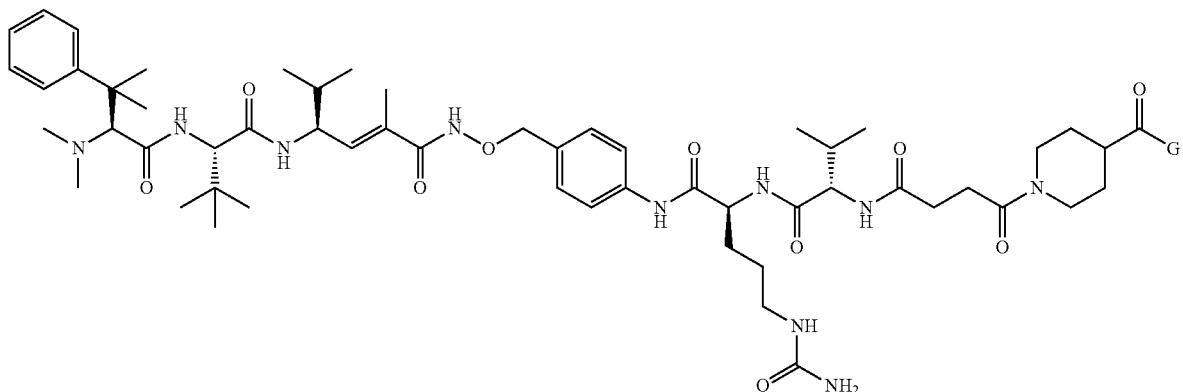
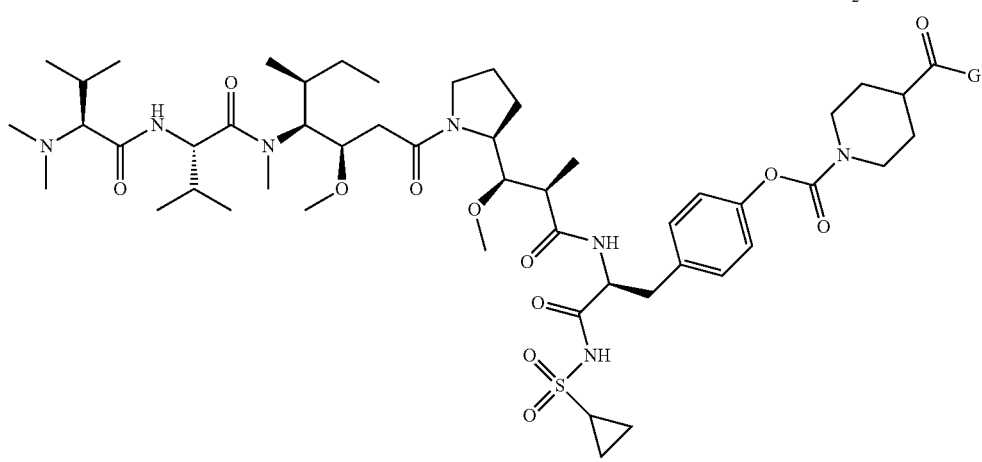
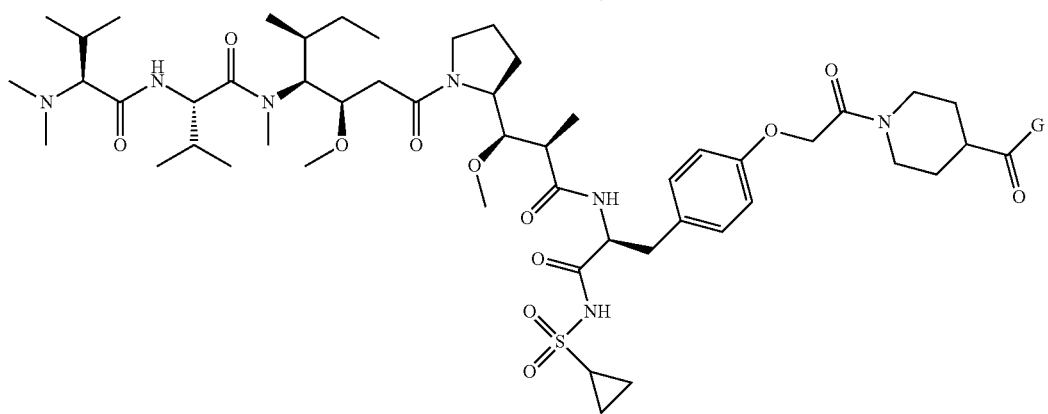
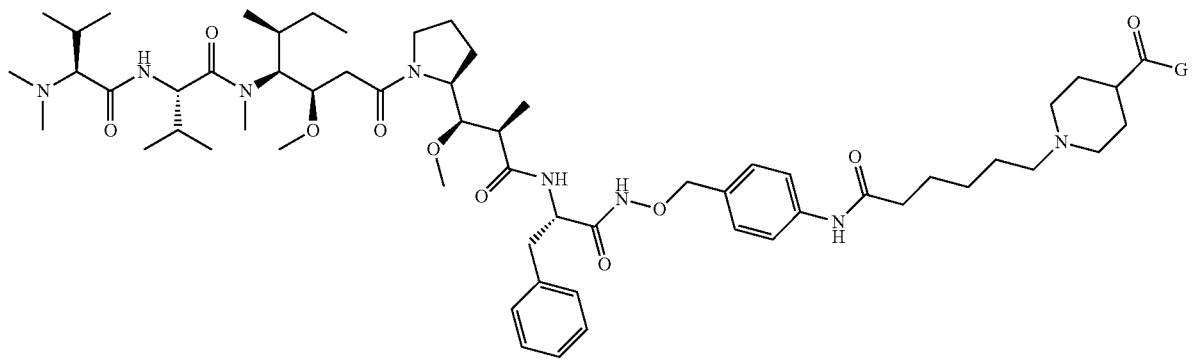

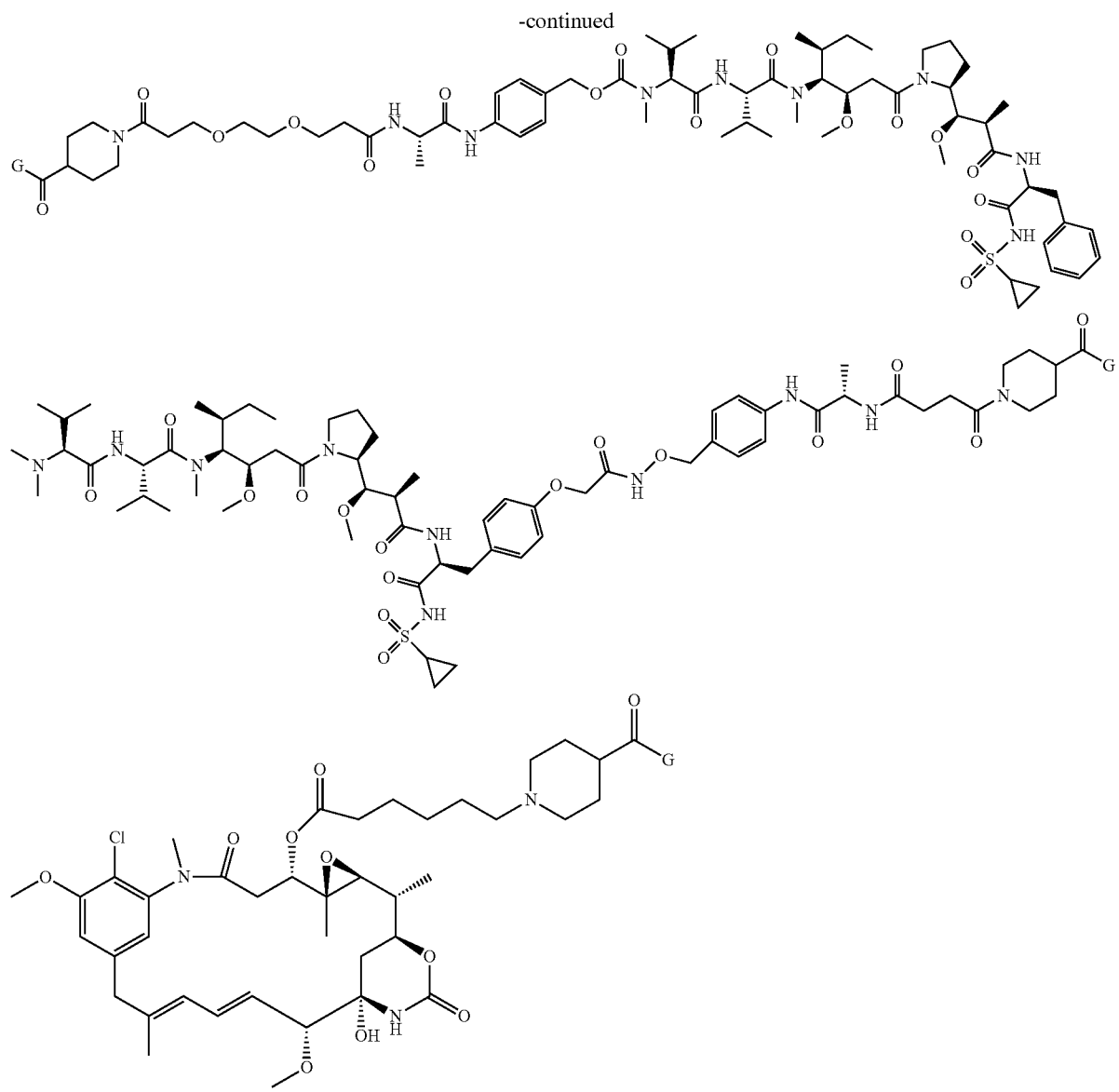
wherein G is selected from the group consisting of —F, —Cl, —Br, —I, —N₃, —OR, SR, —ONRR, RC(═O)O—, and RSO₂—O—; and R is optionally substituted alkyl, or optionally substituted aryl.
Examples of activated drug-linker reactant I-E are:
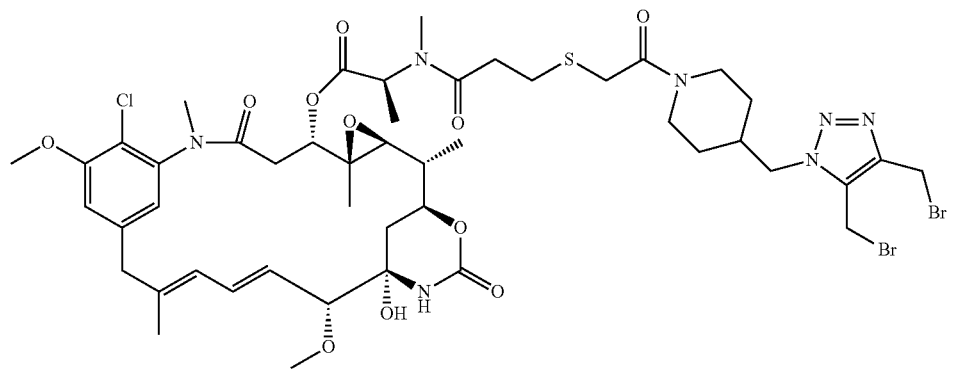

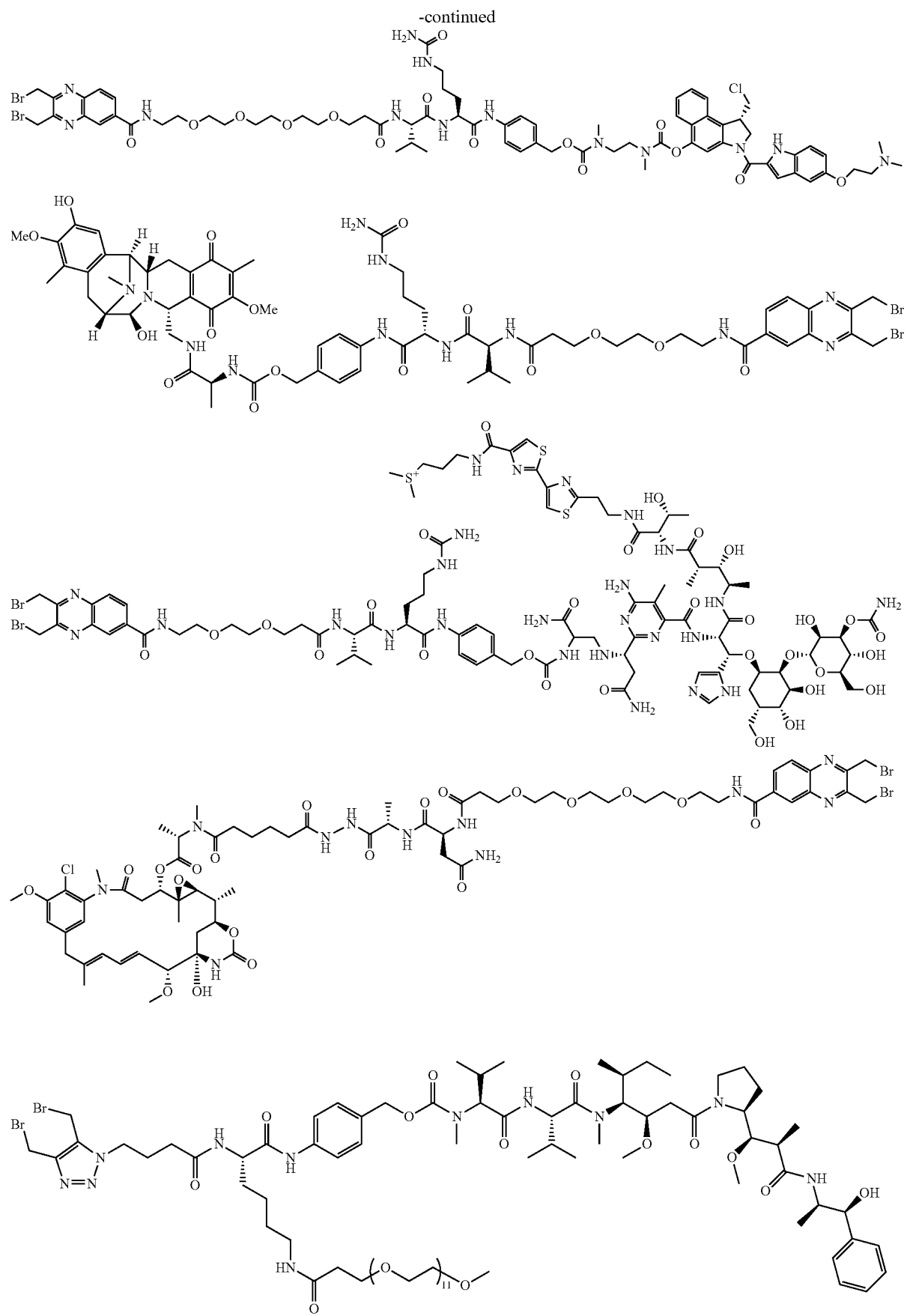

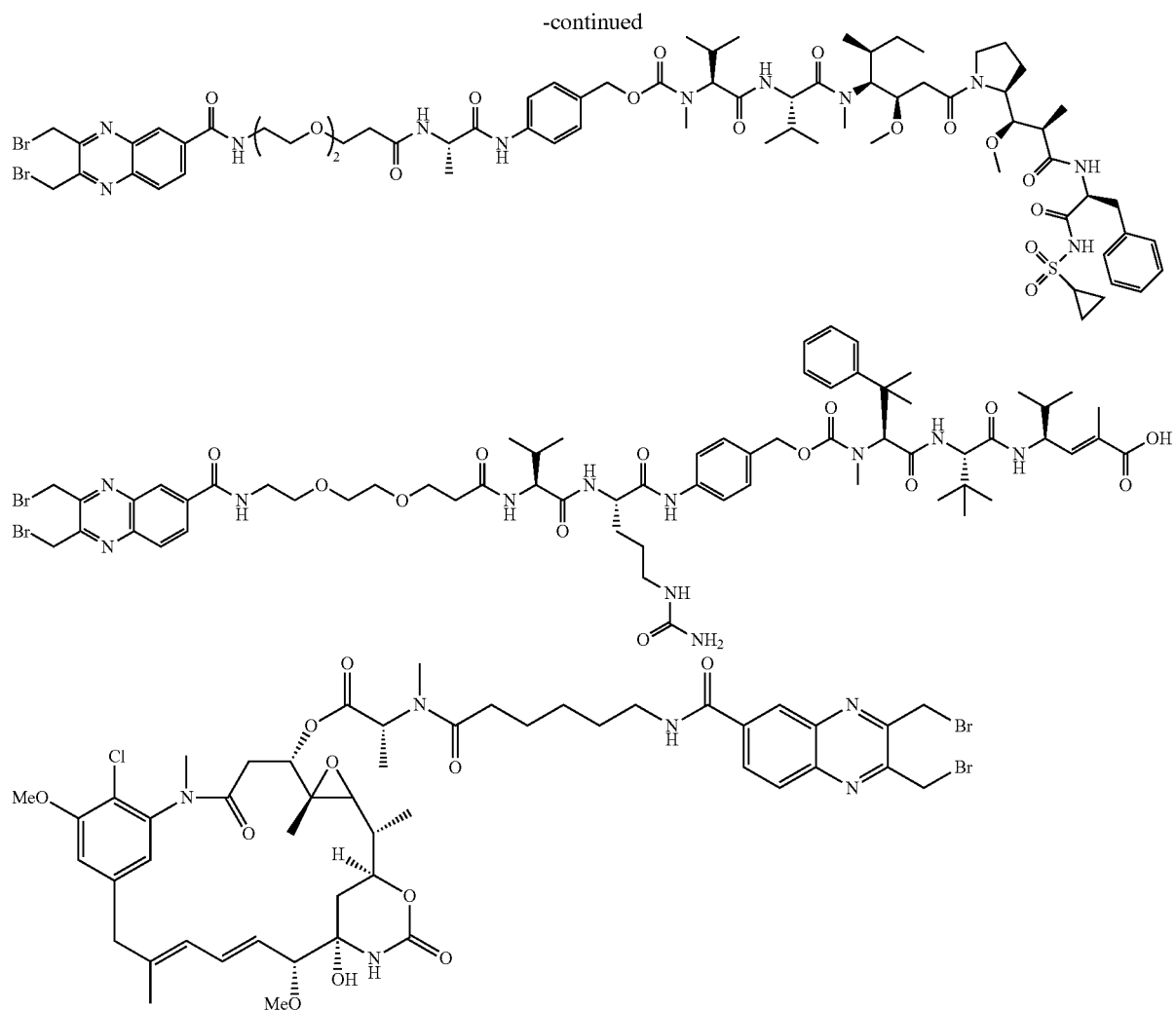
Examples of compounds of Formula I:

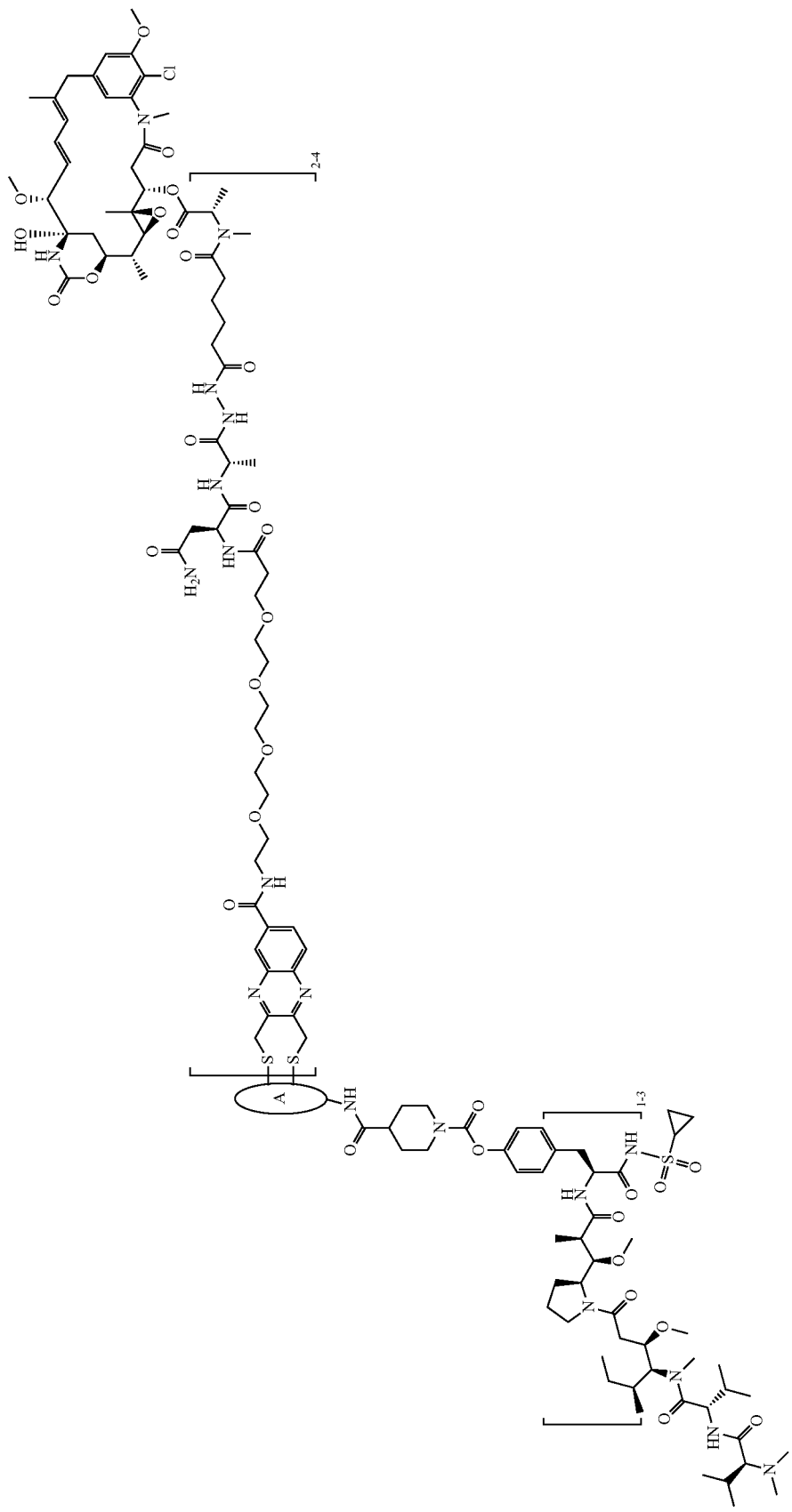

-continued
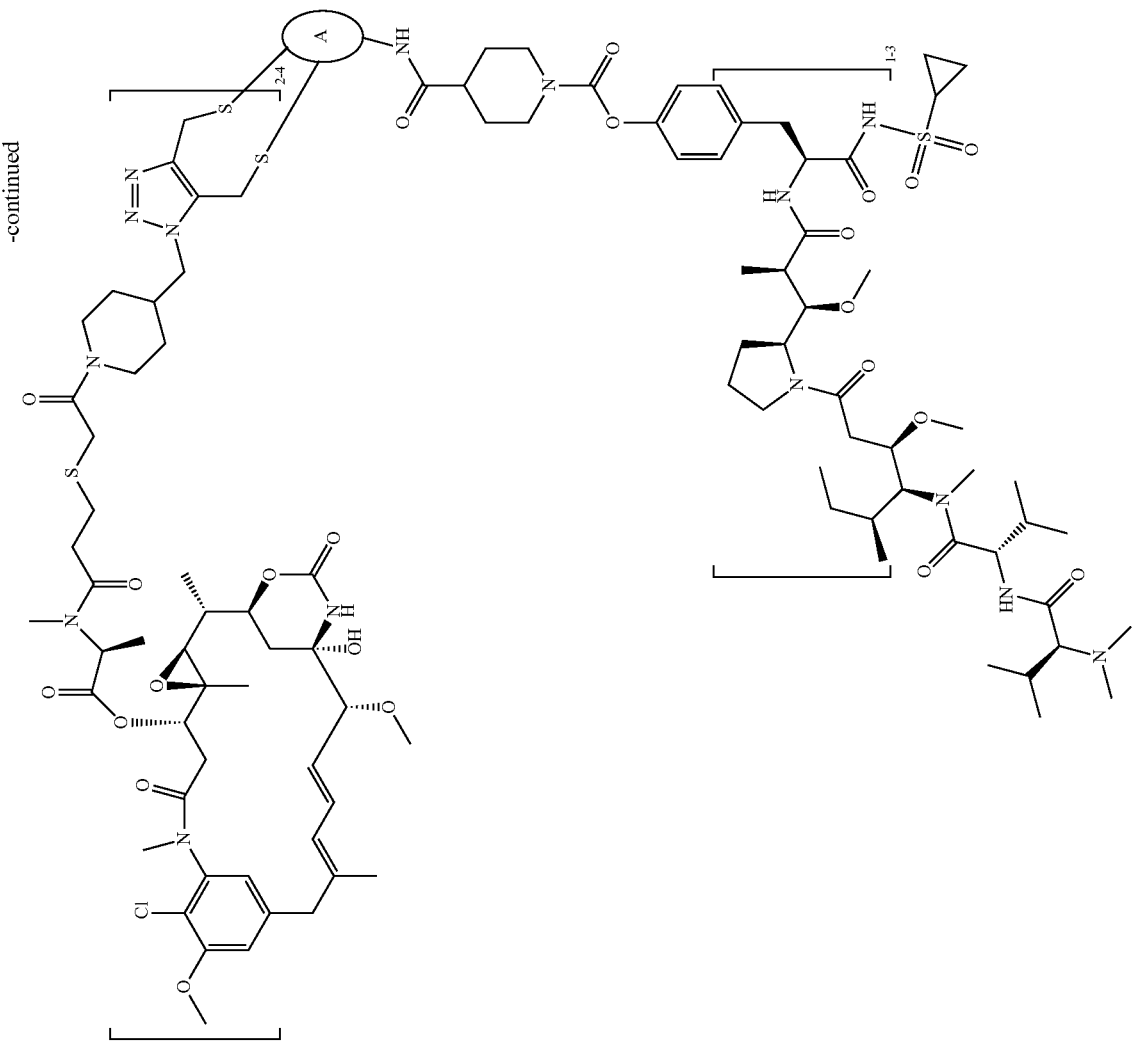

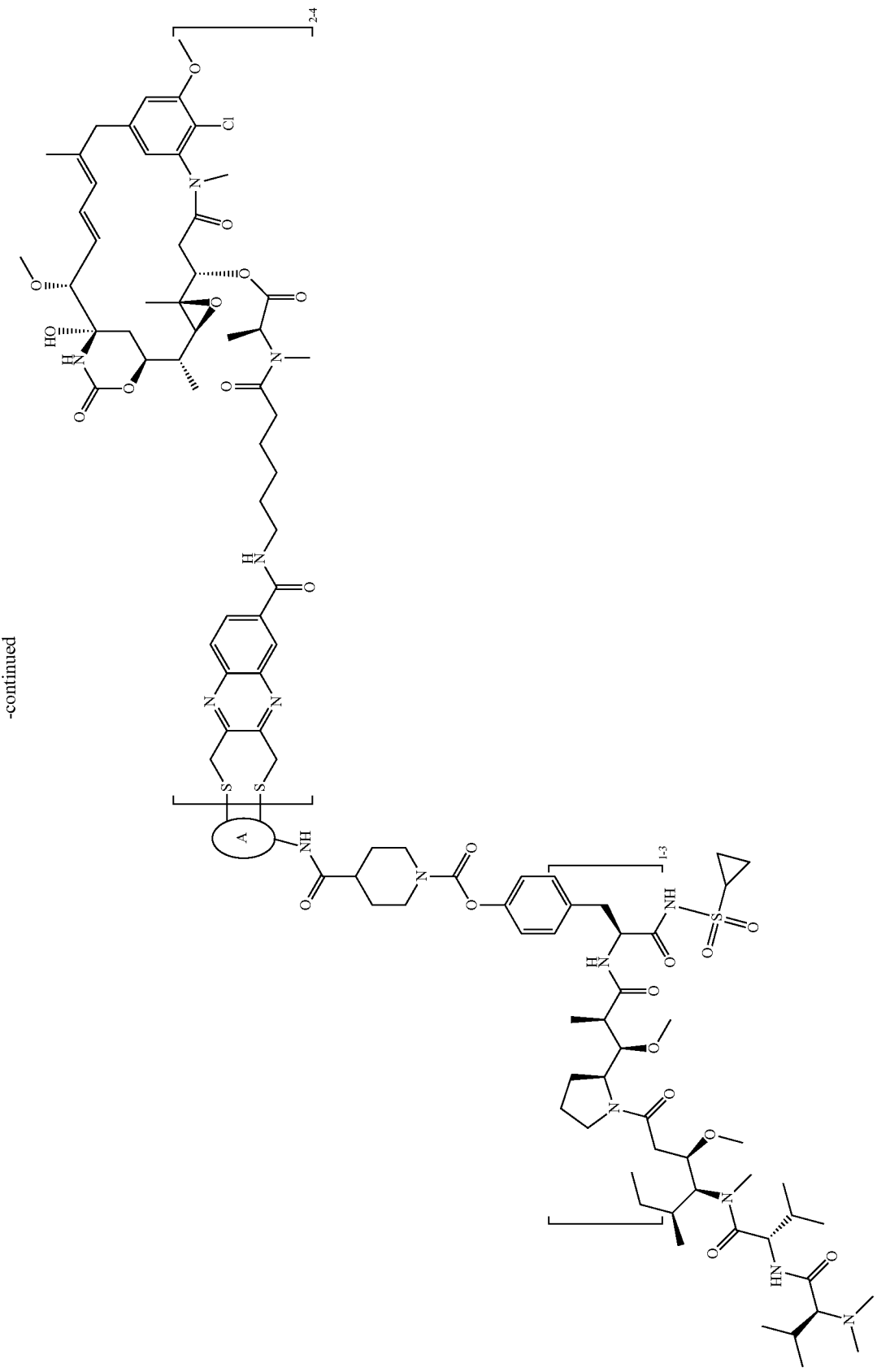

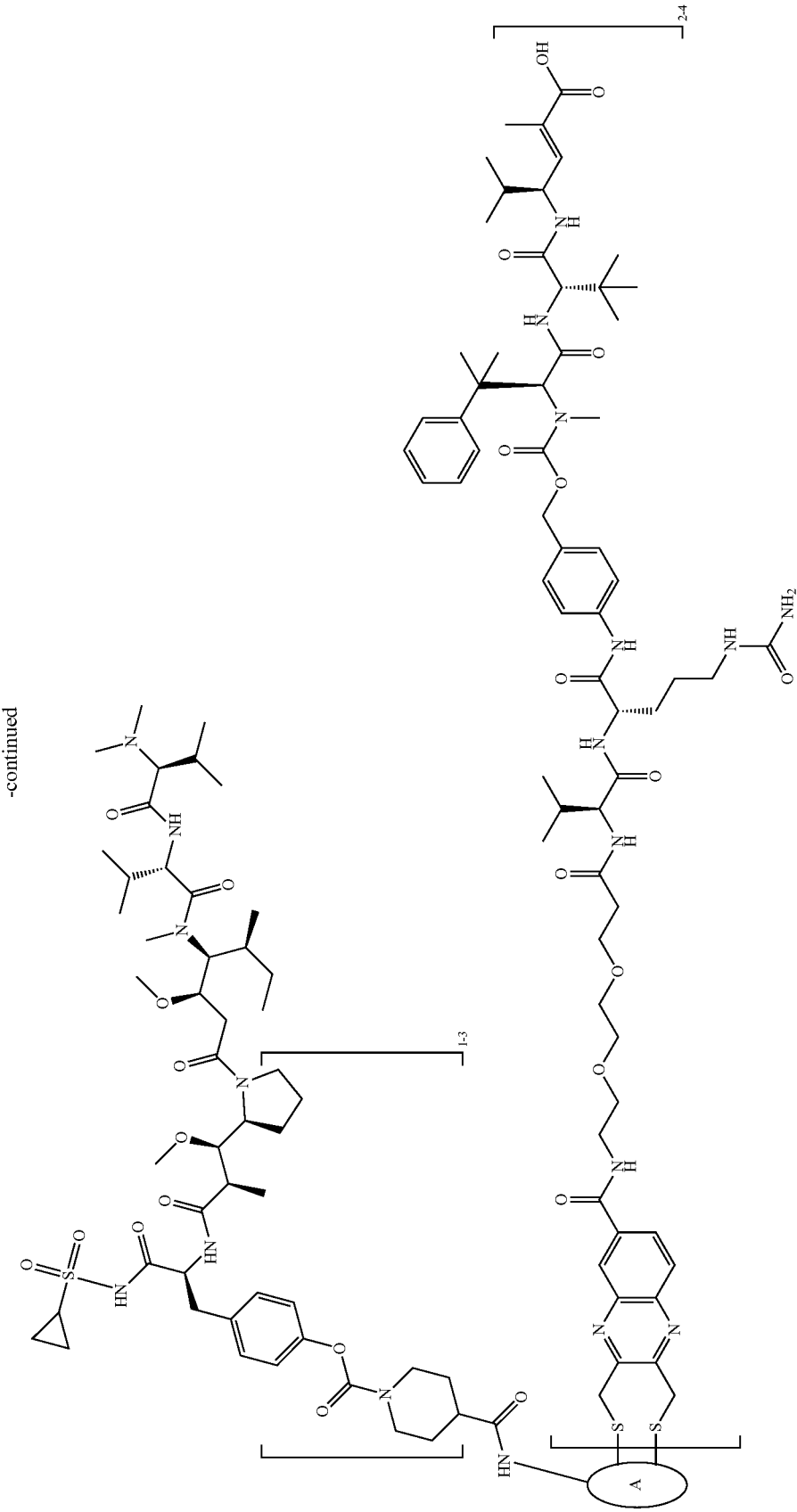

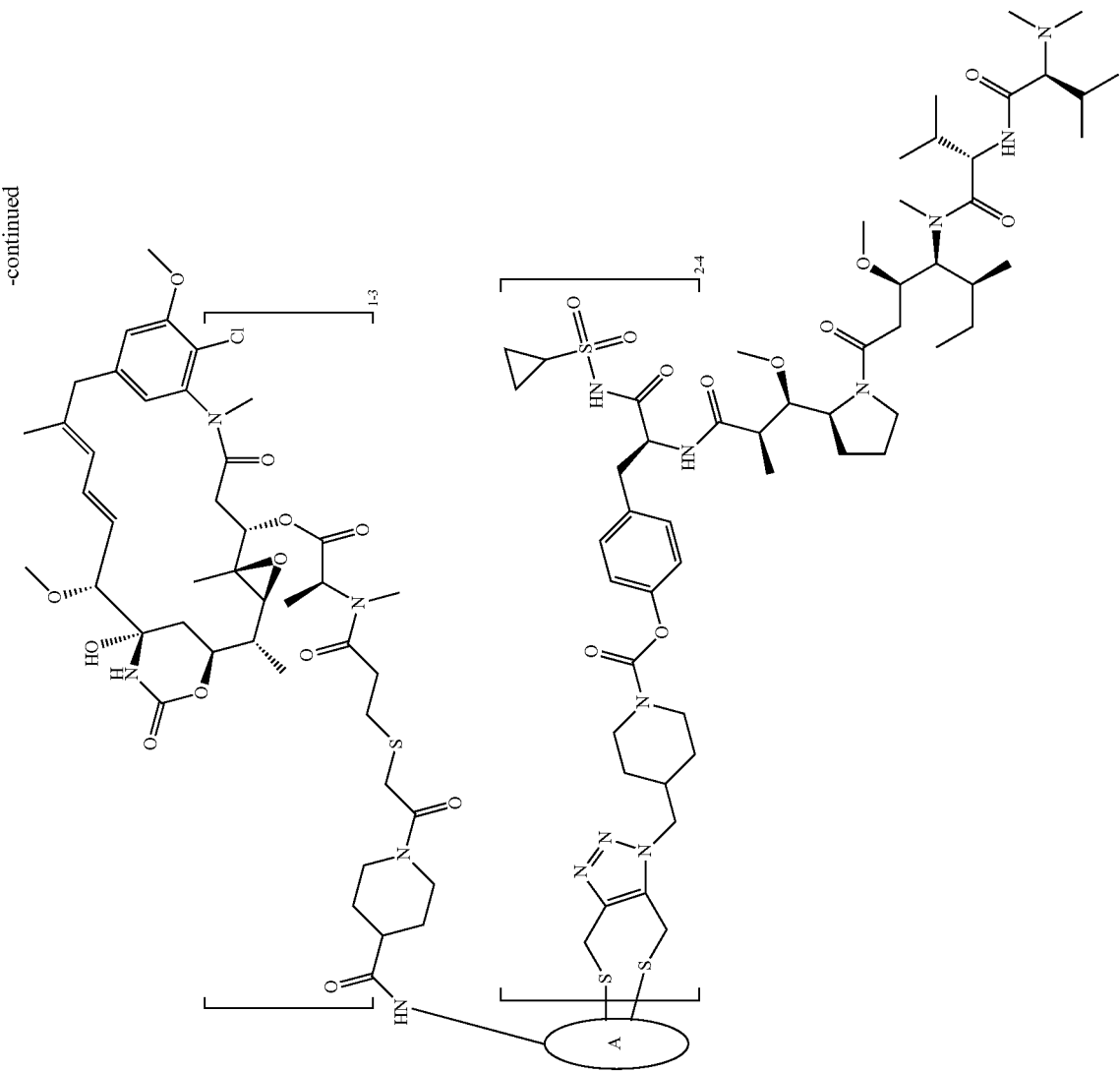

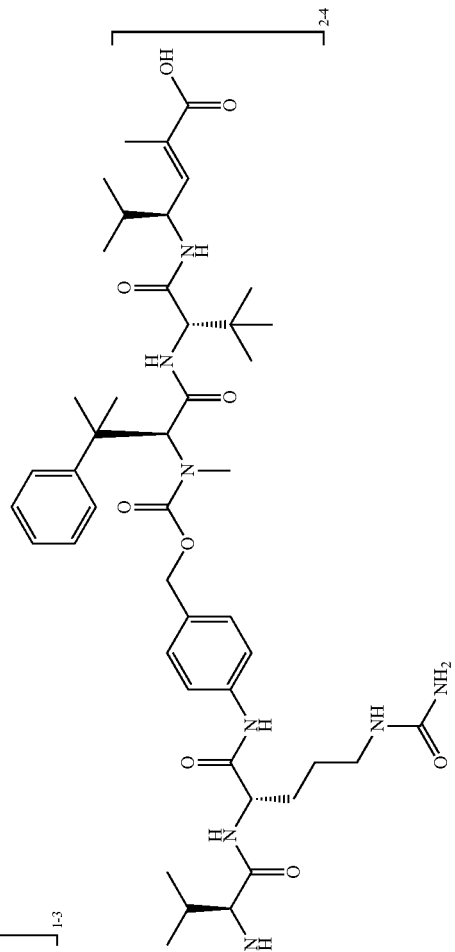
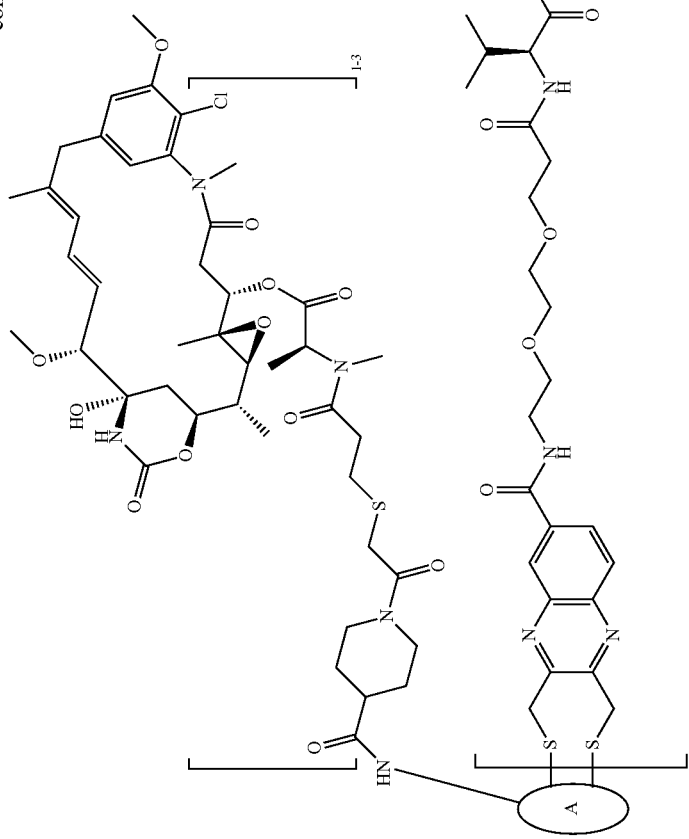

-continued
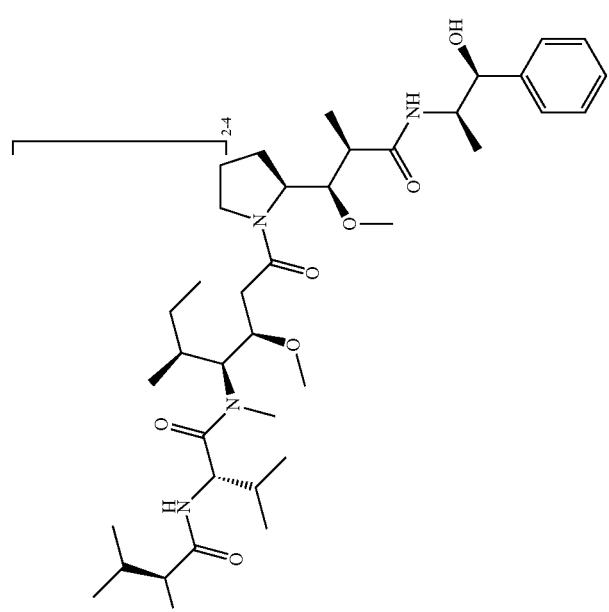
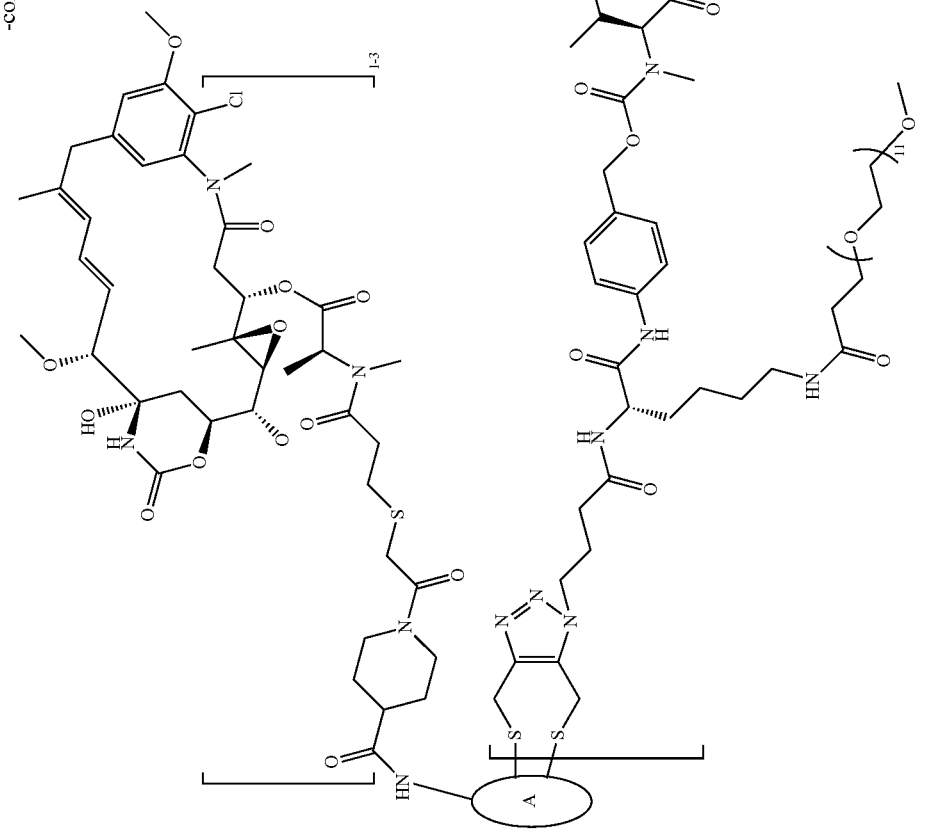

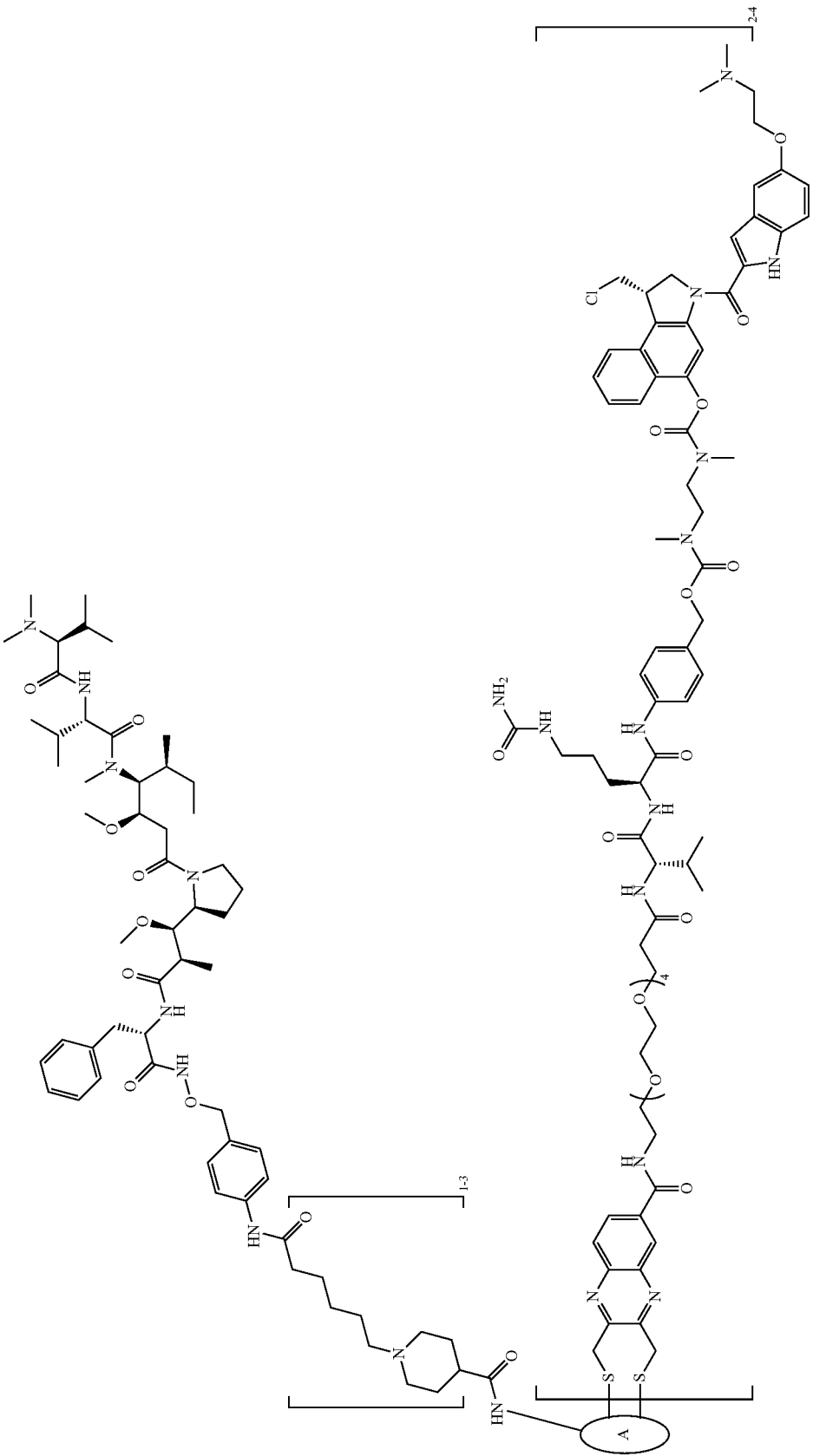

-continued
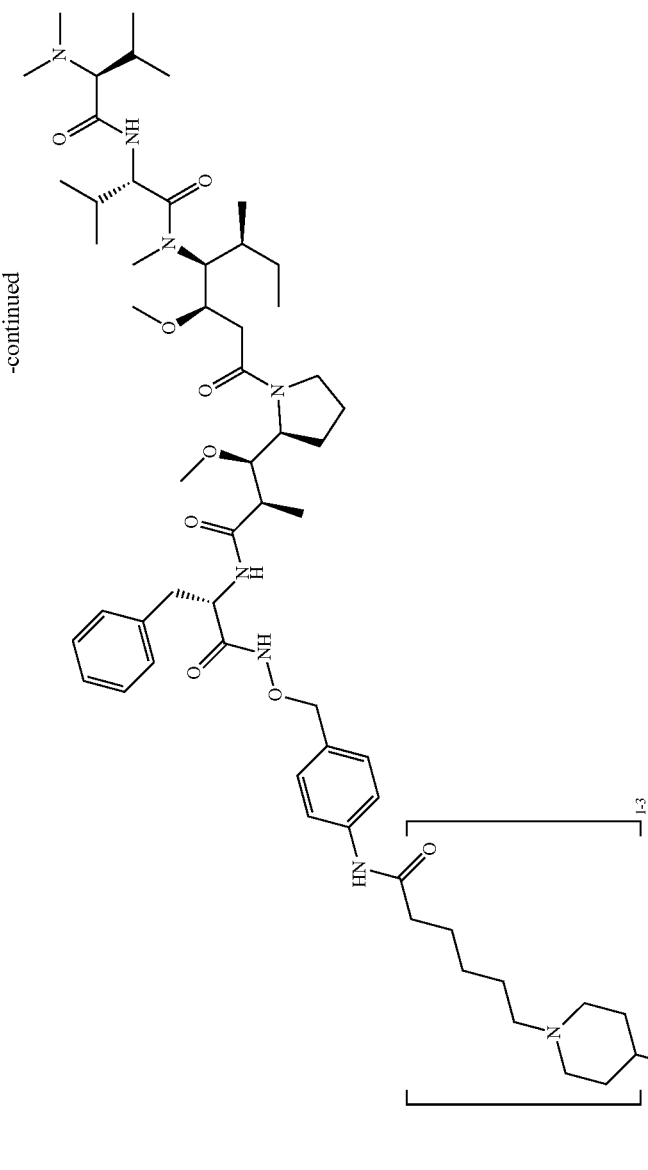
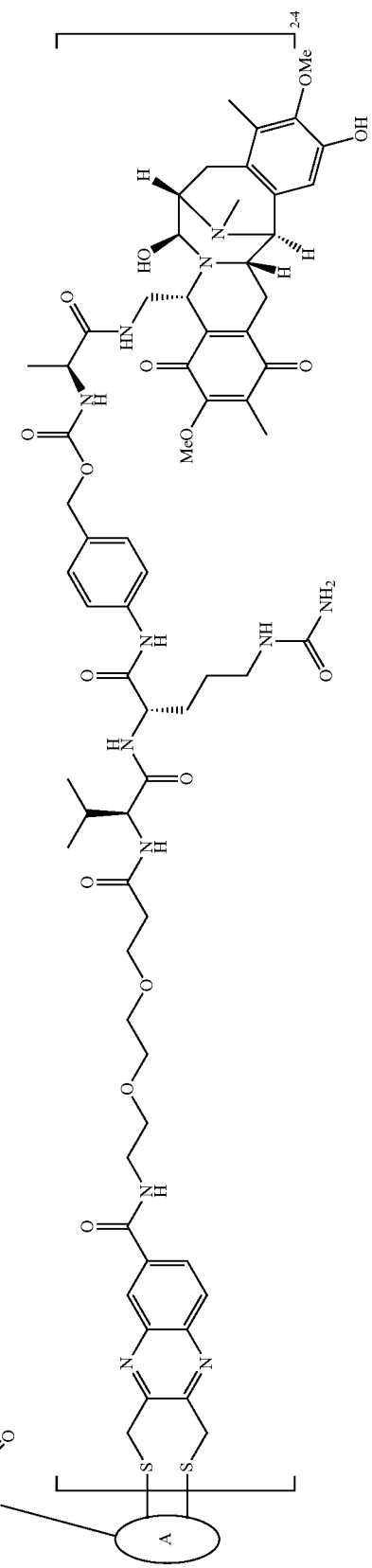

-continued
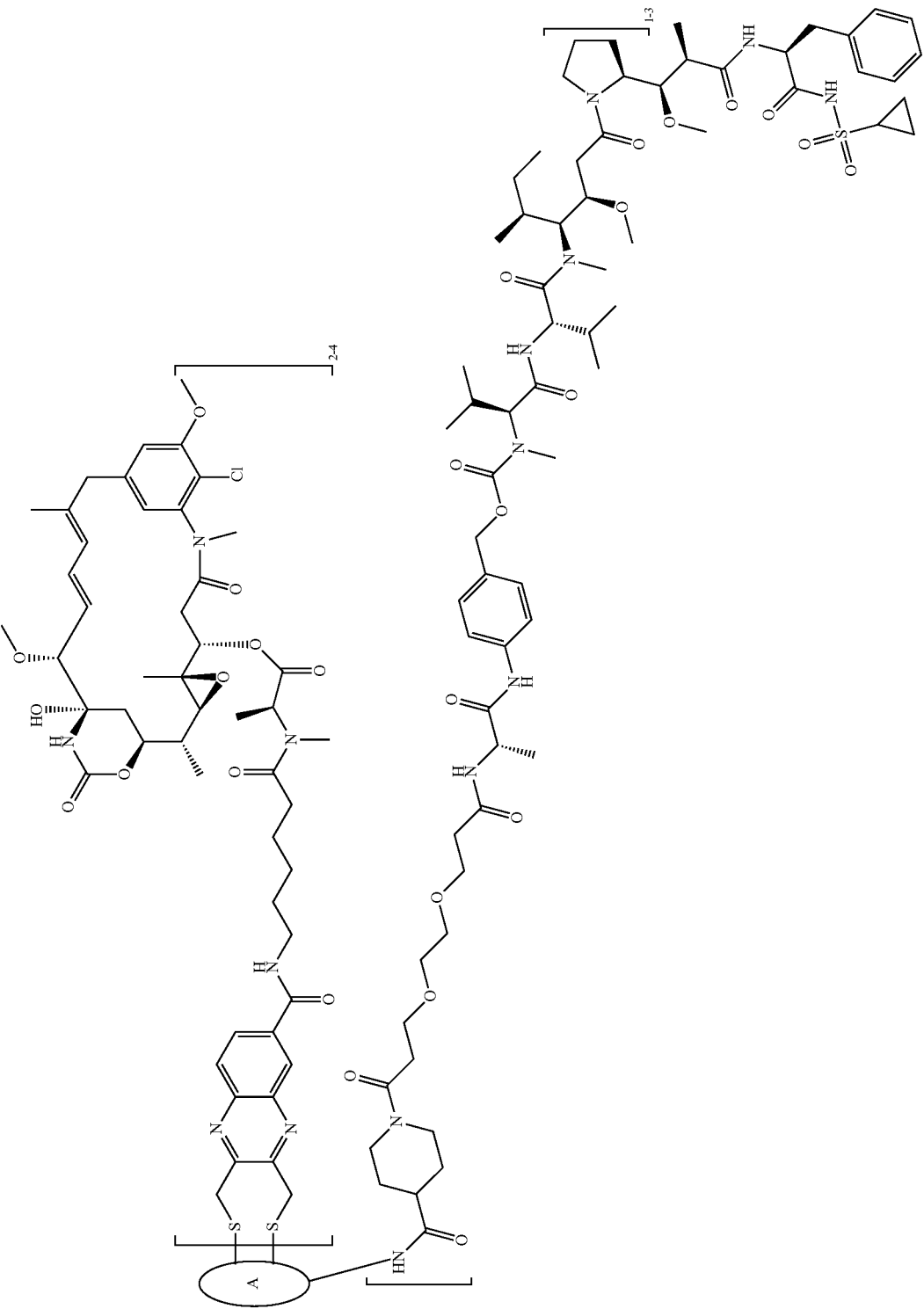

-continued
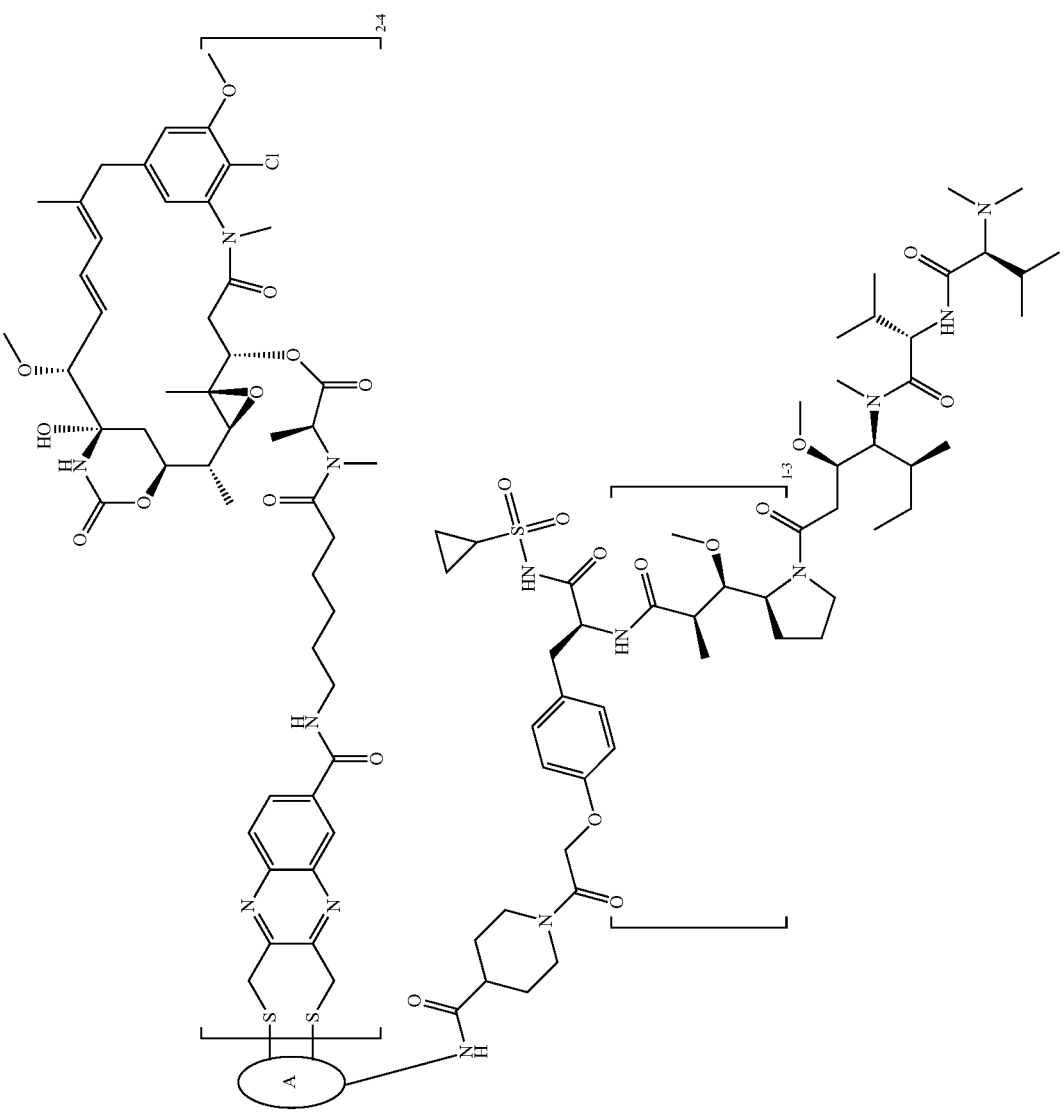

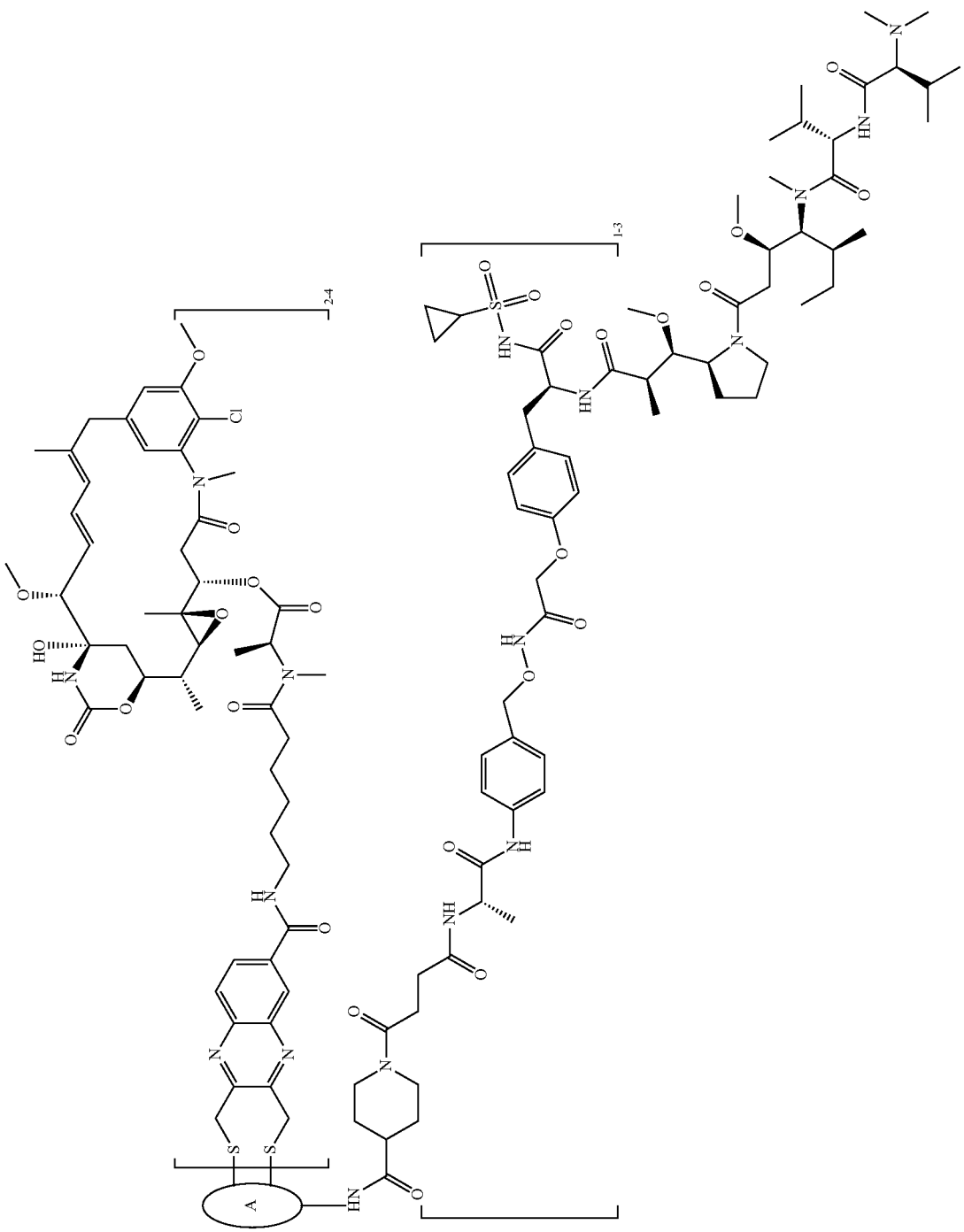

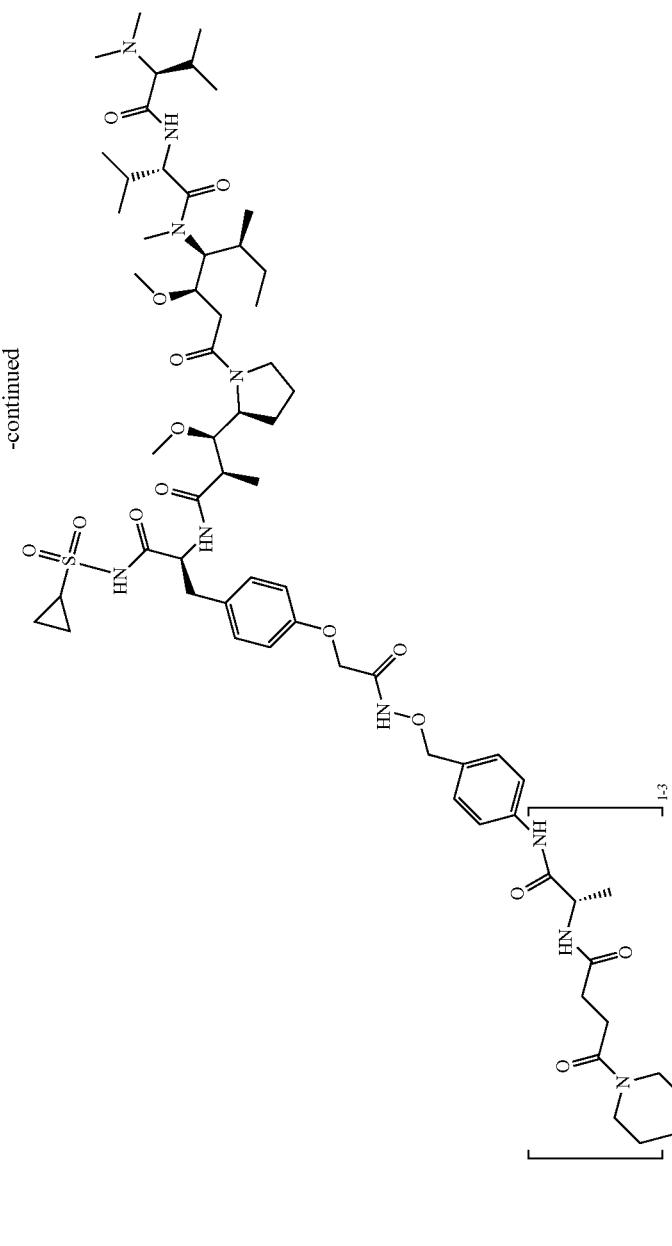
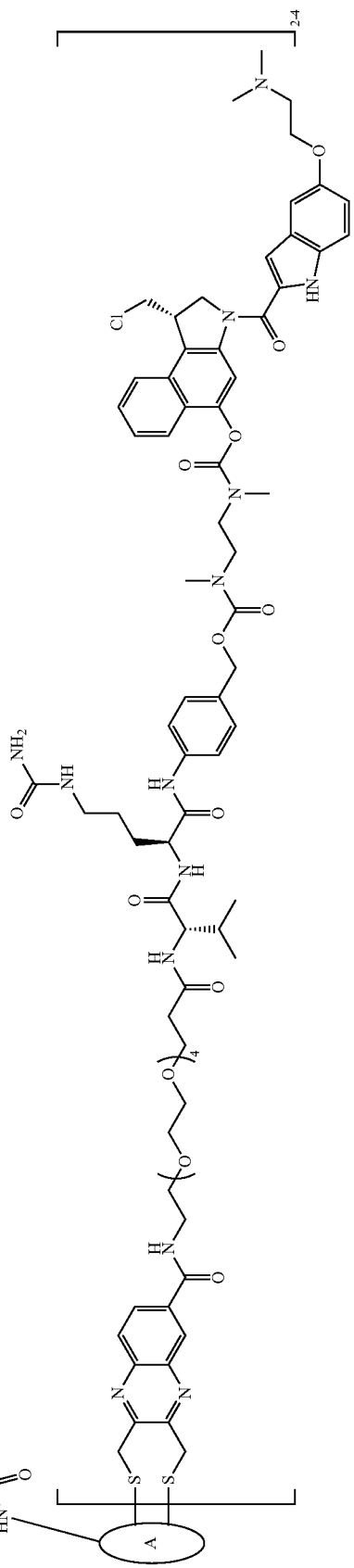

-continued
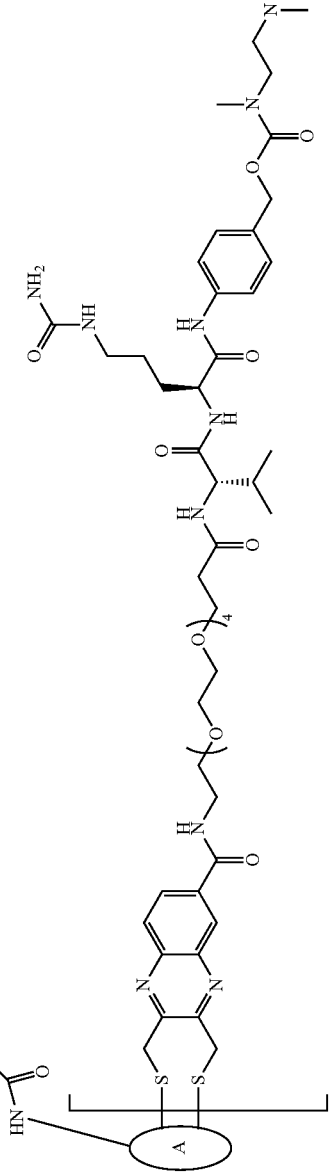

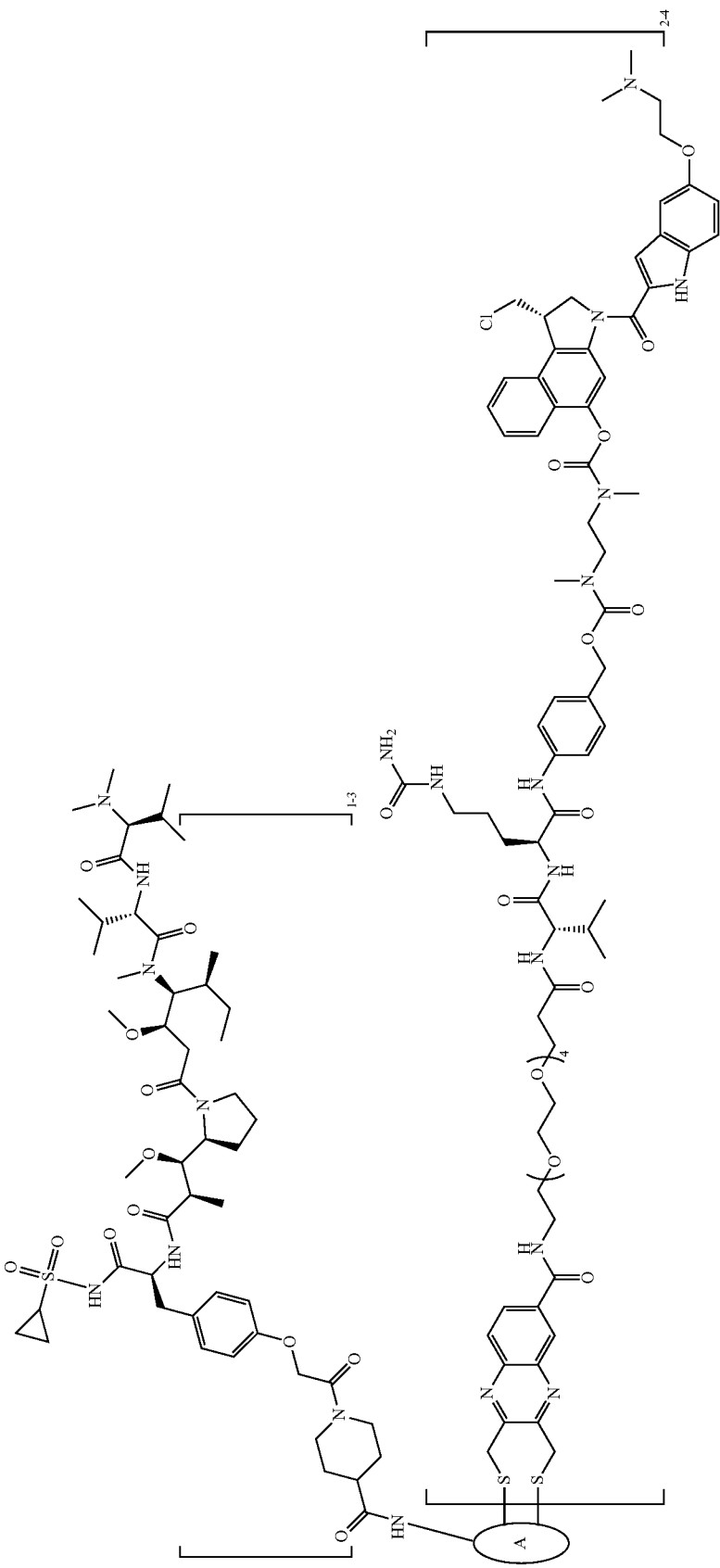

-continued
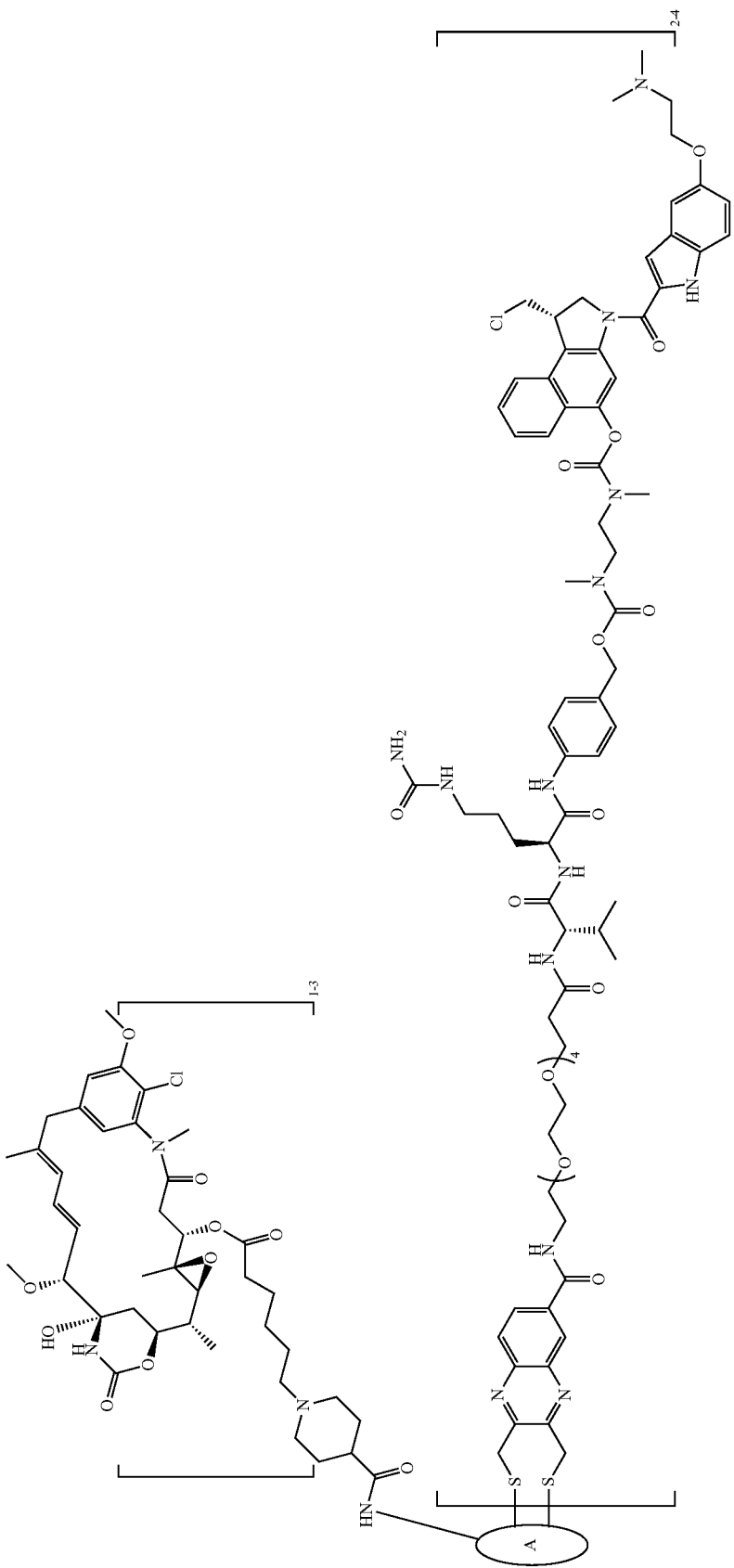

-continued
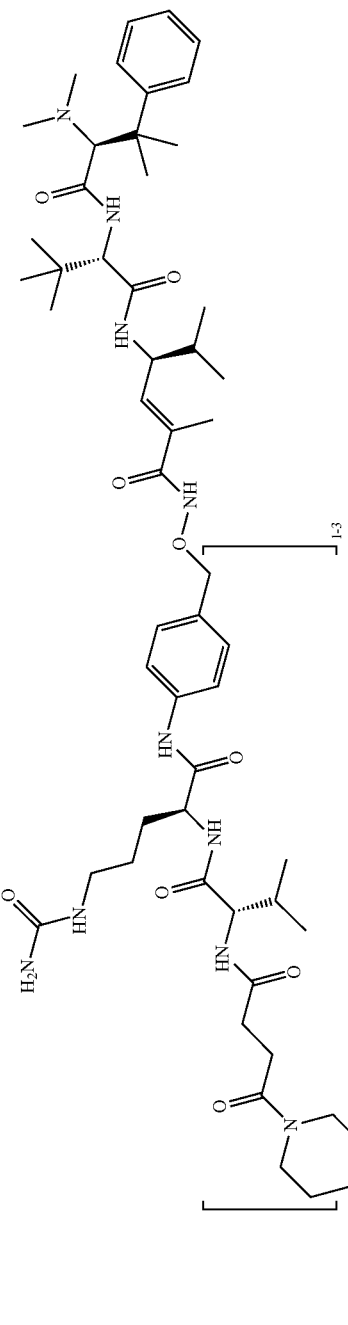
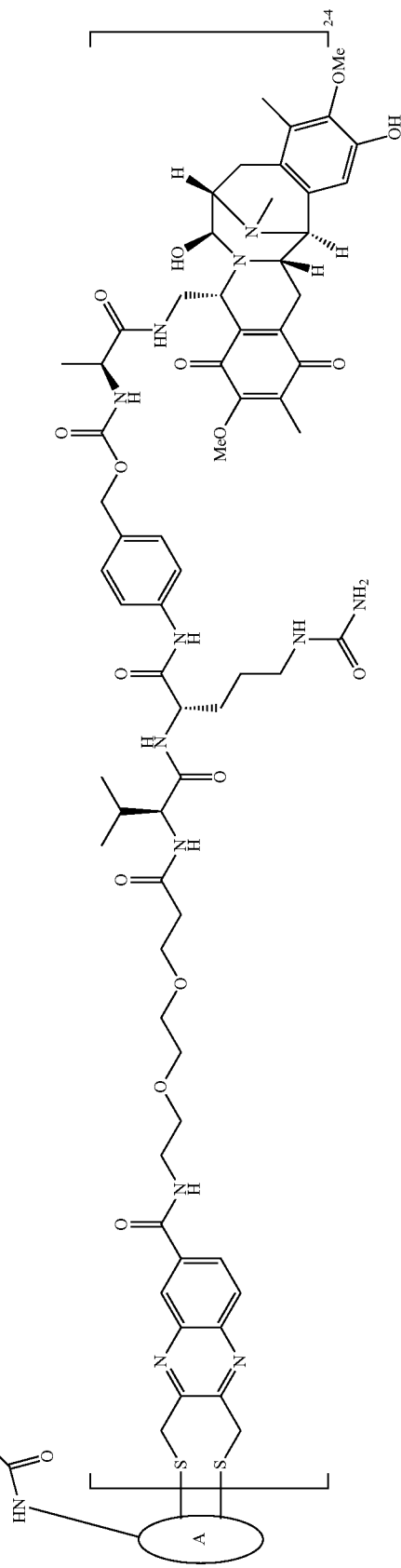

-continued
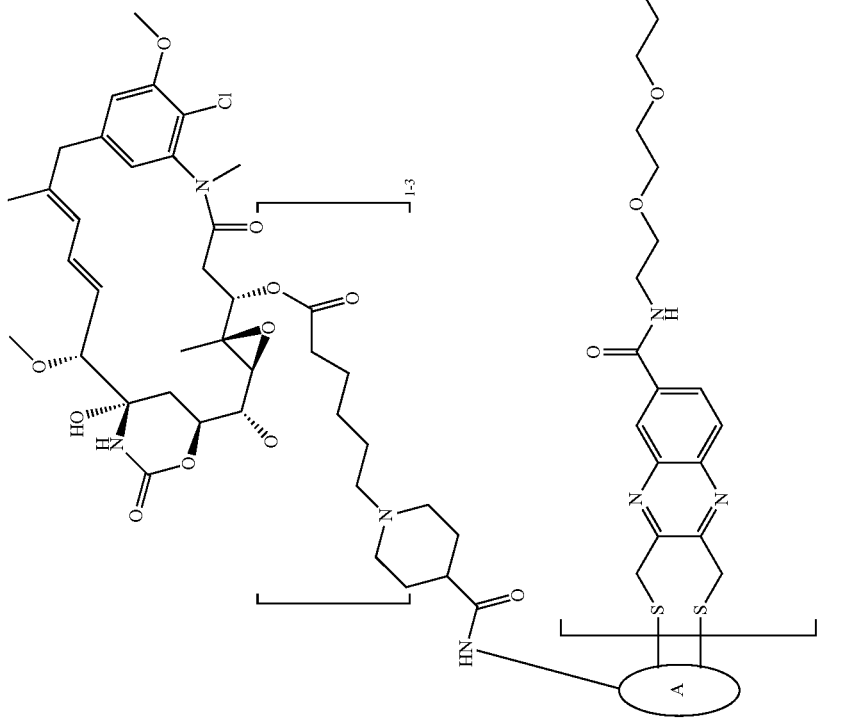

-continued
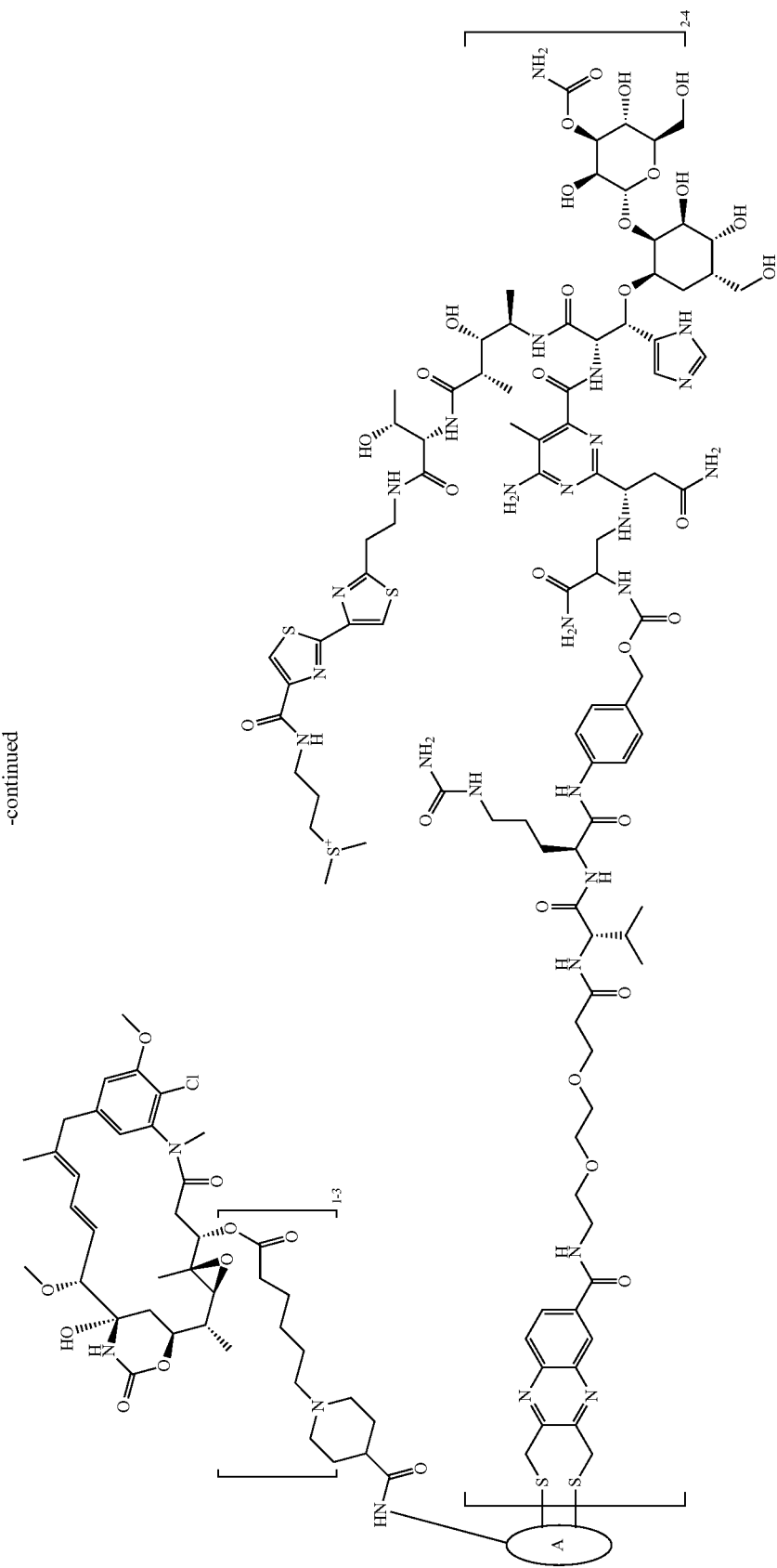

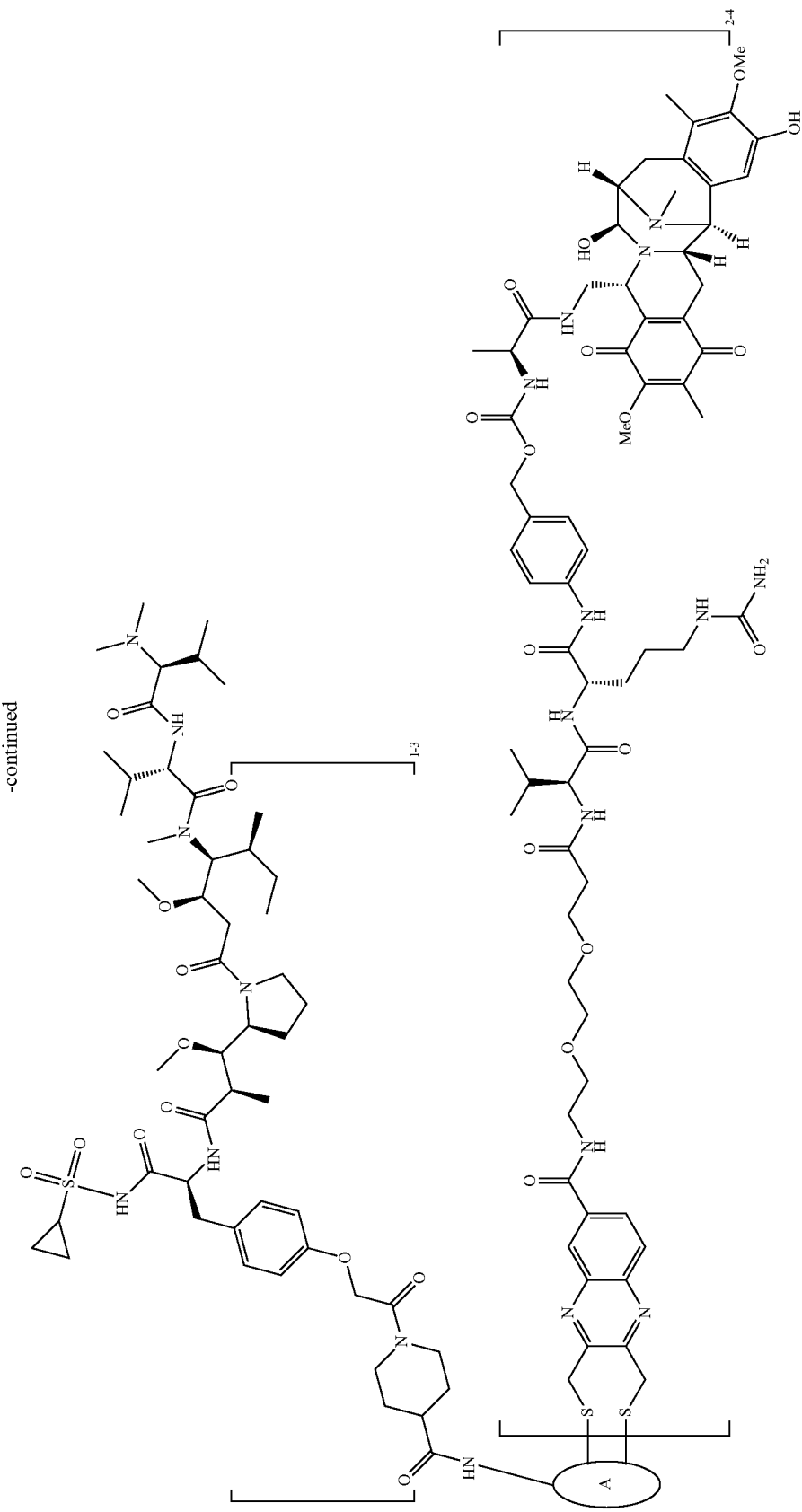

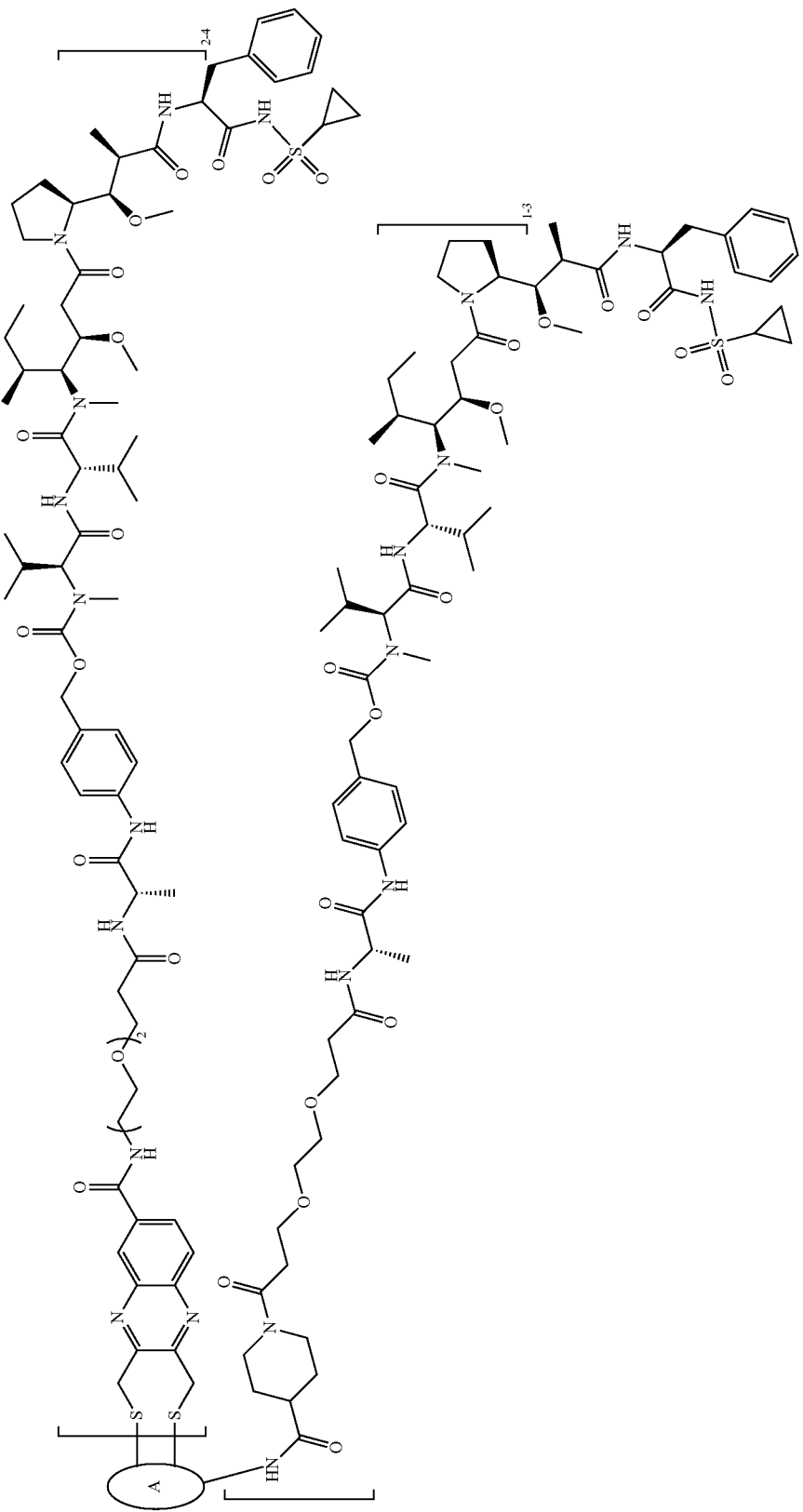

Example 1

This example illustrates the synthesis of compound 3.

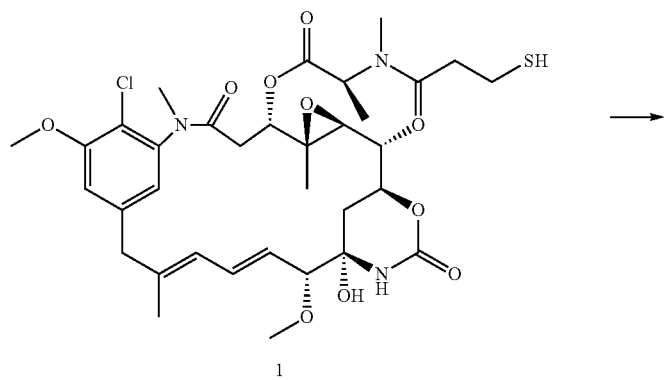

1

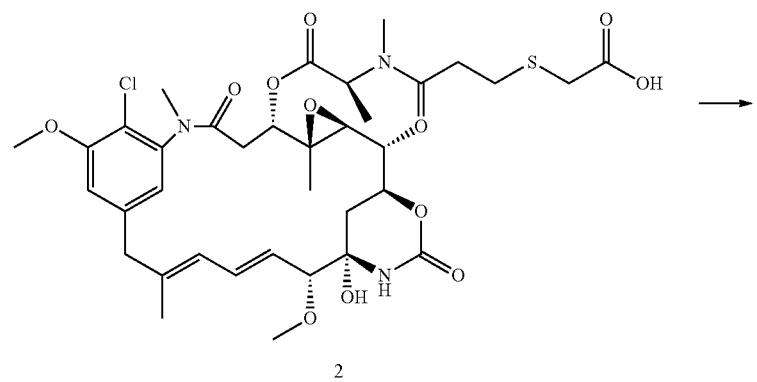

2

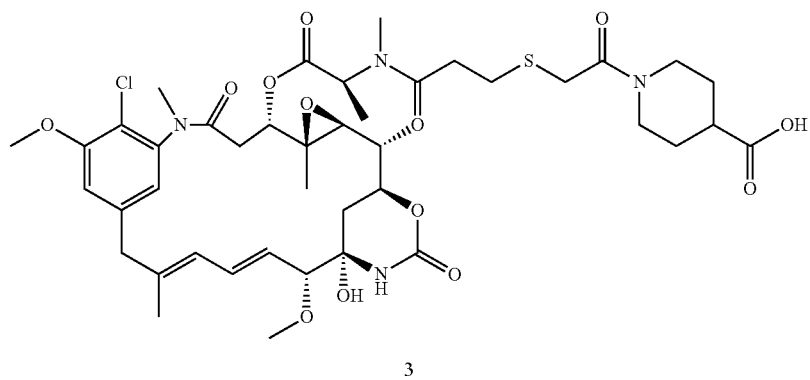

3

To a solution of compound 1 (74 mg, 0.1 mmol) in THF (5 mL) was added bromoacetic acid (70 mg, 5 eq.), followed by aq. saturated NaHCO$_3$ (2 mL). The mixture was stirred at room temperature for 3 h and then acidified with 1N hydrochloric acid. The mixture was extracted with ethyl acetate and the organic layer was dried and concentrated. The crude product was purified by RP-HPLC to give compound 2 as a white powder after lyophilization (72 mg, 91%). MS m/z 795.5 [M+H]$^+$.

Compound 2 (72 mg) was converted to its corresponding NHS ester (General procedure). The NHS ester was dissolved in THF (2 mL). A solution of 4-piperidine carboxylic acid (60 mg) in aq. saturated NaHCO$_3$ (1 mL) was added and the mixture was stirred at room temperature for 1 h. The mixture was then acidified with acetic acid and concentrated to dryness. The residue was purified by RP-HPLC to give compound 3 as a white powder (63 mg). MS m/z 906.6 [M+H]$^+$.

Example 2

This Example Illustrates the Synthesis of Compound 8

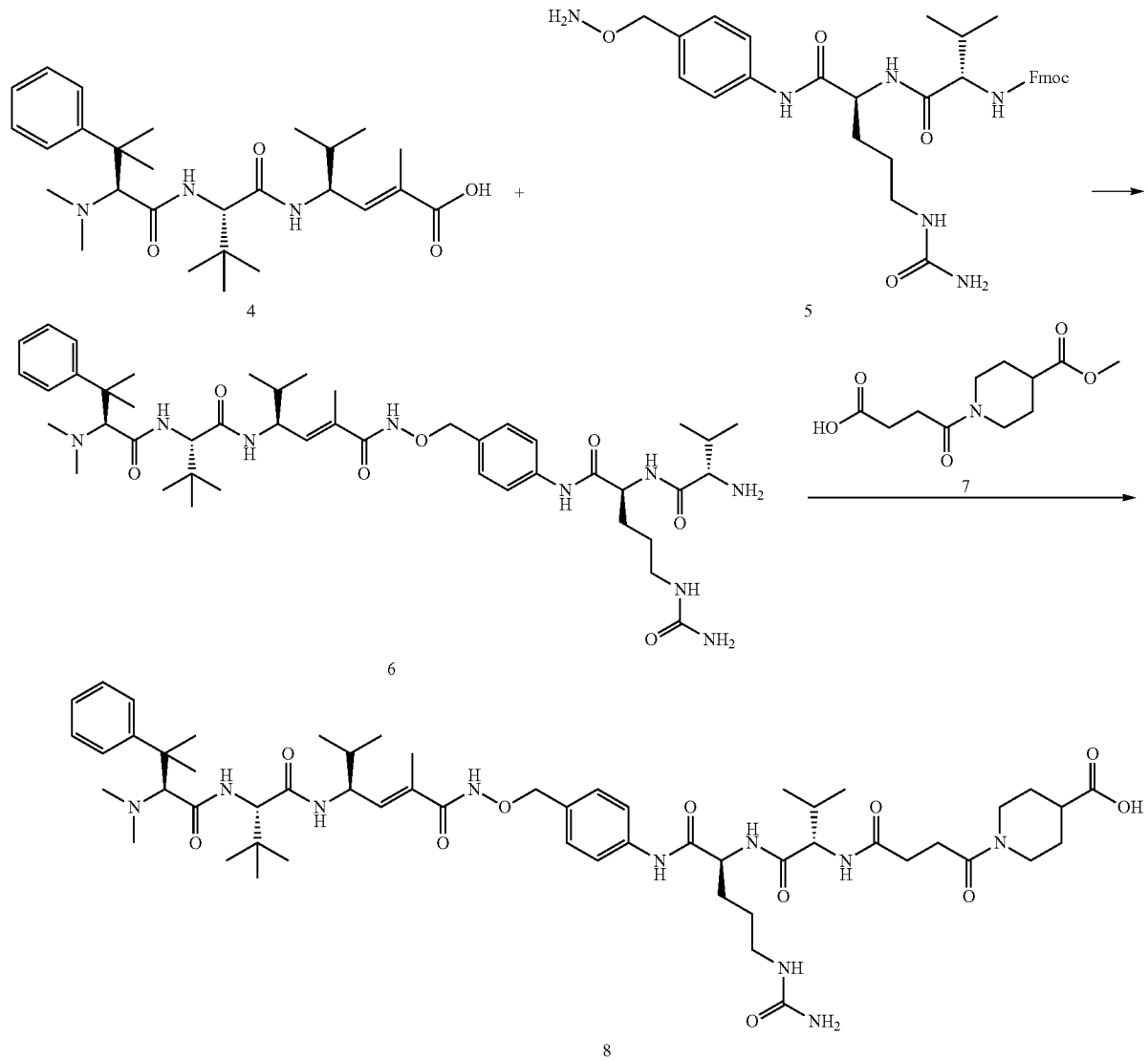

To a stirred solution of compound 4 (95 mg, 0.2 mmol) and compound 5 (TFA salt, 146 mg, 0.2 mmol, prepared as described in WO 2013/173392) in DMF (4 mL) was added DIEA (0.14 mL), followed by HATU (80 mg). After 10 min, piperidine (0.4 mL) was added to the reaction and the mixture was stirred at room temperature for 30 min. The reaction mixture was concentrated and the residue was purified by RP-HPLC to give compound 6 as TFA salt (141 mg, 73%). MS m/z 850.5 [M+H]$^+$.

Compound 6 (141 mg) and 7 (37 mg) were dissolved in DMF (3 mL). DIEA (0.1 mL) was added, followed by HATU (57 mg). The reaction was stirred at room temperature for 30 min 1N solution of aq. NaOH (2 mL) was added and the reaction was stirred at room temperature for 2 h. Acetic acid (0.5 mL) was added to the reaction and the mixture was concentrated. The residue was purified by RP-HPLC to give compound 8 as a white powder (115 mg). MS m/z 1061.5 [M+H]$^+$.

Example 3

TABLE 4
| Compound ID | Structure |
|---|---|
| 9 | 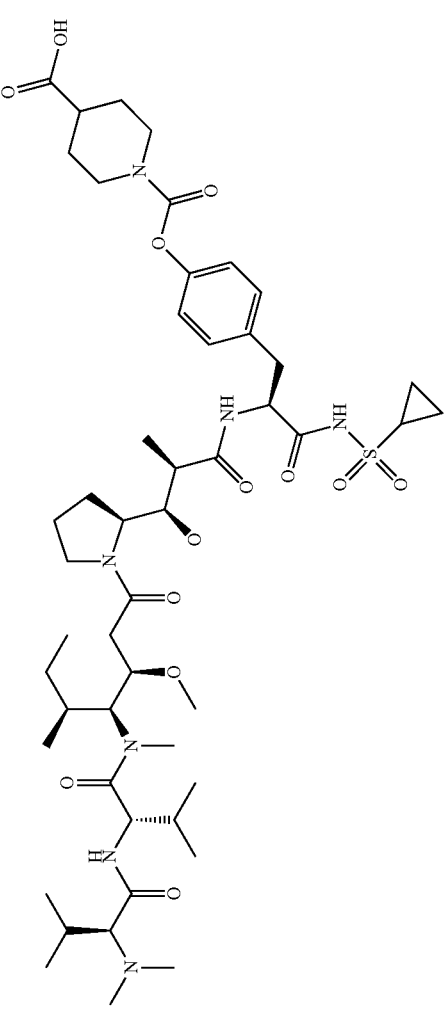 |
| 10 | 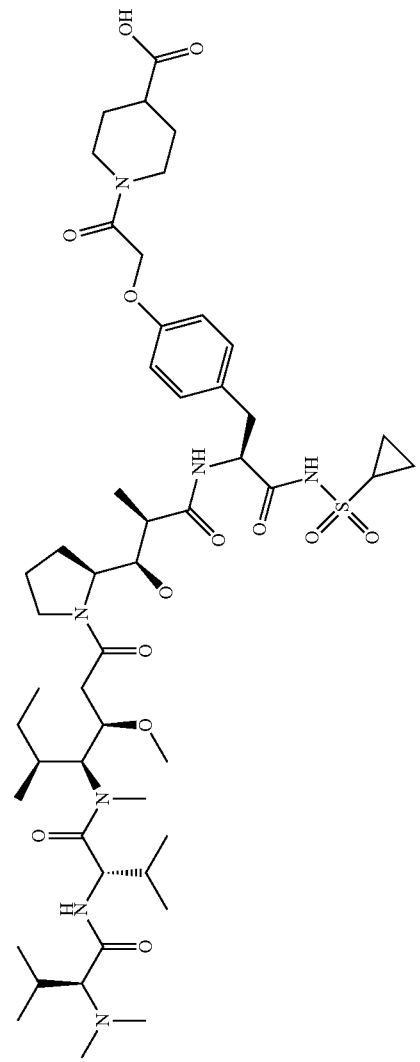 |

TABLE 4-continued
| Compound ID | Structure |
|---|---|
| 11 | 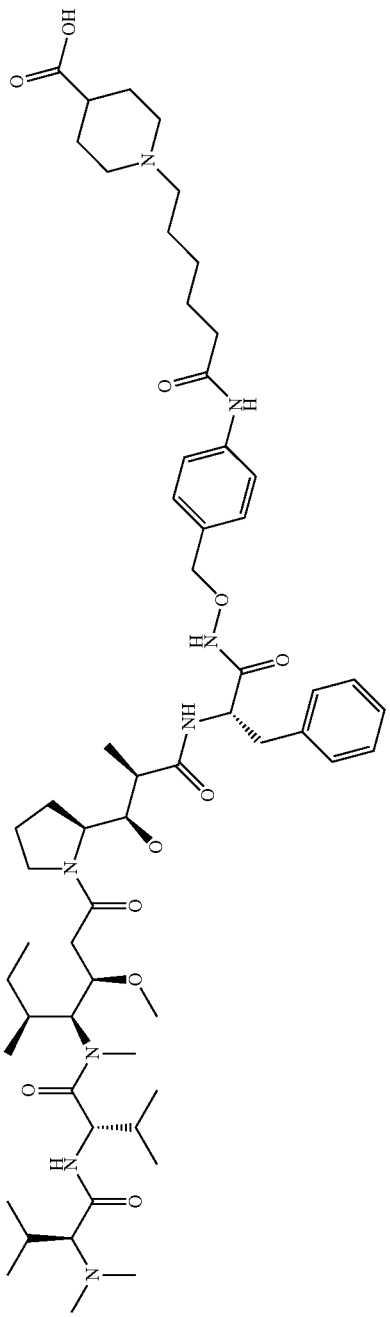 |
| 12 | 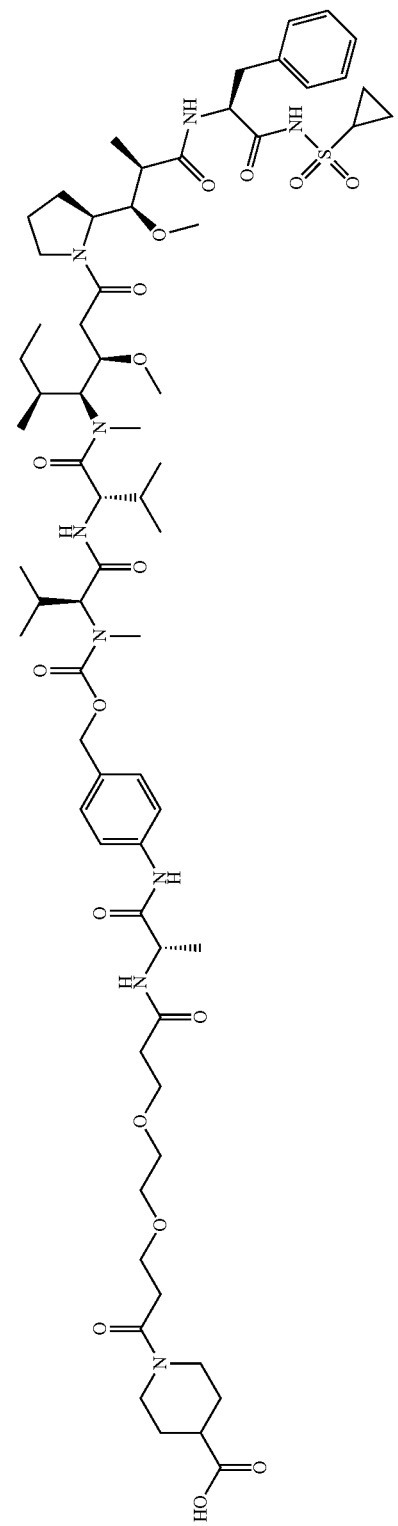 |

TABLE 4-continued
| Compound ID | Structure |
|---|---|
| 13 | 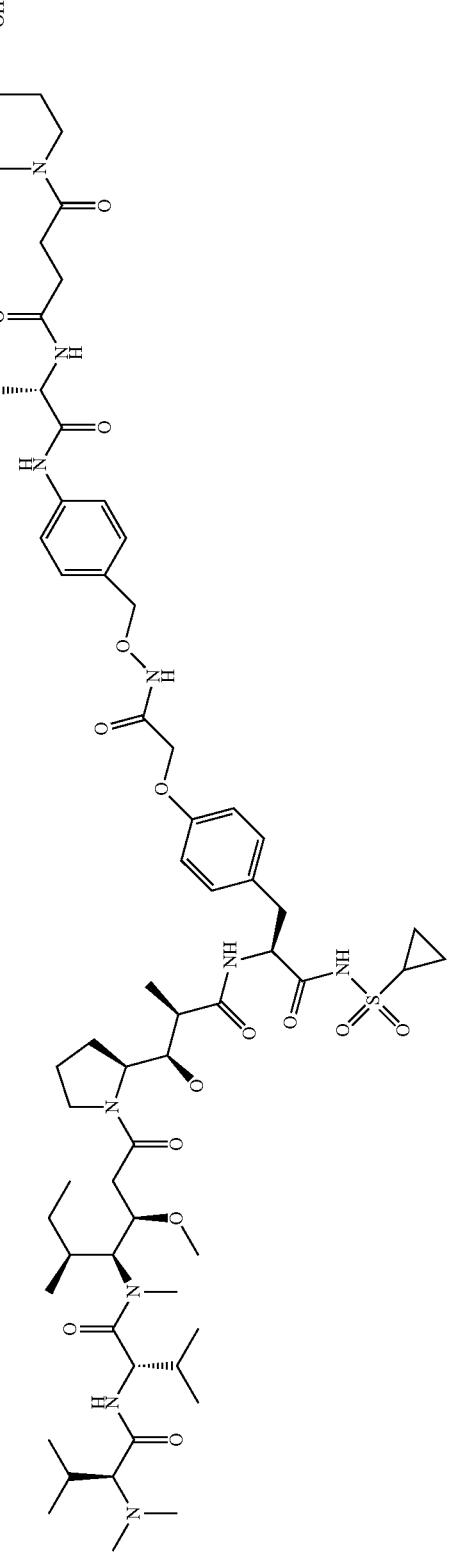 |
| 14 | 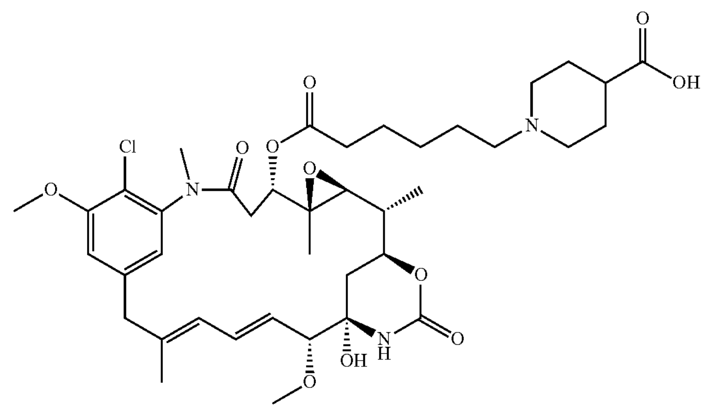 [SMILES: COc1cc2cc(c1Cl)N(C)C(=O)C[C@H](OC(=O)CCCCCN1CCC(C(=O)O)CC1)[C@]1(C)O[C@H]1[C@H](C)[C@@H]1C[C@@](O)(NC(=O)O1)[C@H](OC)/C=C/C=C(\C)C2] |

Compounds 9, 10, 11, 12, 13, and 14 were prepared as described in WO 2013/173392, the disclosure of which is incorporated by reference herein.

Example 4

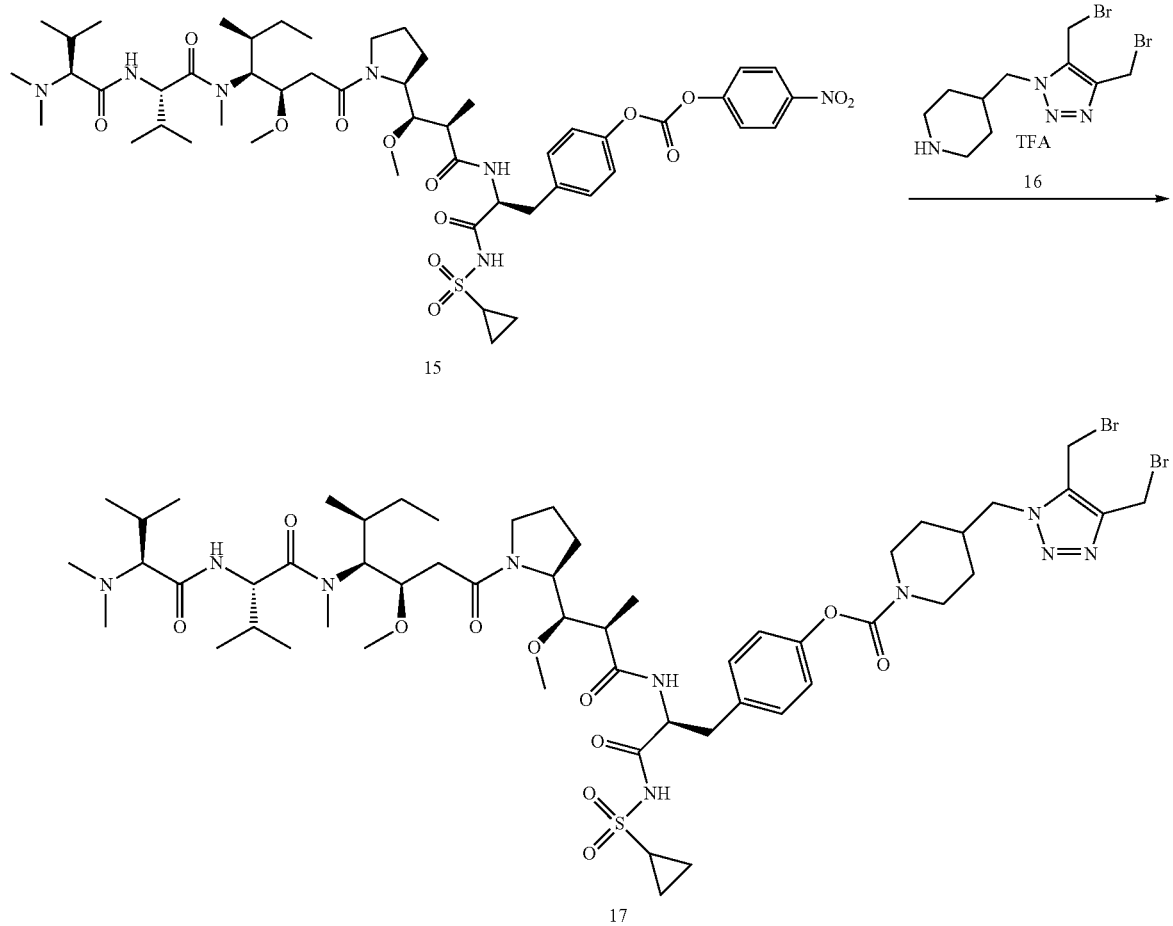

To a solution of compound 15 (0.1 mmol, prepared as described in WO 2013/173392, the disclosure of which is incorporated by reference herein) in THF (3 mL) was added a solution of compound 16 (0.15 mmol, 67 mg) in acetonitrile/water (1/1, v/v, 1 mL), followed by DIEA (50 µL). After 30 min, the reaction was acidified and concentrated. The residue was purified by reverse phase HPLC to give compound 17 as a white solid (87 mg). MS m/z 1243.6 [M+H]$^+$.

Example 5

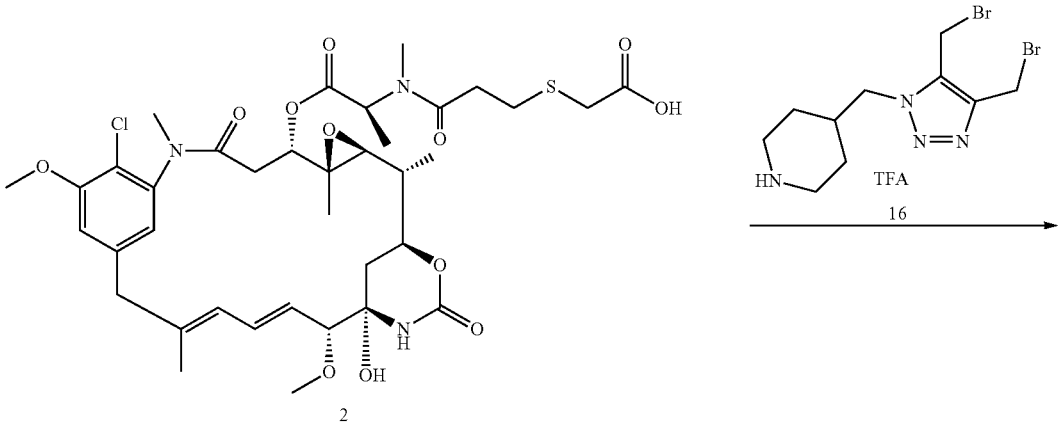

-continued
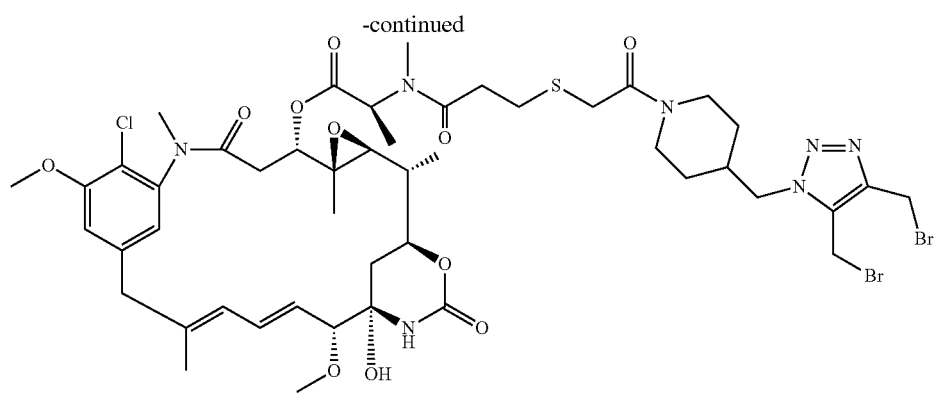
18
Compound 2 (0.1 mmol, 80 mg) and compound 16 (0.1 mmol, 45 mg) were dissolved in DCM/DMF (10/1, v/v, 3 mL). DIEA (20 μL) was added, followed by DIC (25 μL). The mixture was stirred at room temperature for 10 min DCM was evaporated and the residue was purified by reverse phase HPLC to give compound 18 as a white powder (66 mg, 53%). MS m/z 1130.6 [M+H]$^+$.
Example 6

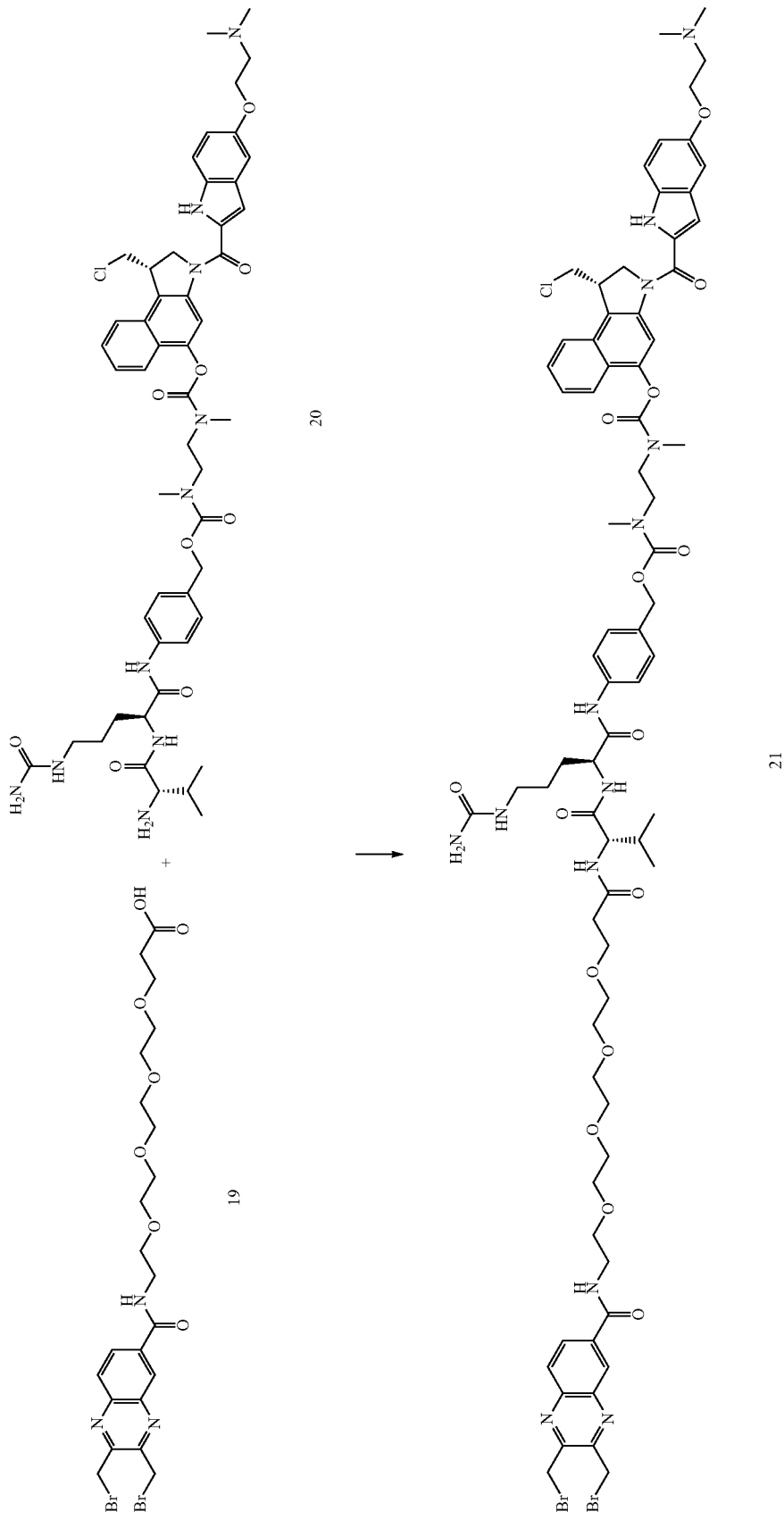

Compound 19 (0.06 mmol, 36 mg) and compound 20 (0.05 mmol, 60 mg, TFA salt) were dissolved in DCM/DMF (4/1, v/v, 3 mL). DIEA (25 μL) was added, followed by DIC (15 μL). The mixture was stirred at room temperature for 10 min DCM was evaporated and the residue was purified by reverse phase HPLC to give compound 21 as a white powder (41 mg, 49%). MS m/z 1572.8 $[M+H]^+$.

Example 7

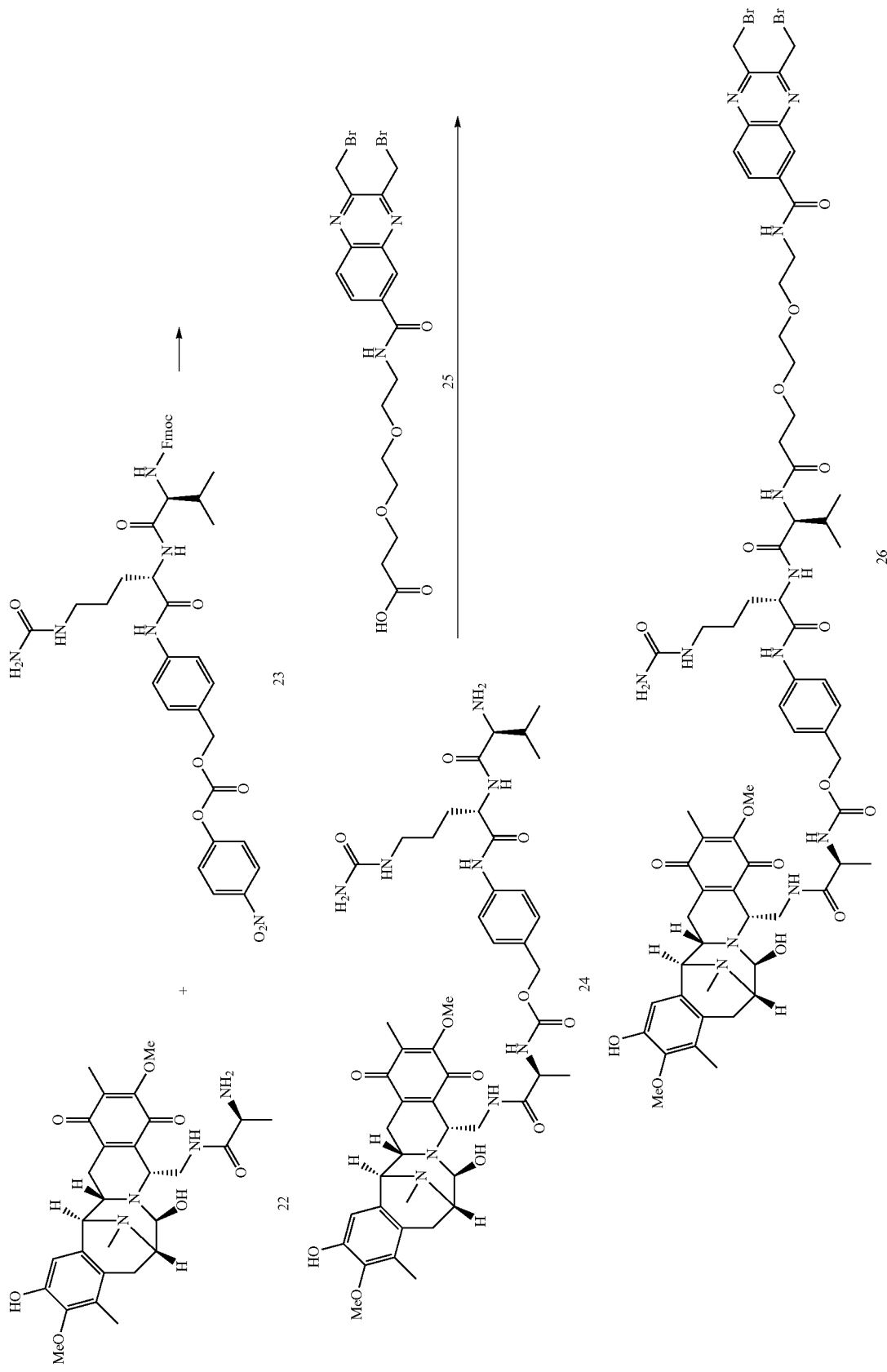

To a solution of compound 22 (54 mg, 0.1 mmol) in anhydrous DMF (3 mL) was added compound 23 (80 mg) and DIEA (20 μL). The mixture was stirred at room temperature for 2 h. Piperidine (40 μL) was added. After 3 h, the mixture was added dropwise to 100 mL of ether under vigorous stirring. The precipitated solid was collected and purified by reverse phase HPLC to give compound 24 as a yellow solid (75 mg). MS m/z 947.3 [M+H]$^+$.

Compound 24 (75 mg) and compound 25 (42 mg) were dissolved in DCM/DMF (4/1, v/v, 3 mL). DIEA (20 μL) was added, followed by DIC (20 μL). The mixture was stirred at room temperature for 20 min. DCM was evaporated and the residue was purified by reverse phase HPLC to give compound 26 as a yellow powder (48 mg). MS m/z 1447.5 [M+H]$^+$.

Example 8

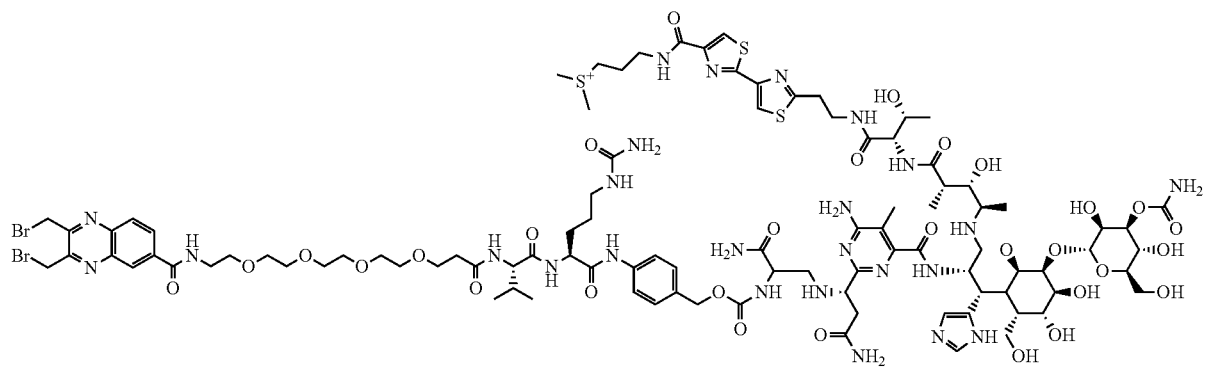

27

Compound 27 was synthesized from Bleomycin using the same procedure as described for compound 26. MS m/z 2320.8 [M+H]$^+$.

Example 9

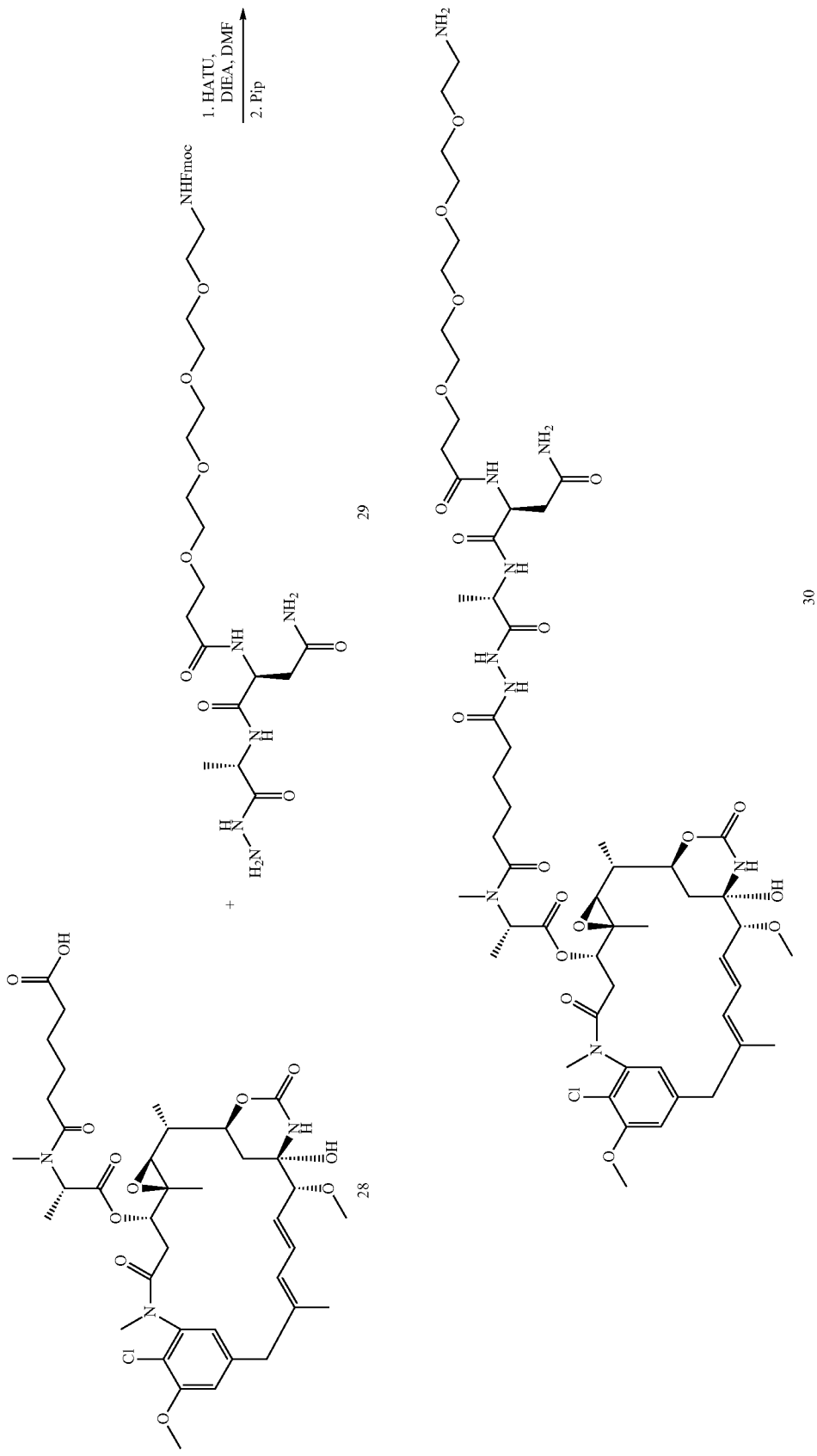

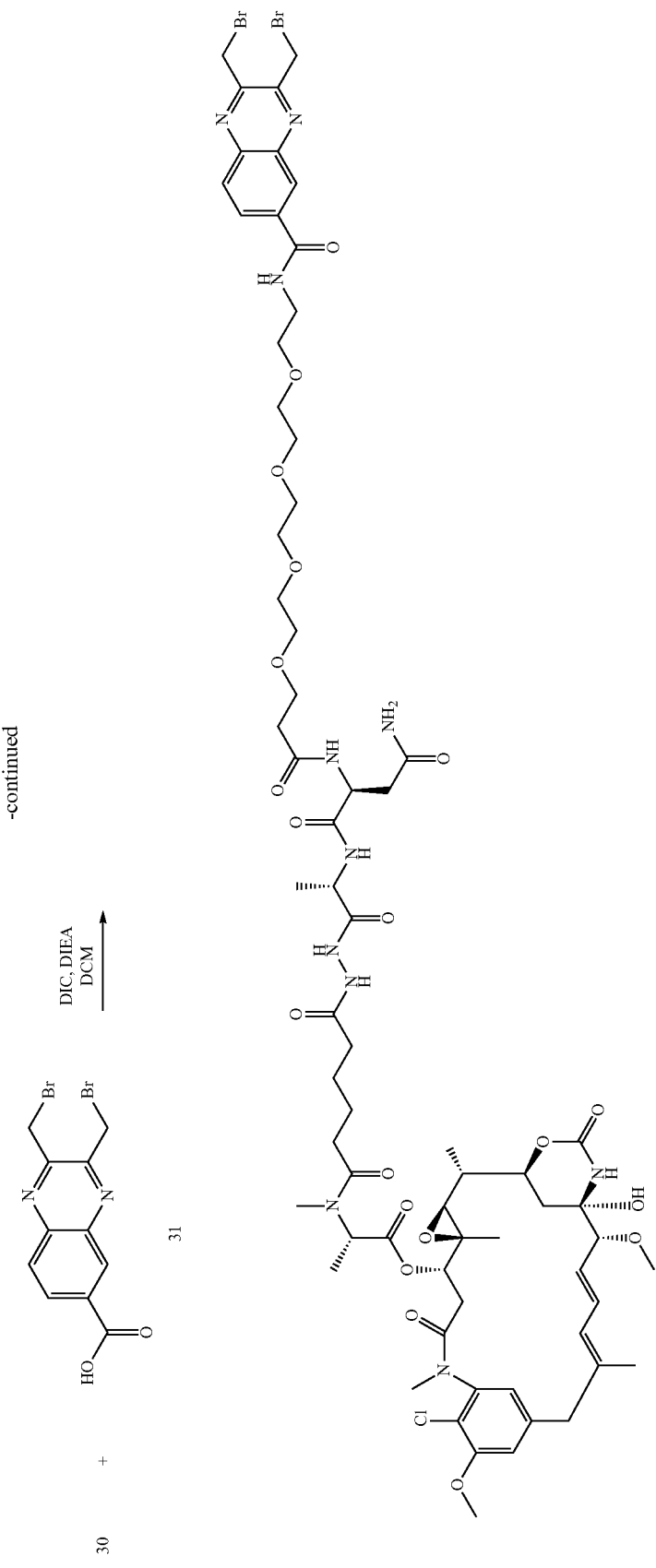

Preparation of compound 30: To a solution of compound 28 (97 mg, 0.125 mmol) in 3 mL of DMF was added HATU (48 mg, 0.125 mmol), DIEA (52 mg, 0.4 mmol), and compound 29 (100 mg, 0.125 mmol). After 1 h, to the mixture was added piperidine (300 uL) and the mixture was stirred for 10 min. Then the mixture was evaporated and purified by HPLC to give compound 30 (83 mg, 50%). MS m/z 1224.5 (M+H).

Preparation of compound 32: To a solution of compound 30 (26 mg, 0.074 mmol) in 1 mL of DCM was added DIC (46 mg, 0.037 mmol). After 10 min, a solution of compound 31 (41 mg, 0.031 mmol) and DIEA (17 µL) in 2 mL of DCM was added and the mixture was stirred for 30 min. The solvent was evaporated under vacuum and the residue was purified by HPLC to give compound 32 (30 mg, 63%). MS m/z 1554.4 (M+H).

Example 10

Preparation of Compound 10

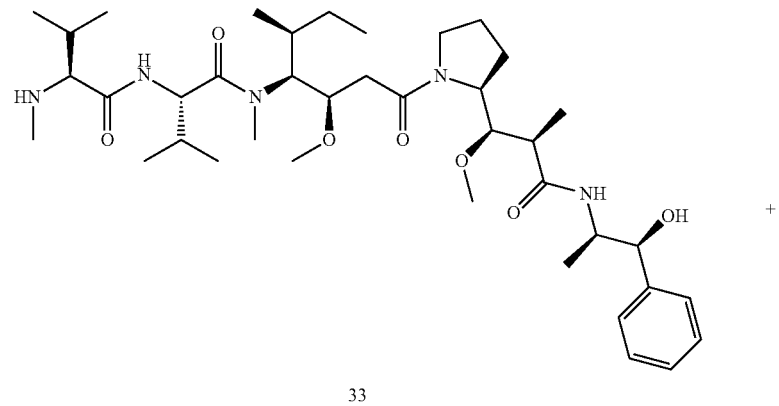

33

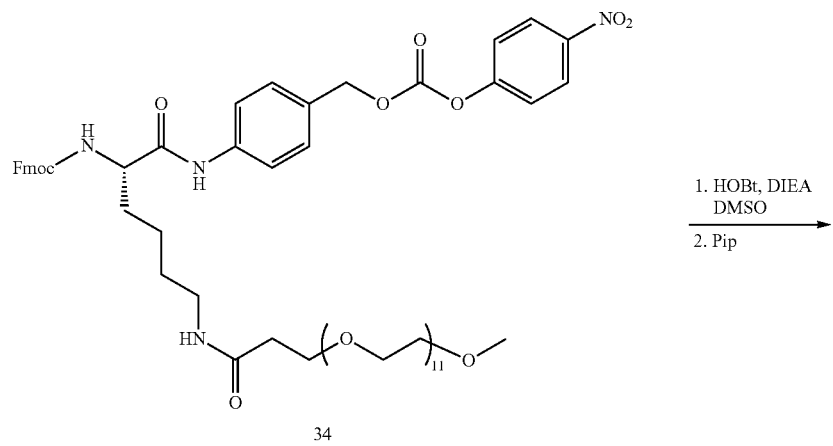

34

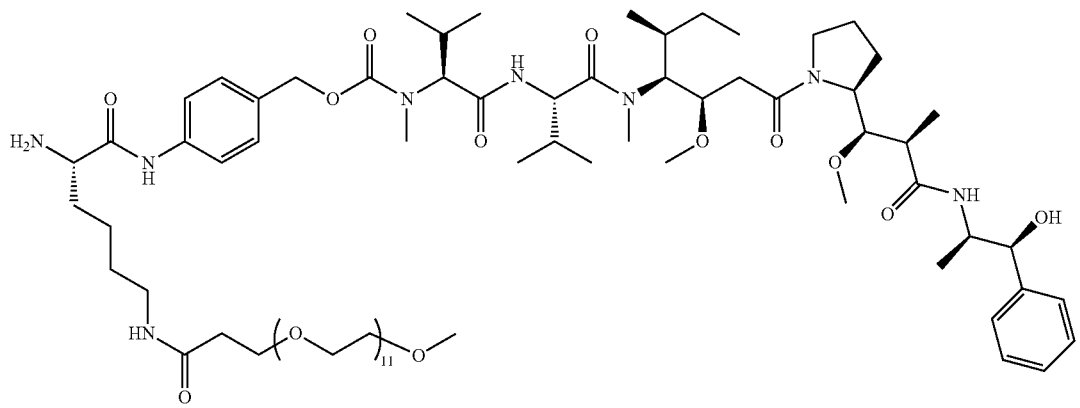

35

-continued

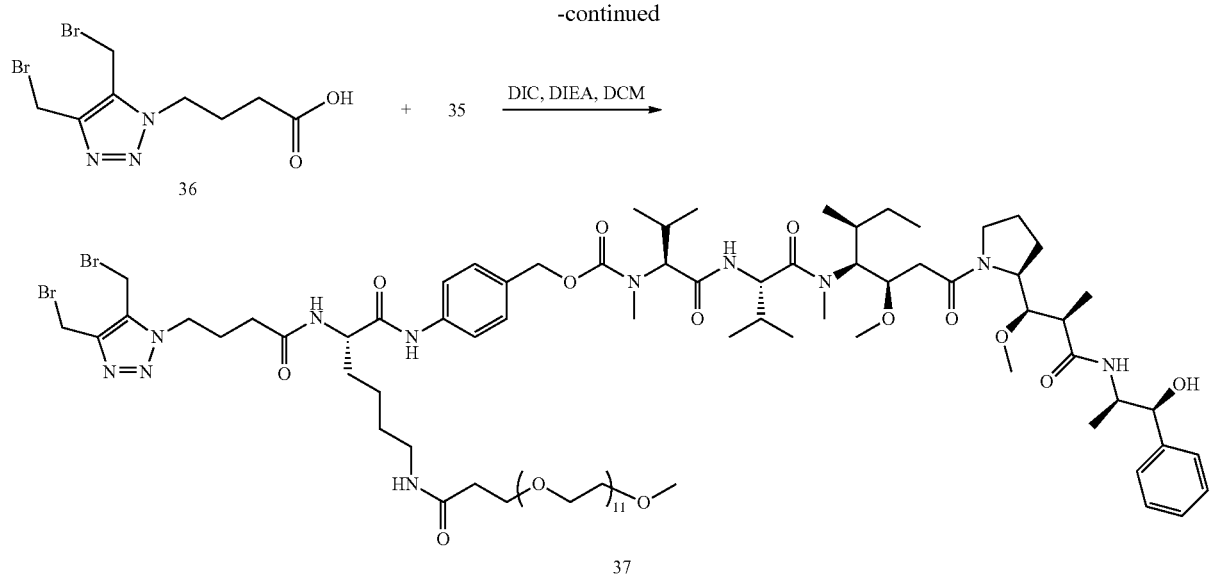

Preparation of compound 35: To a solution of compound 33 (64 mg, 0.077 mmol) in 3 mL of DMF was added 34 (97 mg, 0.077 mmol), HOBt (5 mg, 0.04 mmol) and DIEA (13 mg, 0.1 mmol). After 24 h, reaction was done by HPLC, and 300 μL of piperidine was added. After 1 h, the mixture was purified by HPLC to give compound 35 (76 mg, 62%). MS m/z 1607.7 (M+H).

was added and the mixture was stirred for 30 min. The solvent was evaporated under vacuum and the residue was purified by HPLC to give compound 37 (60 mg, 69%). MS m/z 1930.6 (M+H).

Example 11

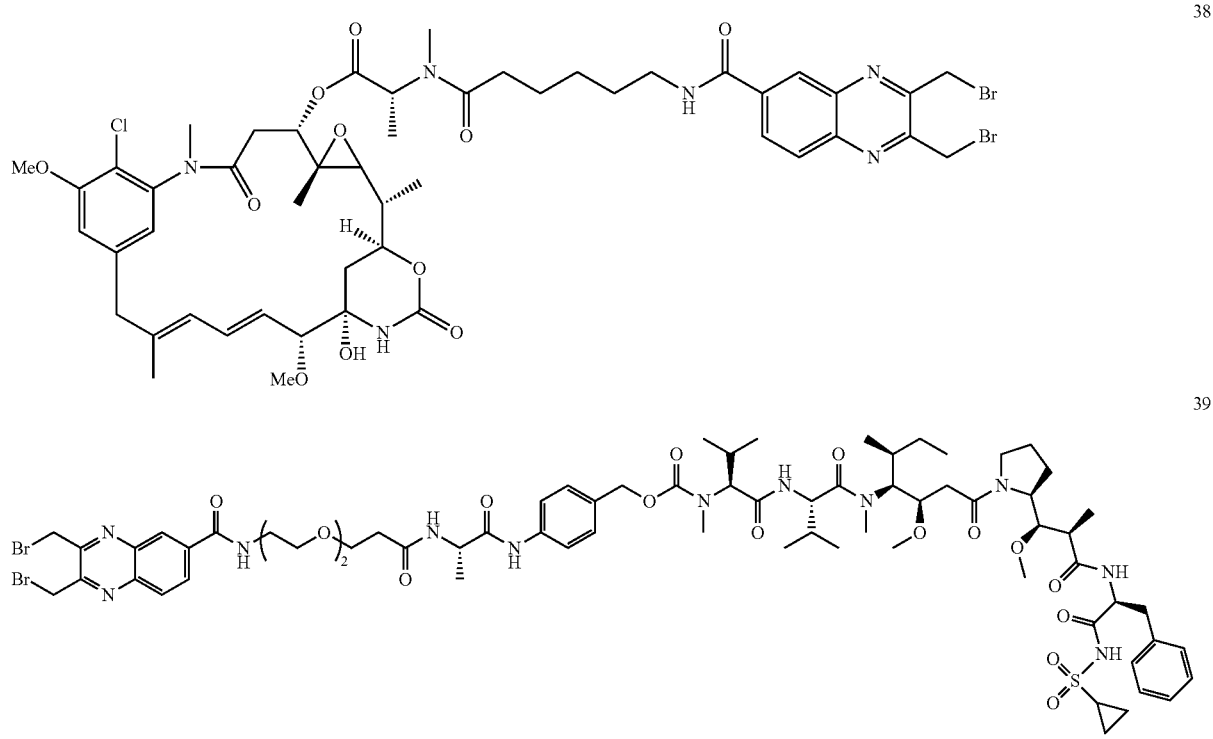

Preparation of compound 37: To a solution of compound 36 (31 mg, 0.09 mmol) in 1 mL of DCM was added DIC (60 mg, 0.045 mmol). After 10 min, a solution of compound 35 (77 mg, 0.045 mmol) and DIEA (25 μL) in 2 mL of DCM Compounds 38 and 39 were prepared as described in WO 2013/173391, the disclosure of which is incorporated by reference herein.

Example 12

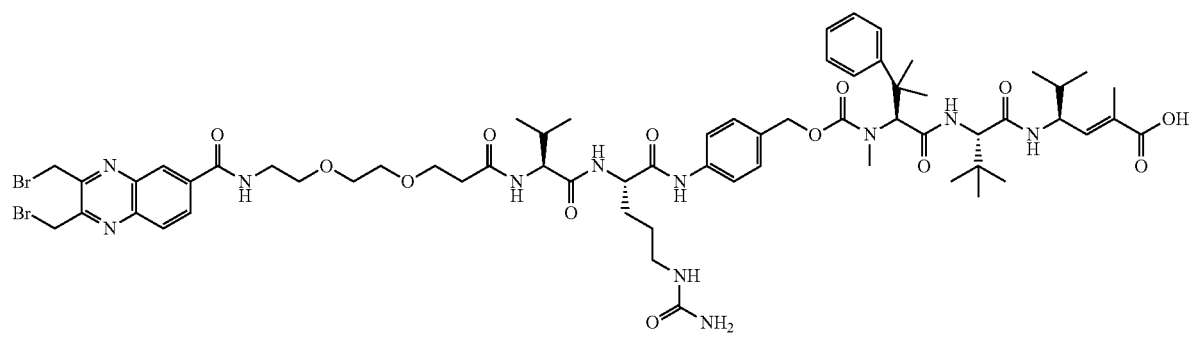

40

Compound 40 was synthesized from compound HTI-286 using the same procedure as described for compound 26. MS m/z 1366.7 [M+H]$^+$.

Example 13

This example provides the results of EC50 assays of the designated dual drug conjugated antibodies measured in vitro in specified cells.

TABLE 5.1

| Dual conjugated ADC | Cytotoxic activity EC50 (nM) | | | | | | |
|---|---|---|---|---|---|---|---|
| | SKBR-3 | HCC1954 | BT474 | MDA-MB-175 | SKOV_3 | MCF-7 | MDA-468 |
| A-9-38 | 0.057 | 0.072 | N/D | N/D | N/D | >100 | >100 |
| A-3-17 | N/D | N/D | 0.188 | 0.322 | N/D | 16.08 | 23.5 |
| A-11-21 | 0.67 | 0.136 | 31.99 | N/D | 0.537 | 34.01 | 37.52 |
| A-12-38 | 0.062 | 0.036 | N/D | N/D | N/D | >100 | >100 |
| A-10-38 | 0.081 | 0.1 | N/D | N/D | N/D | >100 | >100 |
| A-13-38 | 0.066 | 0.04 | N/D | N/D | N/D | >100 | >100 |
| A-13-21 | N/D | N/D | >100 | N/D | 0.4 | N/D | N/D |
| A-8-21 | 0.12 | 0.1711 | 10.74 | N/D | 1.986 | >100 | 48.61 |
| A-10-21 | 0.03 | 0.039 | N/D | N/D | N/D | >100 | 32.72 |
| A-14-21 | >100 | 0.509 | N/D | N/D | N/D | >100 | >100 |
| A-14-27 | >100 | >100 | N/D | N/D | N/D | >100 | >100 |
| A-12-39 | 0.028 | 0.024 | 0.132 | N/D | 0.326 | 5.816 | >100 |
| A-9 | 0.041 | 0.138 | 0.423 | 3.635 | 0.405 | >100 | >100 |
| A-3 | 0.055 | 0.16 | >100 | 3.669 | 1.716 | 17.84 | 24.85 |
| A-11 | 0.046 | 0.04 | 0.219 | N/D | 0.518 | 14.3 | 6.486 |
| A-12 | 0.047 | 0.03 | 0.2 | N/D | 0.388 | >100 | >100 |
| A-10 | 0.015 | 0.008 | N/D | N/D | N/D | >100 | >100 |
| A-13 | 0.028 | 0.014 | 0.169 | N/D | 0.307 | >100 | >100 |
| A-21 | 0.074 | 0.586 | 9.325 | N/D | 0.841 | >100 | 53.53 |
| A-8 | >100 | >100 | N/D | N/D | N/D | >100 | >100 |
| A-38 | 0.626 | 0.81 | N/D | N/D | N/D | >100 | >100 |
| A-27 | >100 | >100 | N/D | N/D | N/D | >100 | >100 |
| A-39 | 0.038 | 0.023 | 0.093 | N/D | 0.225 | >100 | >100 |
| A-17 | N/D | N/D | 0.153 | 0.186 | N/D | >100 | >100 |

TABLE 5.2

| Dual conjugated ADC | Cytotoxic activity EC50 (nM) | | | | | |
|---|---|---|---|---|---|---|
| | SKBR-3 | HCC1954 | BT474 | MDA-MB-175 | SKOV_3 | MCF-7 |
| A-9-38 | 0.057 | 0.072 | N/D | N/D | N/D | >100 |
| A-3-17 | N/D | N/D | 0.188 | 0.322 | N/D | 16.08 |
| A-11-21 | 0.67 | 0.136 | 31.99 | N/D | 0.537 | 34.01 |
| A-12-38 | 0.062 | 0.036 | N/D | N/D | N/D | >100 |
| A-10-38 | 0.081 | 0.1 | N/D | N/D | N/D | >100 |
| A-13-38 | 0.066 | 0.04 | N/D | N/D | N/D | >100 |
| A-13-21 | N/D | N/D | >100 | N/D | 0.4 | N/D |
| A-8-21 | 0.12 | 0.1711 | 10.74 | N/D | 1.986 | >100 |
| A-10-21 | 0.03 | 0.039 | N/D | N/D | N/D | >100 |
| A-14-21 | >100 | 0.509 | N/D | N/D | N/D | >100 |
| A-14-27 | >100 | >100 | N/D | N/D | N/D | >100 |
| A-12-39 | 0.028 | 0.024 | 0.132 | N/D | 0.326 | 5.816 |
| A-9 | 0.041 | 0.138 | 0.423 | 3.635 | 0.405 | >100 |
| A-3 | 0.055 | 0.16 | >100 | 3.669 | 1.716 | 17.84 |
| A-11 | 0.046 | 0.04 | 0.219 | N/D | 0.518 | 14.3 |
| A-12 | 0.047 | 0.03 | 0.2 | N/D | 0.388 | >100 |
| A-10 | 0.015 | 0.008 | N/D | N/D | N/D | >100 |
| A-13 | 0.028 | 0.014 | 0.169 | N/D | 0.307 | >100 |
| A-21 | 0.074 | 0.586 | 9.325 | N/D | 0.841 | >100 |
| A-8 | >100 | >100 | N/D | N/D | N/D | >100 |
| A-38 | 0.626 | 0.81 | N/D | N/D | N/D | >100 |
| A-27 | >100 | >100 | N/D | N/D | N/D | >100 |
| A-39 | 0.038 | 0.023 | 0.093 | N/D | 0.225 | >100 |
| A-17 | N/D | N/D | 0.153 | 0.186 | N/D | >100 |

TABLE 5.3

| Dual conjugated ADC | Cytotoxic activity EC50 (nM) | | | | | |
|---|---|---|---|---|---|---|
| | SKBR-3 | HCC1954 | BT474 | MDA-MB-175 | SKOV_3 | MCF-7 |
| A-9-38 | 0.057 | 0.072 | N/D | N/D | N/D | >100 |
| A-3-17 | N/D | N/D | 0.188 | 0.322 | N/D | 16.08 |
| A-11-21 | 0.67 | 0.136 | 31.99 | N/D | 0.537 | 34.01 |
| A-12-38 | 0.062 | 0.036 | N/D | N/D | N/D | >100 |
| A-10-38 | 0.081 | 0.1 | N/D | N/D | N/D | >100 |
| A-13-38 | 0.066 | 0.04 | N/D | N/D | N/D | >100 |
| A-13-21 | N/D | N/D | >100 | N/D | 0.4 | N/D |
| A-8-21 | 0.12 | 0.1711 | 10.74 | N/D | 1.986 | >100 |
| A-10-21 | 0.03 | 0.039 | N/D | N/D | N/D | >100 |
| A-14-21 | >100 | 0.509 | N/D | N/D | N/D | >100 |
| A-14-27 | >100 | >100 | N/D | N/D | N/D | >100 |
| A-12-39 | 0.028 | 0.024 | 0.132 | N/D | 0.326 | 5.816 |

TABLE 5.4

| Dual conjugated ADC | Cytotoxic activity EC50 (nM) | | | | | | |
|---|---|---|---|---|---|---|---|
| | SKBR-3 | HCC1954 | BT474 | MDA-MB-175 | SKOV_3 | MCF-7 | MDA-468 |
| A-9-38 | 0.057 | 0.072 | N/D | N/D | N/D | >100 | >100 |
| A-3-17 | N/D | N/D | 0.188 | 0.322 | N/D | 16.08 | 23.5 |
| A-11-21 | 0.67 | 0.136 | 31.99 | N/D | 0.537 | 34.01 | 37.52 |
| A-12-38 | 0.062 | 0.036 | N/D | N/D | N/D | >100 | >100 |
| A-10-38 | 0.081 | 0.1 | N/D | N/D | N/D | >100 | >100 |
| A-13-38 | 0.066 | 0.04 | N/D | N/D | N/D | >100 | >100 |
| A-13-21 | N/D | N/D | >100 | N/D | 0.4 | N/D | N/D |
| A-8-21 | 0.12 | 0.1711 | 10.74 | N/D | 1.986 | >100 | 48.61 |
| A-10-21 | 0.03 | 0.039 | N/D | N/D | N/D | >100 | 32.72 |
| A-14-21 | >100 | 0.509 | N/D | N/D | N/D | >100 | >100 |
| A-14-27 | >100 | >100 | N/D | N/D | N/D | >100 | >100 |
| A-12-39 | 0.028 | 0.024 | 0.132 | N/D | 0.326 | 5.816 | >100 |

Example 14

This example provides a description of the comparative activity data provided in the Figures. On the first day, a specific tumor cell line, such as SKBR-3, was plated at 20-30% confluence in 100 µl culture medium on a 96 well culture plate (Corning). The cells were incubated in a $CO_2$ incubator at 37° C. overnight. On second day, a dual conjugate ADC, such as A-3-17, was serially diluted to the culture medium at 19:60 ratio, with starting concentration of 100 nM. 5 µl of the serially diluted conjugates were added to the 96 well plate containing SKRB-3 cells. SKBR-3 cells with dual conjugate ADC, A-3-17 were incubated at 37° C. for 72 hours. The viability of tumor cell treated with dual conjugate ADC, A-3-17 was then measured using a cell viability kit, CelltitreGlo (Promega G-7573) according to the manufacturer protocol on a plate reader (SpectraMax L from Molecular device). The $IC_{50}$ value, 50% inhibition of cell growth was calculated using a curve fitting software, Graphpad Prism.

FIG. 1 shows anti-Her-2 (A) dual conjugates (K-lock+C-lock) induces enhanced antiproliferative effect in breast cancer cell lines, compared to either single K-lock or C-lock conjugates. A, SKBR-3 (HER2 3+), B, HCC1954 (HER2 3+), C, MCF-7 (HER2+/−), were all treated with either single conjugates or dual conjugates for 3 d. $IC_{50}$ was determined for the concentration that showed 50% inhibition of cell growth.

Figure 2:
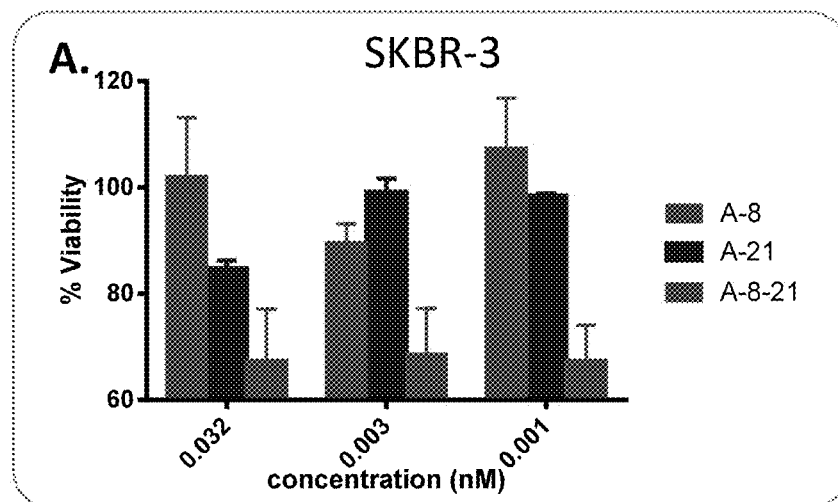
FIG. 2 shows anti-Her-2 (A) dual conjugates (K-lock+C-lock) induces enhanced antiproliferative effect in breast cancer cell lines, compared to either single K-lock or C-lock conjugates. A, SKBR-3 (HER2 3+), B, HCC1954 (HER2 3+), C, MCF-7 (HER2+/−), were all treated with either single conjugates or dual conjugates for 3 days. Percentage of cell viability at above indicated concentrations were shown and compared with single conjugates.
Figure 2:
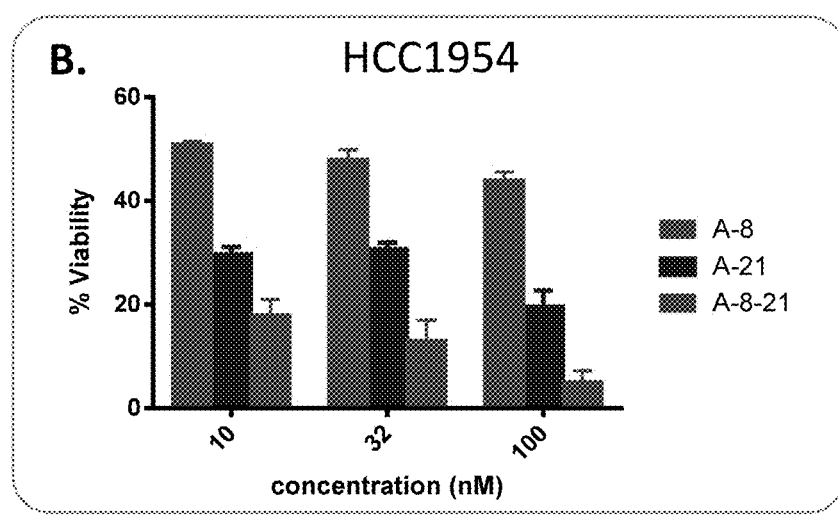
Figure 2:
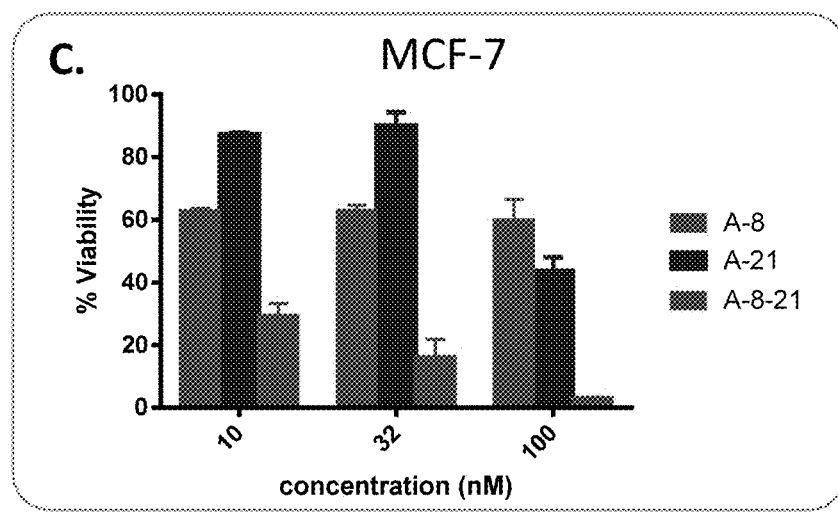

FIG. 2 shows anti-Her-2 (A) dual conjugates (K-lock+C-lock) induces enhanced antiproliferative effect in breast cancer cell lines, compared to either single K-lock or C-lock conjugates. A, SKBR-3 (HER2 3+), B, HCC1954 (HER2 3+), C, MCF-7 (HER2+/−), were all treated with either single conjugates or dual conjugates for 3 days. Percentage of cell viability at above indicated concentrations were shown and compared with single conjugates.

Figure 3:
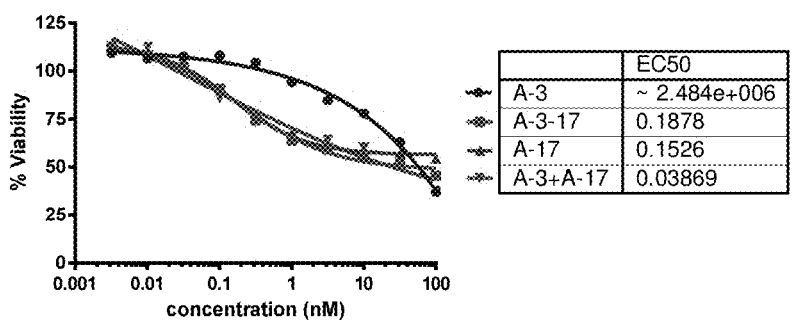
FIG. 3 shows anti-Her-2 (A) dual conjugates (K-lock+C-lock) induces enhanced antiproliferative effect in breast cancer cell lines, comparable to the combination of single K-lock and C-lock conjugates. A, SKBR-3 (HER2 3+), B, HCC1954 (HER2 3+), C, MCF-7 (HER2+/−), were all treated with either single conjugates or dual conjugates for 3 d. 1050 was determined as the concentration that showed 50% inhibition of cell growth.
Figure 3:
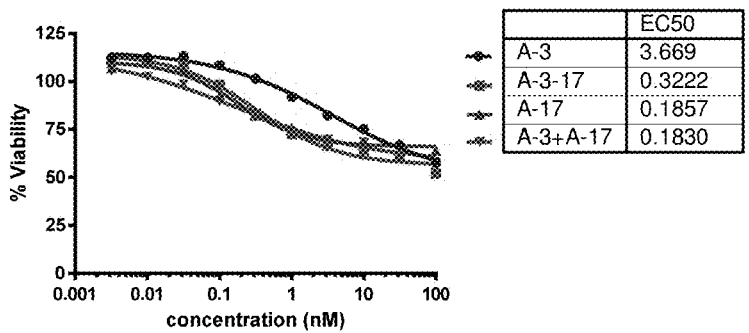
Figure 3:
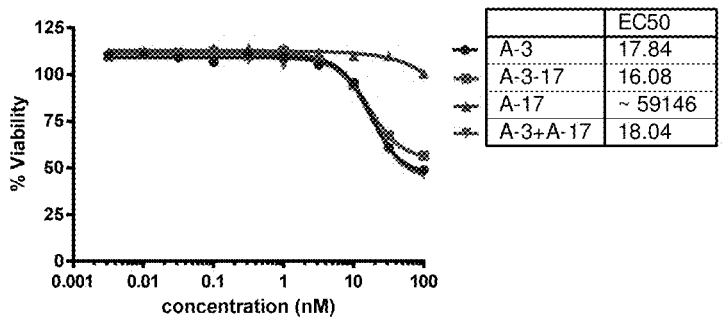

FIG. 3 shows anti-Her-2 (A) dual conjugates (K-lock+C-lock) induces enhanced antiproliferative effect in breast cancer cell lines, comparable to the combination of single K-lock and C-lock conjugates. A, SKBR-3 (HER2 3+), B, HCC1954 (HER2 3+), C, MCF-7 (HER2+/−), were all treated with either single conjugates or dual conjugates for 3 d. $IC_{50}$ was determined as the concentration that showed 50% inhibition of cell growth.

The invention claimed is:

1. A dual-drug conjugate comprising a structure of Formula I

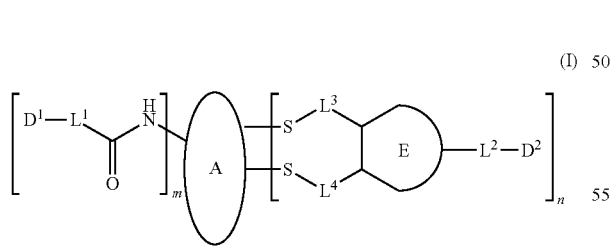

(I)

or a pharmaceutically acceptable salt thereof,
wherein:
A comprises an antibody or antigen-binding antibody fragment;
$D^1$ is an active agent;
each $L^1$ is independently a linker comprising at least one N (nitrogen) atom;
the nitrogen between the antibody or antigen binding antibody fragment and the carbonyl of $C(O)$—$L^1$-$D^1$ is the nitrogen of a Lys side chain of the antibody or antigen-binding antibody fragment;
$D^2$ an active agent, wherein $D^1$ and $D^2$ are different active agents;
each $L^2$ is independently a linker;
the E-component is selected from the group consisting of

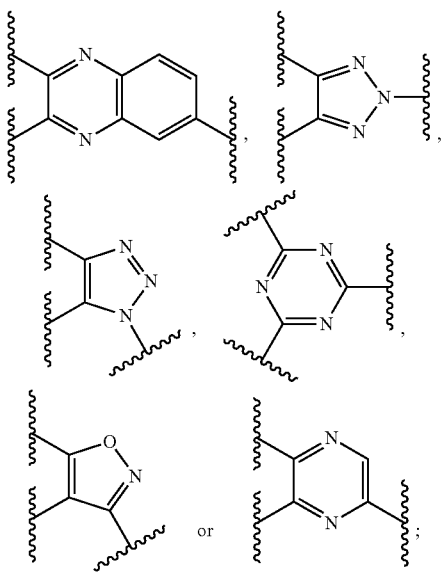

$L^3$ is —($CH_2$)—;
$L^4$ is —($CH_2$)—;
m is 1, 2, 3, 4, 5, 6, 7, 8, 9, or 10; and
n is 1, 2, 3, 4, 5, 6, 7, 8, 9, or 10.

2. The dual-drug conjugate of claim 1, wherein:

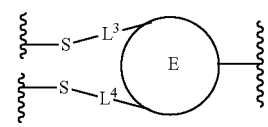

is:

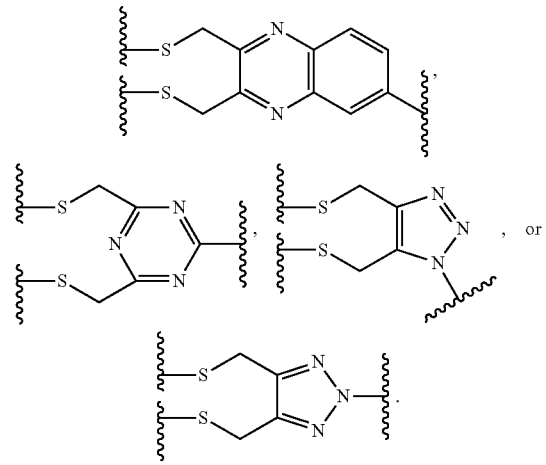

3. The dual-drug conjugate of claim 1, wherein $L^1$ comprises

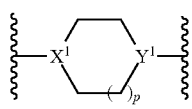

where $X^1$ is N (nitrogen) or CH; $Y^1$ is N (nitrogen), or CH; and p is 0, 1, or 2.

4. The active agent-conjugate of claim 1, wherein $L^1$ comprises

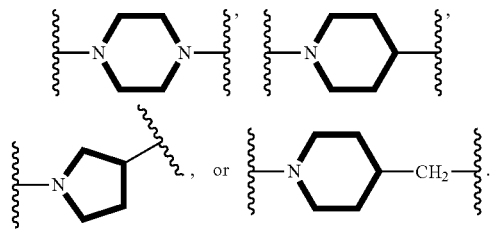

5. The dual-drug conjugate of claim 1, wherein $D^1$ is selected from the group consisting of tubulin binders, DNA alkylators, DNA intercalator, enzyme inhibitors, immune modulators, peptides, and nucleotides.

6. The dual-drug conjugate of claim 1, wherein $D^2$ is selected from the group consisting of tubulin binders, DNA alkylators, DNA intercalator, enzyme inhibitors, immune modulators, peptides, and nucleotides.

7. The dual-drug conjugate of claim 1, wherein $L^1$ or $L^2$ comprises —(CH$_2$)$_n$- where n is 1, 2, 3, 4, 5, 6, 7, 8, 9, or 10.

8. The dual-drug conjugate of claim 1, wherein $L^1$ or $L^2$ includes —(CH$_2$CH$_2$O)$_n$- where n is 1, 2, 3, 4, 5, 6, 7, 8, 9, or 10.

9. The dual-drug conjugate of claim 1, wherein the S-linked portion of

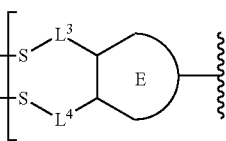

comprises a modified L-Alanine residue.

10. The dual-drug conjugate of claim 1, wherein each

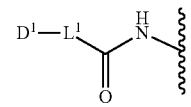

is:

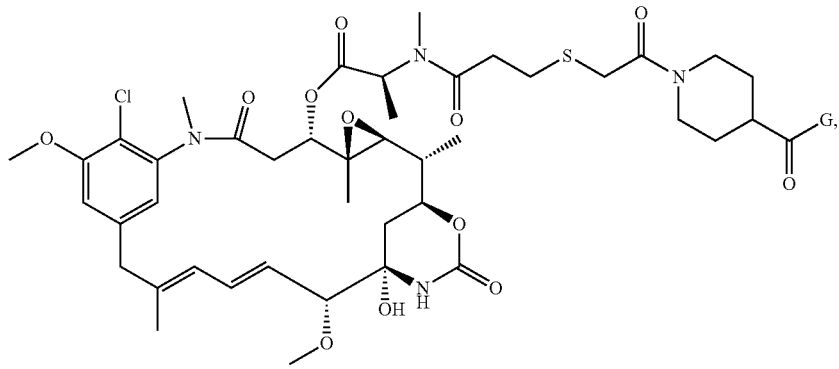

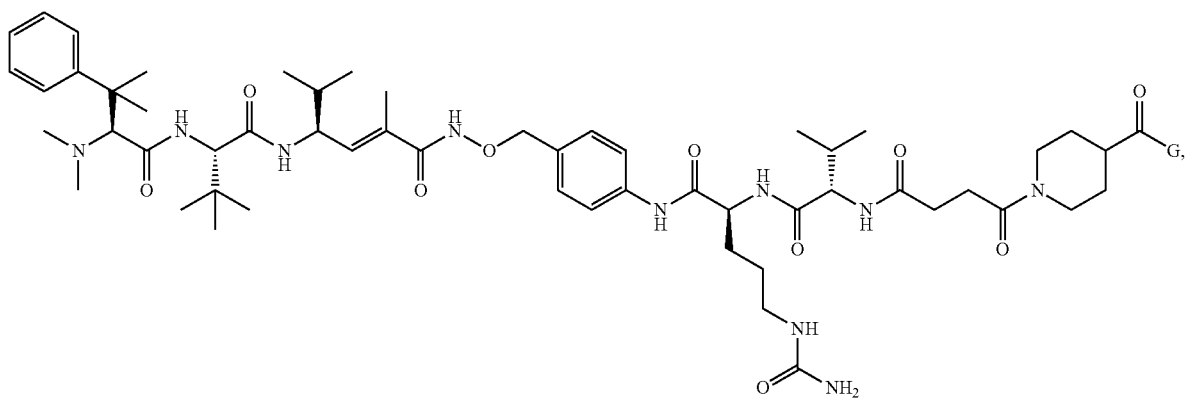

-continued
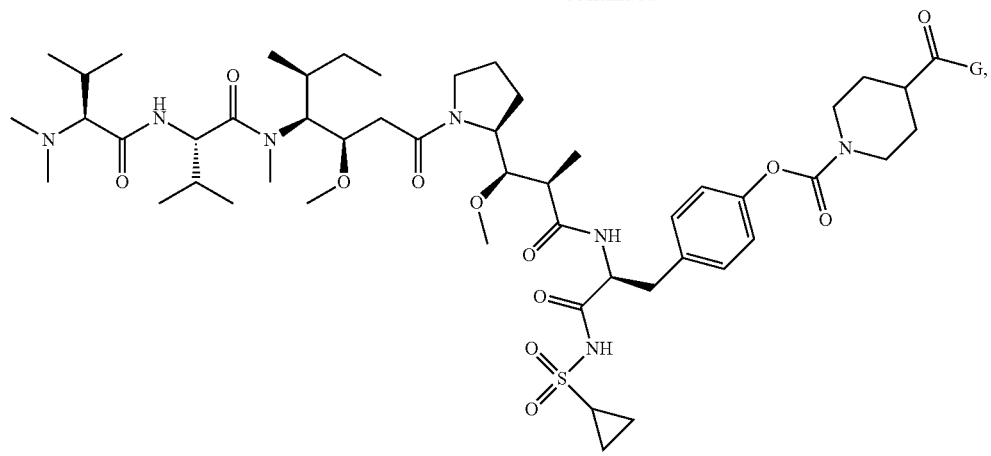
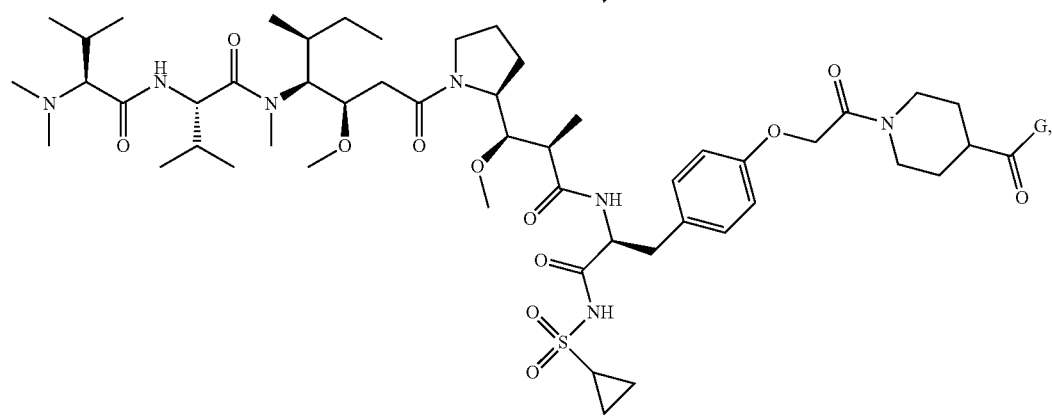
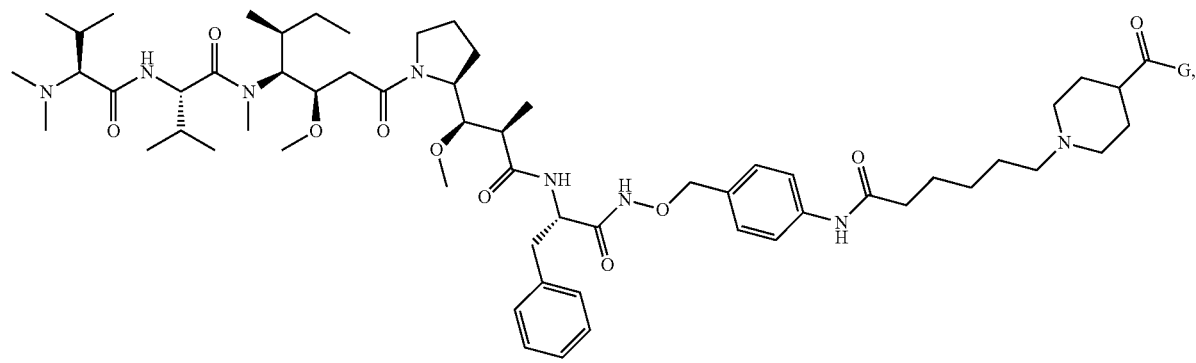
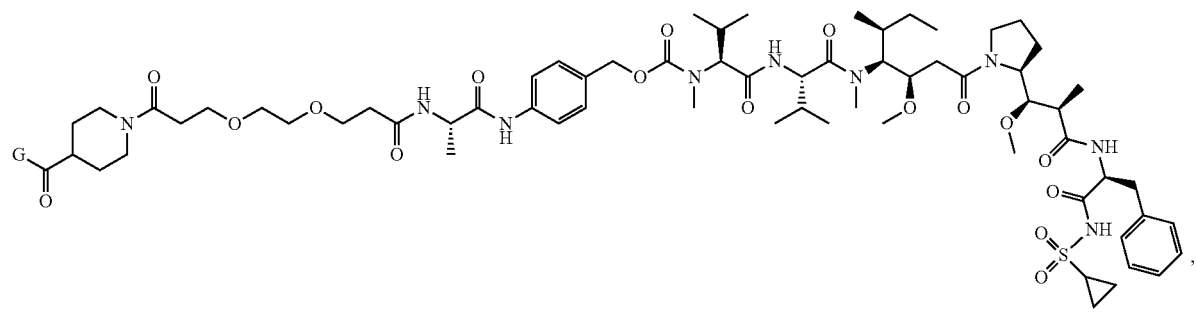

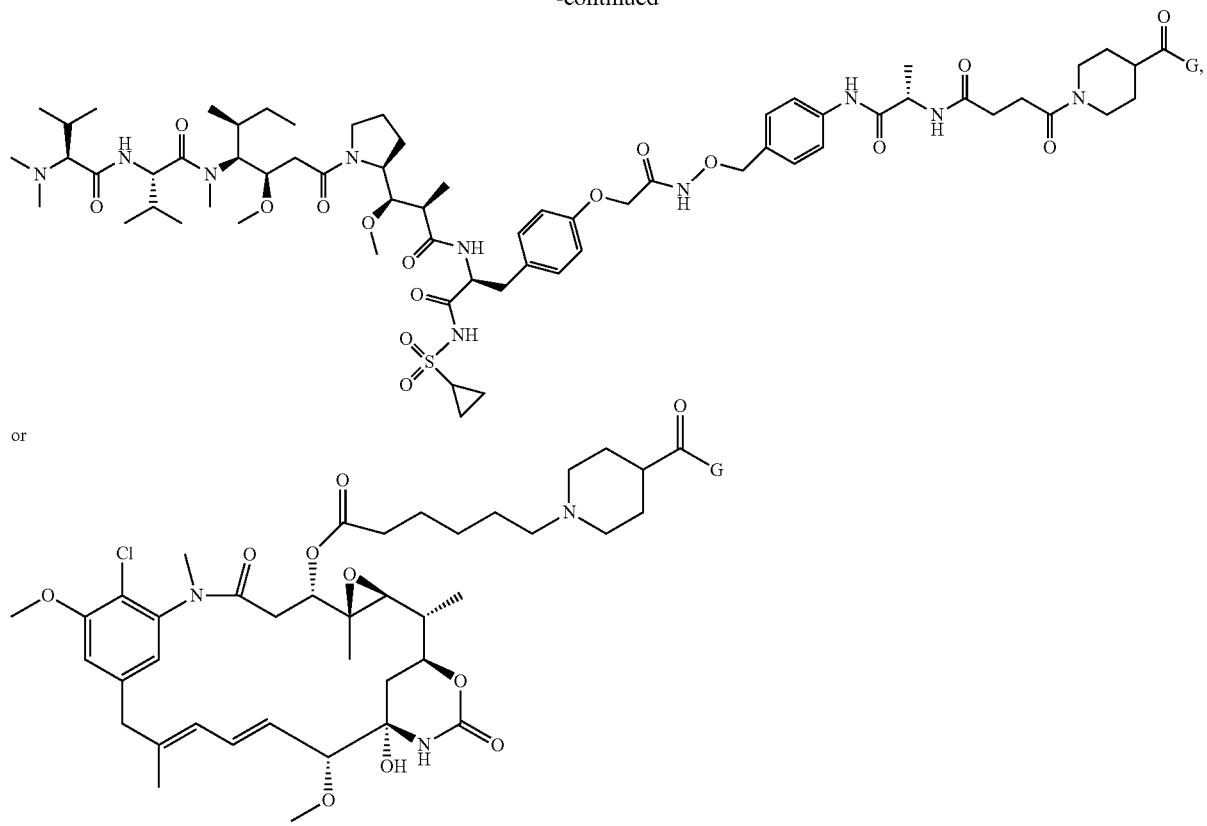
or
wherein G is —NH—.
11. The dual-drug conjugate of claim 1, wherein each
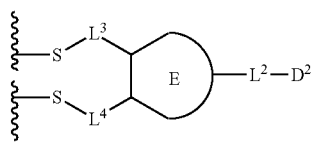
is:
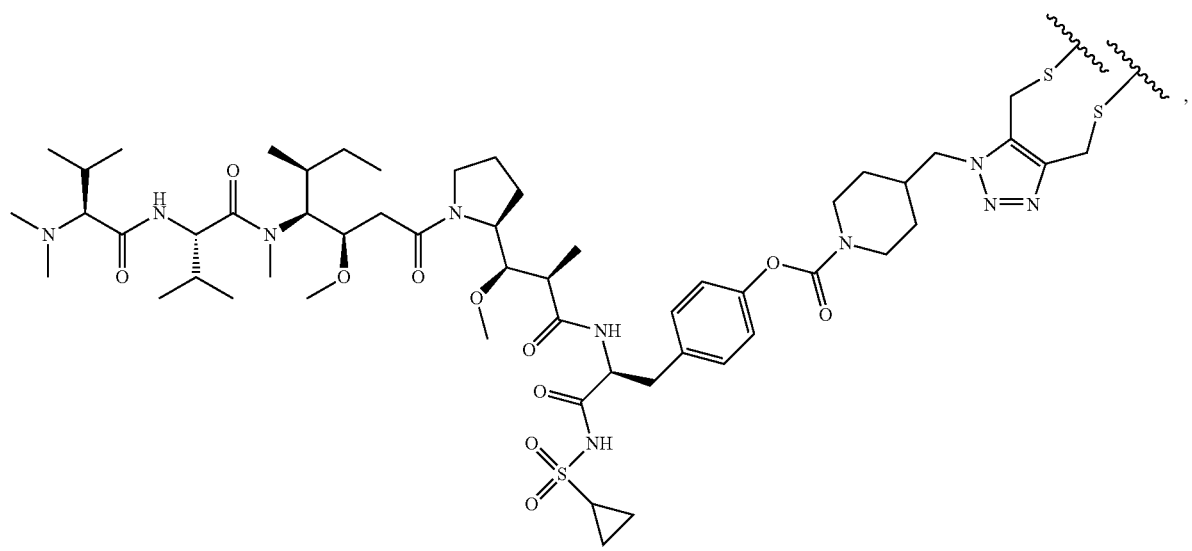

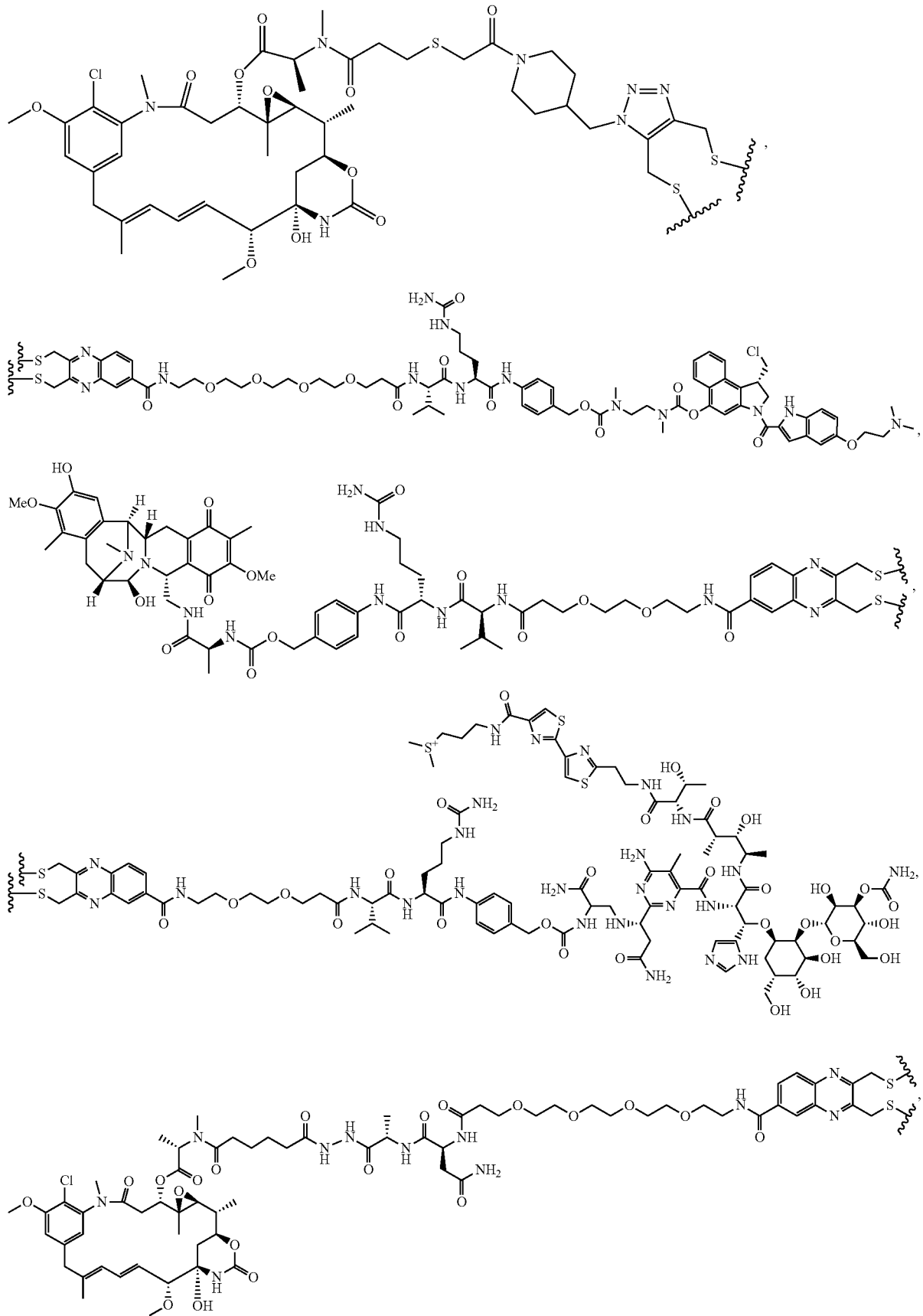

181 182
-continued
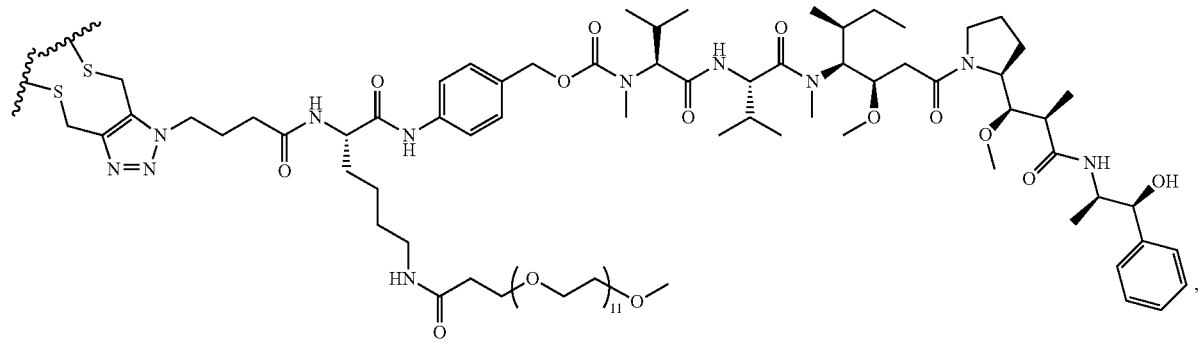
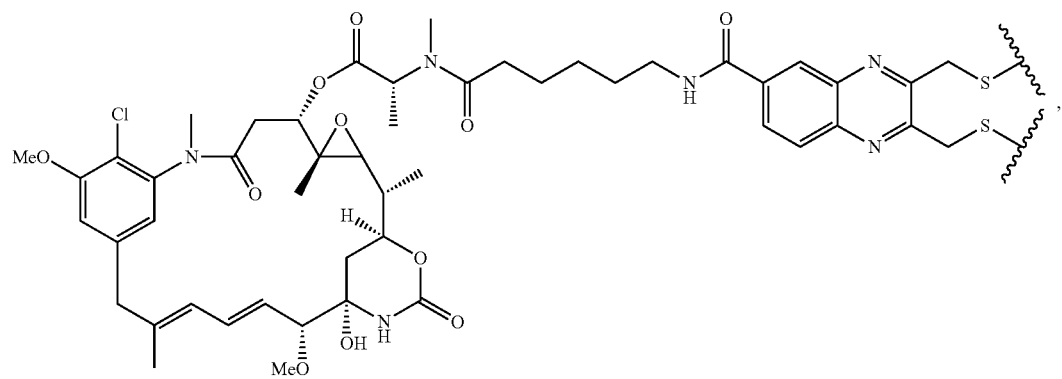
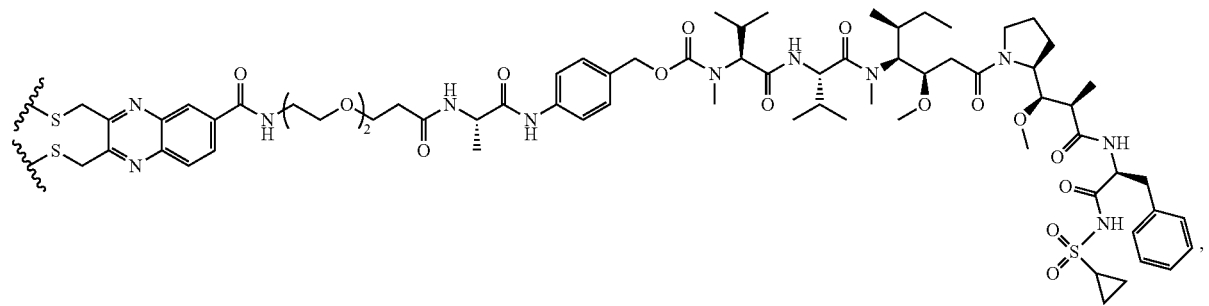
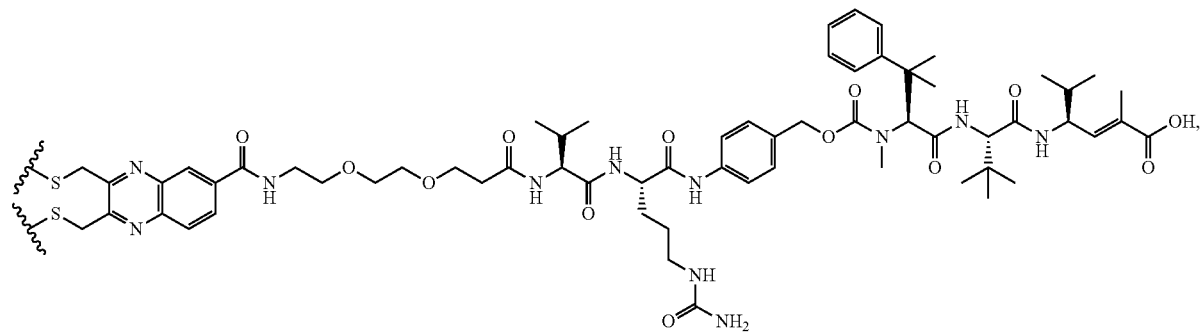

12. A dual-drug conjugate selected from the group consisting of:
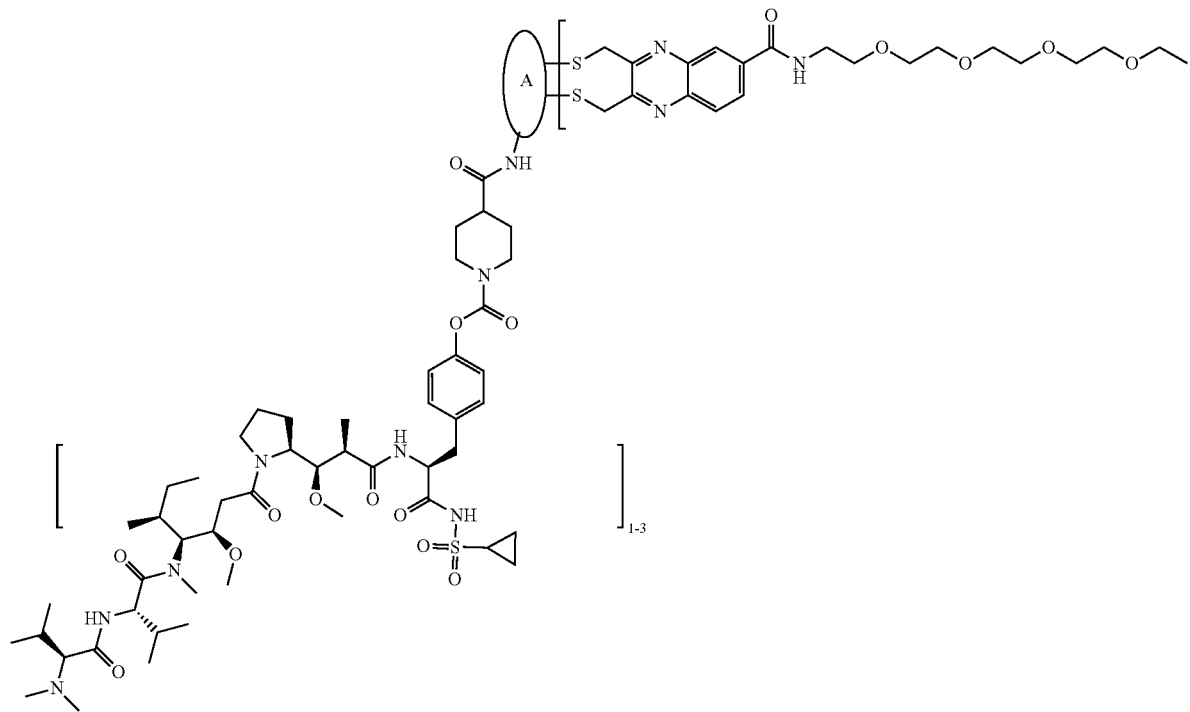
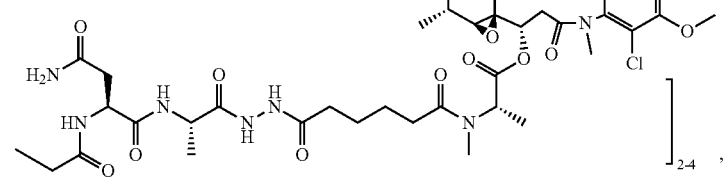

-continued
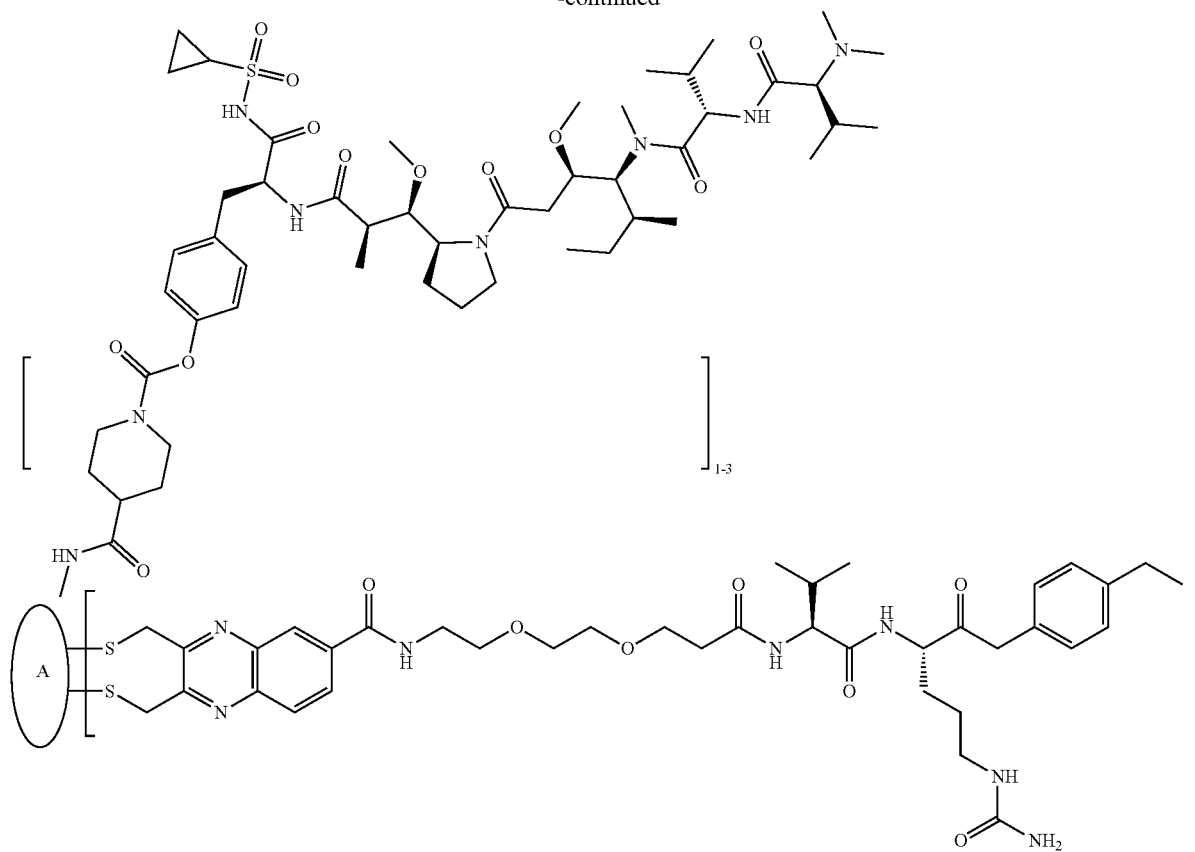
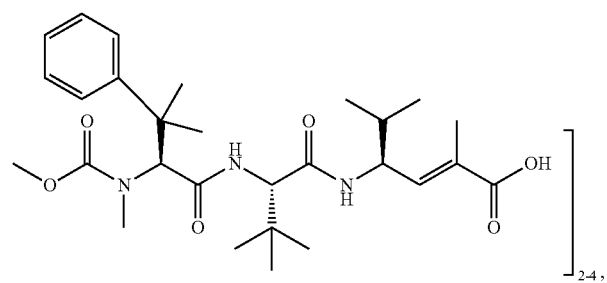
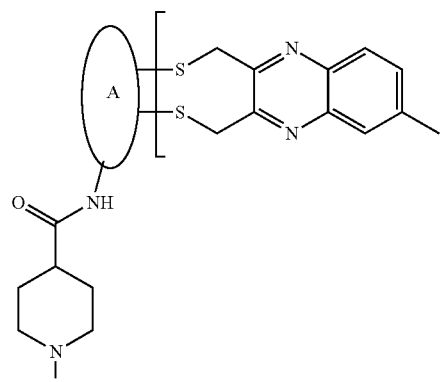

-continued
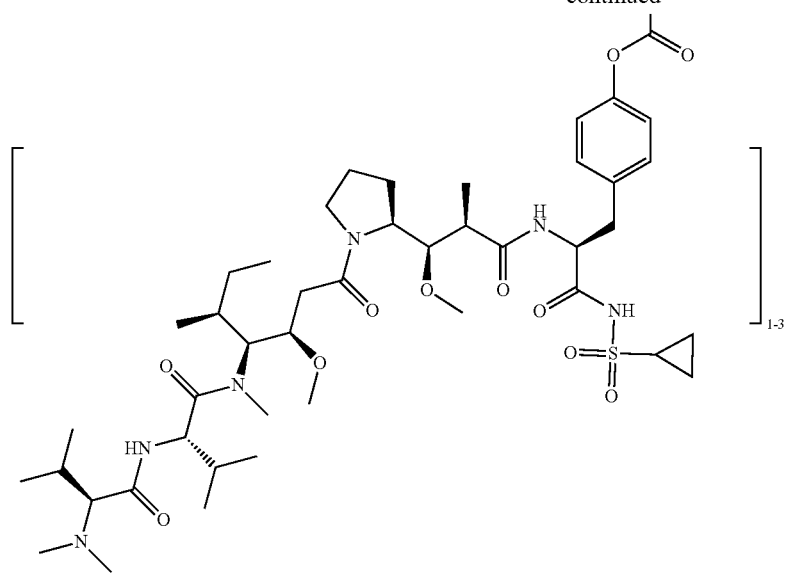
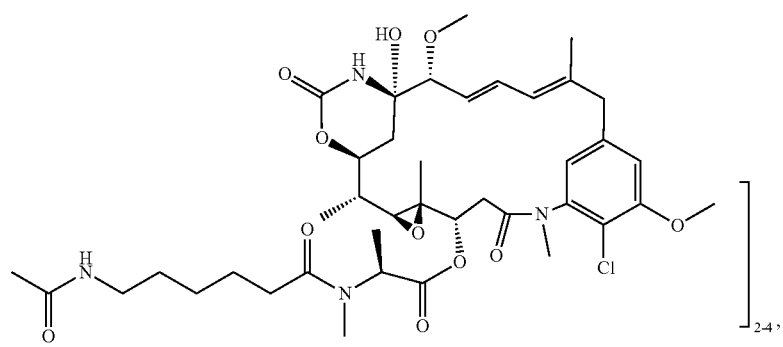
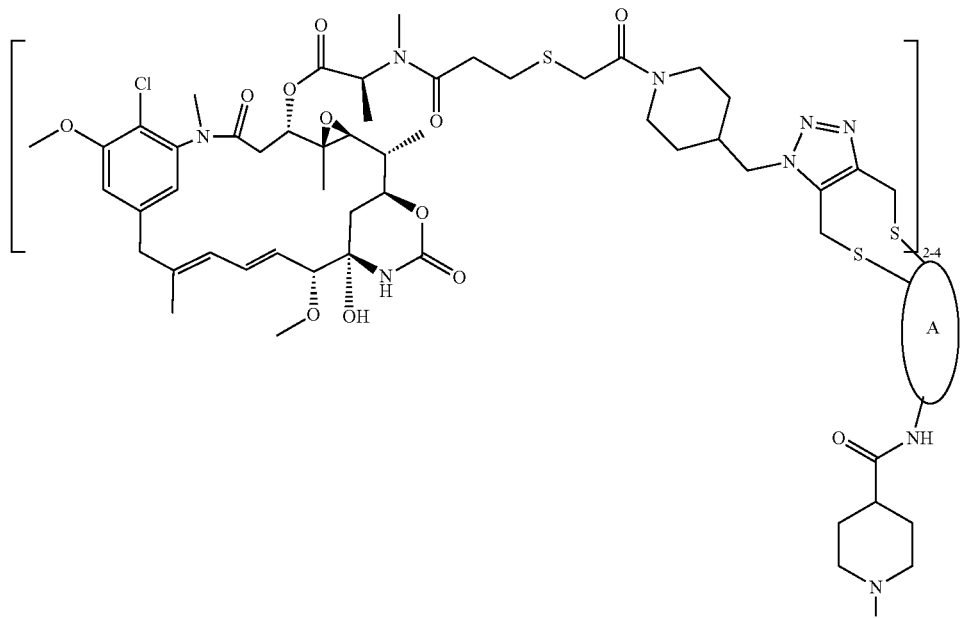

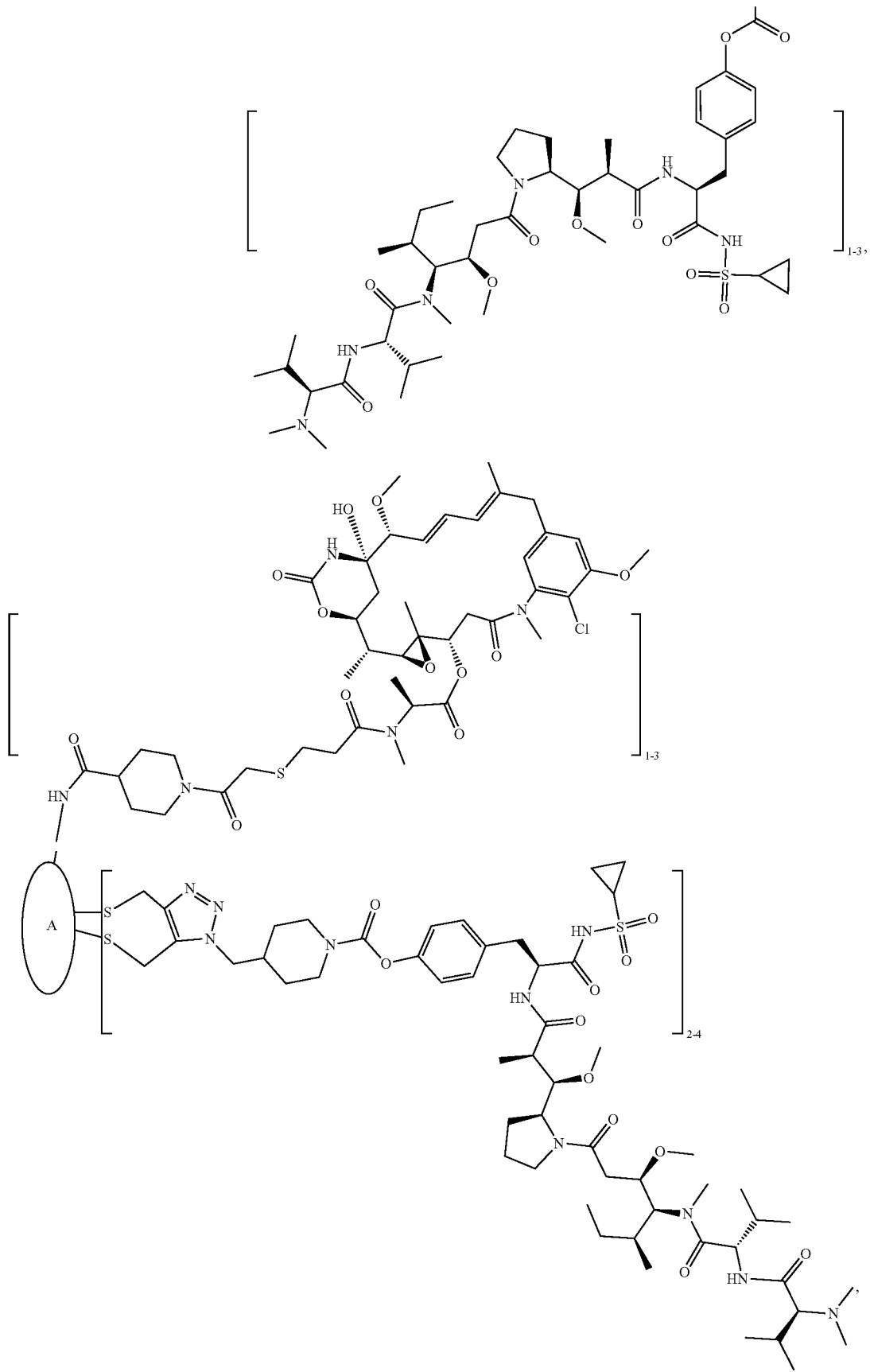

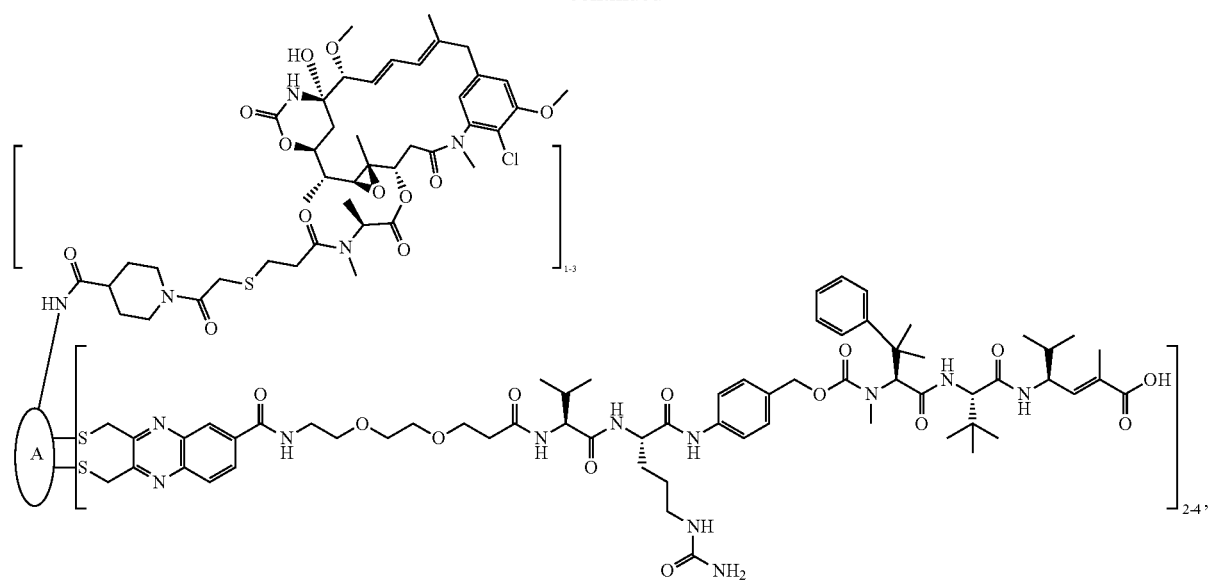
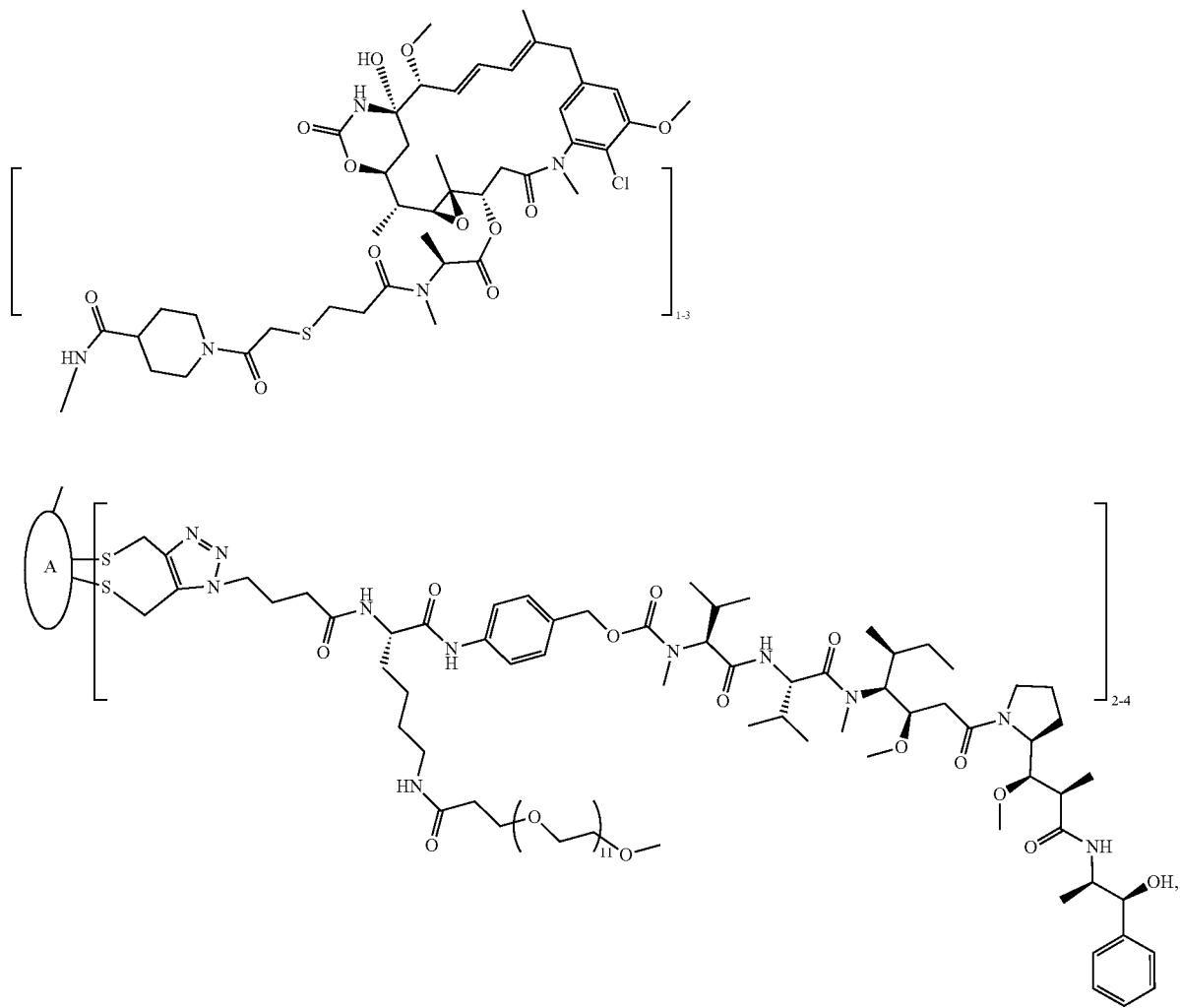
and

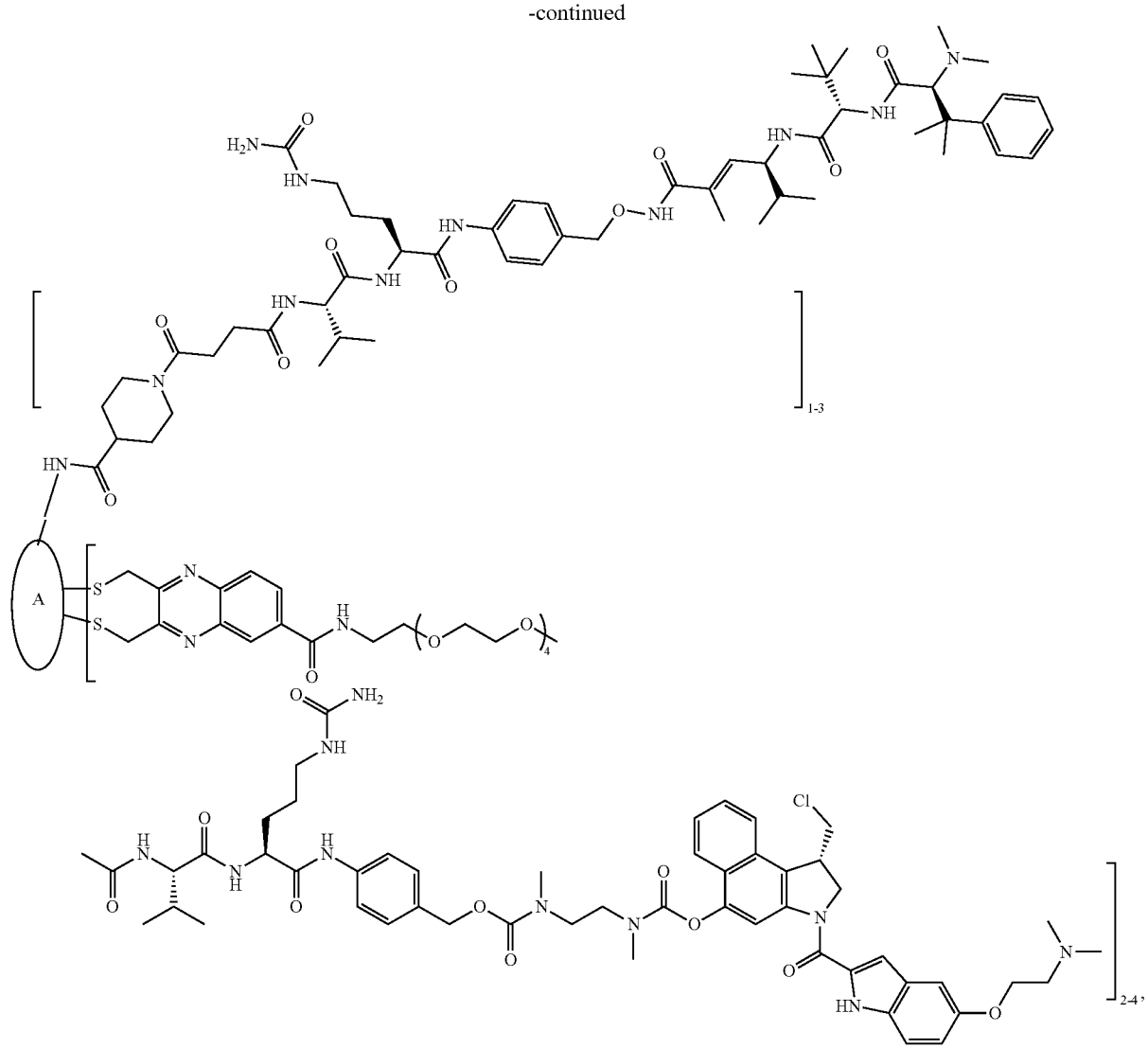
or a pharmaceutically acceptable salt thereof.
13. The dual-drug conjugate of claim 1, wherein A comprises an antibody.
14. The dual-drug conjugate of claim 1, wherein A comprises an antigen-binding antibody fragment.
* * * * *